United States Patent
Henry, Jr. et al.

(10) Patent No.: US 11,542,249 B2
(45) Date of Patent: Jan. 3, 2023

(54) BTK INHIBITOR COMPOUNDS

(71) Applicant: Eli Lilly and Company, Indianapolis, IN (US)

(72) Inventors: Kenneth James Henry, Jr., Carmel, IN (US); Albert Khilevich, Carmel, IN (US); Steven Lee Kuklish, Fishers, IN (US); Katherine Marie Partridge, Indianapolis, IN (US); Steven James Quimby, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 60 days.

(21) Appl. No.: 16/758,219

(22) PCT Filed: Oct. 30, 2018

(86) PCT No.: PCT/US2018/058104
§ 371 (c)(1),
(2) Date: Apr. 22, 2020

(87) PCT Pub. No.: WO2019/089512
PCT Pub. Date: May 9, 2019

(65) Prior Publication Data
US 2020/0290997 A1    Sep. 17, 2020

Related U.S. Application Data

(60) Provisional application No. 62/581,967, filed on Nov. 6, 2017.

(51) Int. Cl.
C07D 401/14 (2006.01)
C07D 403/14 (2006.01)
A61P 19/02 (2006.01)

(52) U.S. Cl.
CPC ............ C07D 401/14 (2013.01); A61P 19/02 (2018.01); C07D 403/14 (2013.01)

(58) Field of Classification Search
CPC .................... C07D 401/14; C07D 403/14
See application file for complete search history.

(56) References Cited

U.S. PATENT DOCUMENTS

2015/0152068 A1    6/2015   Angst

FOREIGN PATENT DOCUMENTS

| GB | 2516303 A | 1/2015 |
|---|---|---|
| WO | 2012/170976 A2 | 12/2012 |
| WO | 2014/093230 A2 | 6/2014 |
| WO | 2017/059280 A1 | 4/2017 |

OTHER PUBLICATIONS

International Searching Authority, International Search Report for PCT/US2018/058104, WO, A1, dated Jan. 25, 2019, Eli Lilly and Company.
Written Opinion of the International Searching Authority for PCT/US2018/058104, WO, A1, dated Jan. 25, 2019, Eli Lilly and Company.
Zou Yi, et al, Structure-based discovery of novel 4,5,6-trisubstituted pyrimidines as potent covalent Bruton's tyrosine kinas inhibitors, Bioorganic& Medical Chemistry Letters, Pergamon, Amsterdam, NL, vol. 26, No. 13, May 7, 2016, pp. 3052-3059.

*Primary Examiner* — Brian E McDowell
(74) *Attorney, Agent, or Firm* — Dan L Wood

(57) ABSTRACT

The invention provides BTK Inhibitor compounds of the formula

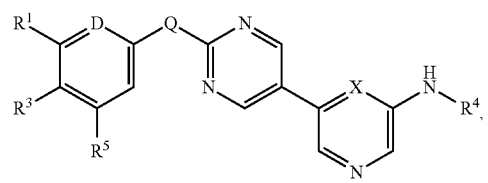

pharmaceutically acceptable salts, pharmaceutical compositions thereof, and methods of using these compounds, salts, or compositions to treat autoimmune diseases such as Rheumatoid Arthritis.

14 Claims, No Drawings

BTK INHIBITOR COMPOUNDS

The present disclosure provides compounds that are tyrosine kinase inhibitors, in particular Bruton's tyrosine kinase ("BTK") inhibitors, and are useful for the treatment of autoimmune or inflammatory diseases, such as Rheumatoid Arthritis ("RA") Multiple Sclerosis ("MS"), and/or Systemic Lupus Erythematosus ("SLE"). Processes for preparing these inhibitors, pharmaceutical compositions comprising these inhibitors, and methods of using these compounds and compositions are also provided.

In spite of progress made for treatment of RA, there remains a significant unmet need for improved therapies to provide safe and effective treatment of this and other autoimmune or inflammatory conditions. Current treatments employ non-steroidal anti-inflammatory drugs, glucocorticoids, and disease modifying anti-rheumatic drugs (DMARDs) such as methotrexate, janus kinase inhibitors, tumor necrosis factor inhibitors, costimulation modifiers, interleukin-6 inhibitors, and B cell depleting drugs. However, these agents have been reported to have various adverse effects, and treatment with biological agents require injections which some patients may prefer to avoid. Further, the current paradigm for the management of RA requires long term administration of aggressive immunosuppression, which induces sustained remission in less than 50% of patients (See F. H. Prince, et al., *Sustained rheumatoid arthritis remission is uncommon in clinical practice*, Arthritis Res. Ther. 14 (2) (2012) R68, *Targeted Treatments for Rheumatoid Arthritis* 2, Burmesterm G. R. and Pope, J. E., Lancet (2017), 389:2238-2248).

BTK is a member of the TEC family of non-receptor tyrosine kinases. It is essential for B cell receptor (BCR) mediated signaling and responses that maintain the B cell repertoire. Signaling through BCR controls a range of effector responses including activation, proliferation and differentiation of mature antibody producing cells. BTK inhibitors are believed to be useful for inhibition of autoantibody production, thereby treating autoantibody-mediated diseases. BTK is also expressed in other hematopoietic cells, such as monocytes, macrophages, and mast cells, where it regulates certain immune responses, such as TNF production stimulated through Fc-receptors. Thus, TNF mediated inflammation may be modulated by small molecule BTK inhibitors. Preclinical studies of small molecule BTK inhibitors have shown efficacy in collagen-induced arthritis and lupus models (See e.g. *Bruton's tyrosine kinase inhibitors for the treatment of rheumatoid arthritis*, Whang J. A. and Chang B. Y., Drug Discovery Today (2014), Volume 19, Number 8, 1200-1224). Targeting BTK with small molecule inhibitors may provide advantages over biological therapies for RA such as modulating B cell responses, and/or activation, while better maintaining desirable immunnocompetence (See e.g. *Targeting B cells in treatment of autoimmunity*, Franks, S. E., et al., Current Opinion in Immunology (2016), 43:39-45).

Accordingly, there remains an unmet need for improved agents that may provide a combined profile of safe, effective and convenient treatment of inflammatory and/or autoimmune disease, without the disadvantages possessed by prior agents. United States Application Publication US 2014/0162983 discloses certain Compositions and Methods for the Production of Pyrimidine and Pyridine Compounds with BTK Inhibitory Activity, and recites the compounds as useful in treating a number of diseases including cancer, lupus, allergic disorders, Sjogren's disease and rheumatoid arthritis.

The present invention provides alternative compounds which are useful in treatment of autoimmune diseases such as RA, MS, and/or SLE. In addition, the compounds provided address the need for treatment of BTK mediated conditions with improved efficacy, and side effect and/or tolerability profiles. The compounds of the present invention are BTK inhibitors, and demonstrate potent BTK inhibition with favorable selectivity relative to other TEC tyrosine kinases. As such, compounds of the present invention are believed to be useful for the treatment of conditions in which BTK signaling plays a role, such as RA, MS, and/or SLE.

The present invention provides a compound of the formula:

Formula I

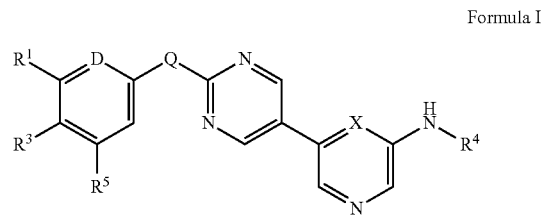

wherein:

D is —$CR^2$— or N,

Q is O or NH,

X is —CH— or N, $R^1$ is —H, —Cl, —F, —CN, —$CH_3$, —$CF_3$, —$OCHF_2$, —$OCH_3$, —$OCF_3$, or —C≡CH, $R^2$ is —H, —F or —$OCF_3$, $R^3$ is H, —Cl or —F, $R^4$ is

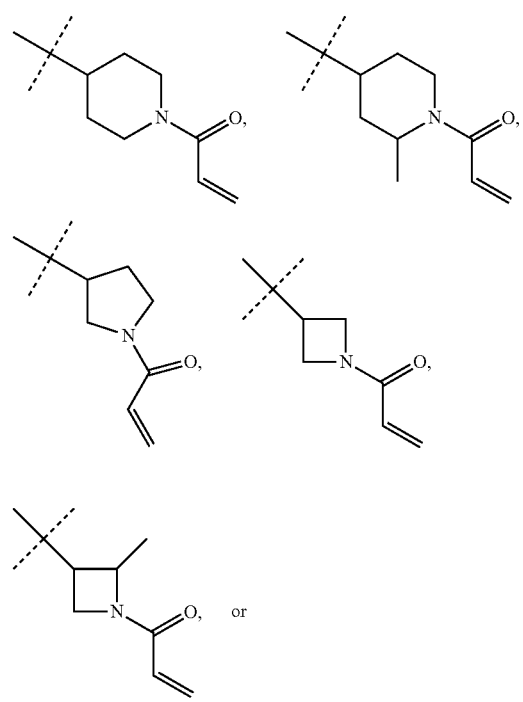

3
-continued

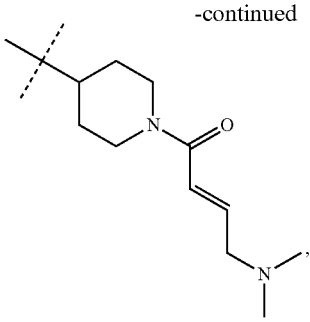

R⁵ is H or F,
or a pharmaceutically acceptable salt thereof.

In a preferred embodiment the present invention provides a compound of Formula I as defined above wherein D is —CR²—, R¹ is —Cl, R³ is —H, and R⁵ is H.

The present invention provides a compound of the Formula Ia:

Formula Ia

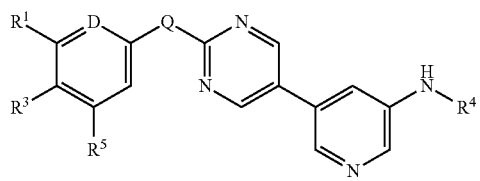

wherein:
D is —CR²— or N,
Q is O or NH,
R¹ is —H, —Cl, —F, —CN, —CH₃, —CF₃, —OCHF₂, —OCH₃, —OCF₃, or —C≡CH,
R² is —H, —F or —OCF₃,
R³ is —H, —Cl or —F,
R⁴ is

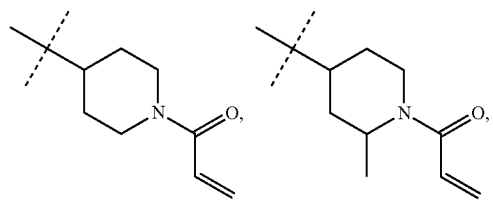

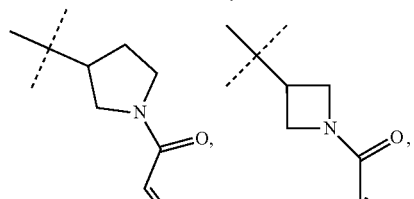

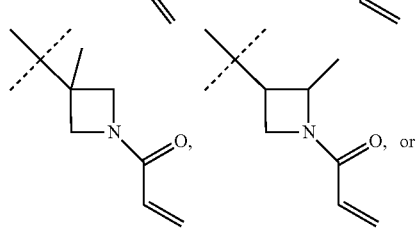

4
-continued

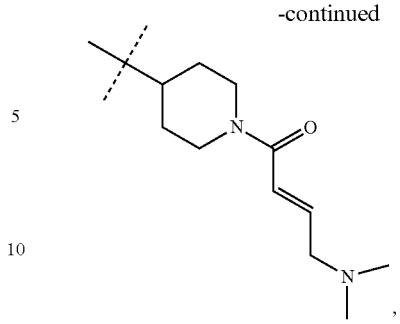

R⁵ is —H or —F,
or a pharmaceutically acceptable salt thereof.

In a preferred embodiment the present invention provides a compound of Formula Ia as defined above wherein D is —CR²—, R¹ is —Cl, R³ is —H, and R⁵ is —H.

The present invention provides a compound of the Formula Ib:

Formula Ib

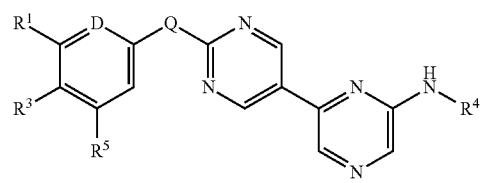

wherein:
D is —CR²— or N,
Q is O or NH,
R¹ is —H, —Cl, —F, —CN, —CH₃, —CF₃, —OCHF₂, —OCH₃, —OCF₃, or —C≡CH,
R² is —H, —F or —OCF₃,
R³ is —H, —Cl or —F,
R⁴ is

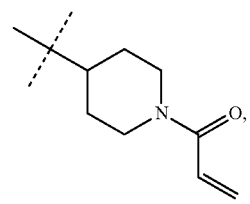

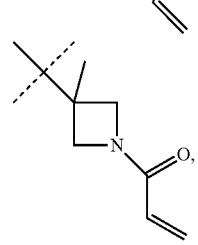

-continued

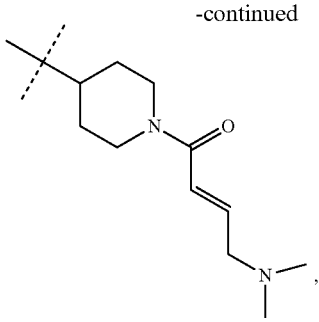

R⁵ is —H or —F,
or a pharmaceutically acceptable salt thereof.

In a preferred embodiment the present invention provides a compound of Formula Ib as defined above wherein D is —CR²—, R¹ is —Cl, R³ is —H, and R⁵ is —H.

The following particular embodiments are compounds and/or salts of Formula I, Ia, and/or Ib.

The present invention provides a compound which is 1-[4-[[5-[2-(3-chlorophenoxy)pyrimidin-5-yl]-3-pyridyl]amino]-1-piperidyl]prop-2-en-1-one or a pharmaceutically acceptable salt thereof.

The present invention provides a compound which is 1-[3-[[6-[2-(3-chlorophenoxy)pyrimidin-5-yl]pyrazin-2-yl]amino]azetidin-1-yl]prop-2-en-1-one or a pharmaceutically acceptable salt thereof.

The present invention provides a compound which is 1-[4-[[6-[2-(3-chlorophenoxy)pyrimidin-5-yl]pyrazin-2-yl]amino]-1-piperidyl]prop-2-en-1-one or a pharmaceutically acceptable salt thereof.

The present invention provides a compound which is 1-[4-[[5-[2-(3-chloroanilino)pyrimidin-5-yl]-3-pyridyl]amino]-1-piperidyl]prop-2-en-1-one or a pharmaceutically acceptable salt thereof.

The present invention provides a compound which is 1-[4-[[5-[2-[[6-(trifluoromethyl)-2-pyridyl]amino]pyrimidin-5-yl]-3-pyridyl]amino]-1-piperidyl]prop-2-en-1-one or a pharmaceutically acceptable salt thereof.

The present invention provides a compound selected from the group consisting of:

1-[3-[[5-[2-(3-chloro-2-fluoro-phenoxy)pyrimidin-5-yl]-3-pyridyl]amino]azetidin-1-yl]prop-2-en-1-one;
3-[5-[5-[(1-prop-2-enoylazetidin-3-yl)amino]-3-pyridyl]pyrimidin-2-yl]oxybenzonitrile;
1-[3-[[5-[2-3-(difluoromethoxy)phenoxy]pyrimidin-5-yl]-3-pyridyl]amino]azetidin-1-yl]prop-2-en-1-one;
1-[(3S)-3-[[5-[2-[3-(difluoromethoxy)phenoxy]pyrimidin-5-yl]-3-pyridyl]amino]pyrrolidin-1-yl]prop-2-en-1-one;
1-[(3S)-3-[[5-[2-(3-chlorophenoxy)pyrimidin-5-yl]-3-pyridyl]amino]pyrrolidin-1-yl]prop-2-en-1-one;
1-[3-[[5-[2-(3-chlorophenoxy)pyrimidin-5-yl]-3-pyridyl]amino]azetidin-1-yl]prop-2-en-1-one;
1-[3-[[5-[2-[3-(trifluoromethyl)phenoxy]pyrimidin-5-yl]-3-pyridyl]amino]azetidin-1-yl]prop-2-en-1-one;
1-[3-[[5-[2-[3-(difluoromethoxy)-4-fluoro-phenoxy]pyrimidin-5-yl]-3-pyridyl]amino]azetidin-1-yl]prop-2-en-1-one;
1-[3-[[5-[2-[3-(trifluoromethoxy)phenoxy]pyrimidin-5-yl]-3-pyridyl]amino]azetidin-1-yl]prop-2-en-1-one;
1-[3-[[5-[2-(3-fluorophenoxy)pyrimidin-5-yl]-3-pyridyl]amino]azetidin-1-yl]prop-2-en-1-one;
1-[3-[[5-[2-(3-chlorophenoxy)pyrimidin-5-yl]-3-pyridyl]amino]-3-methyl-azetidin-1-yl]prop-2-en-1-one;
1-[3-[[5-[2-(3-chloro-4-fluoro-phenoxy)pyrimidin-5-yl]-3-pyridyl]amino]azetidin-1-yl]prop-2-en-1-one;
1-[3-[[5-[2-(3-ethynylphenoxy)pyrimidin-5-yl]-3-pyridyl]amino]azetidin-1-yl]prop-2-en-1-one;
1-[3-[[5-[2-(3-chloroanilino)pyrimidin-5-yl]-3-pyridyl]amino]azetidin-1-yl]prop-2-en-1-one;
(S)-1-(3-((5-(2-((3-(difluoromethoxy)phenyl)amino)pyrimidin-5-yl)pyridin-3-yl)amino)pyrrolidin-1-yl)prop-2-en-1-one;
1-{(3S)-3-[(5-{2-[(6-methylpyridin-2-yl)amino]pyrimidin-5-yl}pyridin-3-yl)amino]pyrrolidin-1-yl}prop-2-en-1-one;
1-[3-[[5-[2-[3-(trifluoromethyl)anilino]pyrimidin-5-yl]-3-pyridyl]amino]azetidin-1-yl]prop-2-en-1-one;
1-[4-[[5-[2-(3-chloroanilino)pyrimidin-5-yl]-3-pyridyl]amino]-1-piperidyl]prop-2-en-1-one;
1-[4-[[5-[2-[(6-methyl-2-pyridyl)amino]pyrimidin-5-yl]-3-pyridyl]amino]-1-piperidyl]prop-2-en-1-one;
1-[4-[[5-[2-[[6-(trifluoromethyl)-2-pyridyl]amino]pyrimidin-5-yl]-3-pyridyl]amino]-1-piperidyl]prop-2-en-1-one;
1-[4-[[5-[2-(2-pyridylamino)pyrimidin-5-yl]-3-pyridyl]amino]-1-piperidyl]prop-2-en-1-one;
(E)-1-[4-[[5-[2-(3-chloroanilino)pyrimidin-5-yl]-3-pyridyl]amino]-1-piperidyl]-4-(dimethylamino)but-2-en-1-one;
1-[3-[[6-[2-[3-(difluoromethoxy)phenoxy]pyrimidin-5-yl]pyrazin-2-yl]amino]azetidin-1-yl]prop-2-en-1-one;
1-[3-[[6-[2-(3-fluorophenoxy)pyrimidin-5-yl]pyrazin-2-yl]amino]azetidin-1-yl]prop-2-en-1-one;
1-[3-[[6-[2-[3-(trifluoromethyl)phenoxy]pyrimidin-5-yl]pyrazin-2-yl]amino]azetidin-1-yl]prop-2-en-1-one;
1-[3-[[6-[2-[3-(trifluoromethoxy)phenoxy]pyrimidin-5-yl]pyrazin-2-yl]amino]azetidin-1-yl]prop-2-en-1-one;
1-[3-[[6-(2-phenoxypyrimidin-5-yl)pyrazin-2-yl]amino]azetidin-1-yl]prop-2-en-1-one;
1-[3-[[6-[2-(3-chlorophenoxy)pyrimidin-5-yl]pyrazin-2-yl]amino]-3-methyl-azetidin-1-yl]prop-2-en-1-one;
1-[3-[[6-[2-(3,5-difluorophenoxy)pyrimidin-5-yl]pyrazin-2-yl]amino]azetidin-1-yl]prop-2-en-1-one;
1-[3-[[6-[2-(3-chlorophenoxy)pyrimidin-5-yl]pyrazin-2-yl]amino]azetidin-1-yl]prop-2-en-1-one;
1-[(2S,3R)-3-[[6-[2-(3-chlorophenoxy)pyrimidin-5-yl]pyrazin-2-yl]amino]-2-methyl-azetidin-1-yl]prop-2-en-1-one, Isomer 1;
1-[(3S)-3-[[6-[2-[3-(trifluoromethoxy)anilino]pyrimidin-5-yl]pyrazin-2-yl]amino]pyrrolidin-1-yl]prop-2-en-1-one;
1-[(3S)-3-[[6-[2-(3-chloroanilino)pyrimidin-5-yl]pyrazin-2-yl]amino]pyrrolidin-1-yl]prop-2-en-1-one;
1-[3-[[6-[2-(3-chloro-4-fluoro-anilino)pyrimidin-5-yl]pyrazin-2-yl]amino]azetidin-1-yl]prop-2-en-1-one;
1-[(3S)-3-[[6-[2-[2-(trifluoromethoxy)anilino]pyrimidin-5-yl]pyrazin-2-yl]amino]pyrrolidin-1-yl]prop-2-en-1-one;
1-[3-[[6-[2-[3-(trifluoromethoxy)anilino]pyrimidin-5-yl]pyrazin-2-yl]amino]azetidin-1-yl]prop-2-en-1-one;
1-[4-[[6-[2-[3-(difluoromethoxy)phenoxy]pyrimidin-5-yl]pyrazin-2-yl]amino]-1-piperidyl]prop-2-en-1-one;
1-[(3S)-3-[[6-[2-[3-(difluoromethoxy)anilino]pyrimidin-5-yl]pyrazin-2-yl]amino]pyrrolidin-1-yl]prop-2-en-1-one;
1-[3-[[6-[2-[(6-methyl-2-pyridyl)amino]pyrimidin-5-yl]pyrazin-2-yl]amino]azetidin-1-yl]prop-2-en-1-one;
1-[3-[[6-[2-(4-chlorophenoxy)pyrimidin-5-yl]pyrazin-2-yl]amino]azetidin-1-yl]prop-2-en-1-one;
1-[3-[[6-[2-(3-methoxyphenoxy)pyrimidin-5-yl]pyrazin-2-yl]amino]azetidin-1-yl]prop-2-en-1-one;
1-[3-[[6-[2-[2-(trifluoromethoxy)anilino]pyrimidin-5-yl]pyrazin-2-yl]amino]azetidin-1-yl]prop-2-en-1-one;
1-[4-[[6-[2-(3-chlorophenoxy)pyrimidin-5-yl]pyrazin-2-yl]amino]-1-piperidyl]prop-2-en-1-one;

(E)-1-[4-[[6-[2-(3-chlorophenoxy)pyrimidin-5-yl]pyrazin-2-yl]amino]-1-piperidyl]-4-(dimethylamino)but-2-en-1-one;

(E)-1-[4-[[6-[2-(3-chloroanilino)pyrimidin-5-yl]pyrazin-2-yl]amino]-1-piperidyl]-4-(dimethylamino)but-2-en-1-one; and 1-[4-[[5-[2-(3-chloroanilino)pyrimidin-5-yl]-3-pyridyl]amino]-2-methyl-1-piperidyl]prop-2-en-1-one, or a pharmaceutically acceptable salt thereof.

Further, the present invention provides a pharmaceutical composition comprising a compound of Formula I, Ia, and/or Ib, or a pharmaceutically acceptable salt thereof, and a pharmaceutically acceptable carrier, diluent or excipient.

Further, the present invention provides a compound of Formula I, or a pharmaceutically acceptable salt thereof, for use in therapy. Further, the present invention provides a compound of Formula Ia, or a pharmaceutically acceptable salt thereof, for use in therapy. Further, the present invention provides a compound of Formula Ib, or a pharmaceutically acceptable salt thereof, for use in therapy.

Further, the present invention provides a compound of Formula I, or a pharmaceutically acceptable salt thereof, for use in the treatment of Rheumatoid Arthritis. Further, the present invention provides a compound of Formula I, or a pharmaceutically acceptable salt thereof, for use in the treatment of Multiple Sclerosis. Further, the present invention provides a compound of Formula I, or a pharmaceutically acceptable salt thereof, for use in the treatment of Systemic Lupus Erythematosus. Further, the present invention provides a compound of Formula I, or a pharmaceutically acceptable salt thereof, for use in the treatment of Sjögren's Syndrome. Further, the present invention provides a compound of Formula I, or a pharmaceutically acceptable salt thereof, for use in the treatment of Pemphigus.

Further, the present invention provides a compound of Formula Ia, or a pharmaceutically acceptable salt thereof, for use in the treatment of Rheumatoid Arthritis. Further, the present invention provides a compound of Formula Ia, or a pharmaceutically acceptable salt thereof, for use in the treatment of Multiple Sclerosis. Further, the present invention provides a compound of Formula Ia, or a pharmaceutically acceptable salt thereof, for use in the treatment of Systemic Lupus Erythematosus. Further, the present invention provides a compound of Formula Ia, or a pharmaceutically acceptable salt thereof, for use in the treatment of Sjögren's Syndrome. Further, the present invention provides a compound of Formula Ia, or a pharmaceutically acceptable salt thereof, for use in the treatment of Pemphigus.

Further, the present invention provides a compound of Formula Ib, or a pharmaceutically acceptable salt thereof, for use in the treatment of Rheumatoid Arthritis. Further, the present invention provides a compound of Formula Ib, or a pharmaceutically acceptable salt thereof, for use in the treatment of Multiple Sclerosis. Further, the present invention provides a compound of Formula Ib, or a pharmaceutically acceptable salt thereof, for use in the treatment of Systemic Lupus Erythematosus. Further, the present invention provides a compound of Formula Ib, or a pharmaceutically acceptable salt thereof, for use in the treatment of Sjögren's Syndrome. Further, the present invention provides a compound of Formula Ib, or a pharmaceutically acceptable salt thereof, for use in the treatment of Pemphigus.

Further, the present invention provides 1-[(3S)-3-[[5-[2-[3-(difluoromethoxy)phenoxy]pyrimidin-5-yl]-3-pyridyl]amino]pyrrolidin-1-yl]prop-2-en-1-one, or a pharmaceutically acceptable salt thereof, for use in the treatment of Rheumatoid Arthritis. Further, the present invention provides 1-[(3S)-3-[[5-[2-[3-(difluoromethoxy)phenoxy]pyrimidin-5-yl]-3-pyridyl]amino]pyrrolidin-1-yl]prop-2-en-1-one, or a pharmaceutically acceptable salt thereof, for use in the treatment of Multiple Sclerosis. Further, the present invention provides 1-[(3S)-3-[[5-[2-[3-(difluoromethoxy)phenoxy]pyrimidin-5-yl]-3-pyridyl]amino]pyrrolidin-1-yl]prop-2-en-1-one, or a pharmaceutically acceptable salt thereof, for use in the treatment of Systemic Lupus Erythematosus. Further, the present invention provides 1-[(3S)-3-[[5-[2-[3-(difluoromethoxy)phenoxy]pyrimidin-5-yl]-3-pyridyl]amino]pyrrolidin-1-yl]prop-2-en-1-one, or a pharmaceutically acceptable salt thereof, for use in the treatment of Sjögren's Syndrome. Further, the present invention provides 1-[(3S)-3-[[5-[2-[3-(difluoromethoxy)phenoxy]pyrimidin-5-yl]-3-pyridyl]amino]pyrrolidin-1-yl]prop-2-en-1-one, or a pharmaceutically acceptable salt thereof, for use in the treatment of Pemphigus.

Further, the present invention provides 1-[4-[[5-[2-(3-chlorophenoxy)pyrimidin-5-yl]-3-pyridyl]amino]-1-piperidyl]prop-2-en-1-one, or a pharmaceutically acceptable salt thereof, for use in the treatment of Rheumatoid Arthritis. Further, the present invention provides 1-[4-[[5-[2-(3-chlorophenoxy)pyrimidin-5-yl]-3-pyridyl]amino]-1-piperidyl]prop-2-en-1-one, or a pharmaceutically acceptable salt thereof, for use in the treatment of Multiple Sclerosis. Further, the present invention provides 1-[4-[[5-[2-(3-chlorophenoxy)pyrimidin-5-yl]-3-pyridyl]amino]-1-piperidyl]prop-2-en-1-one, or a pharmaceutically acceptable salt thereof, for use in the treatment of Systemic Lupus Erythematosus. Further, the present invention provides 1-[4-[[5-[2-(3-chlorophenoxy)pyrimidin-5-yl]-3-pyridyl]amino]-1-piperidyl]prop-2-en-1-one, or a pharmaceutically acceptable salt thereof, for use in the treatment of Sjögren's Syndrome. Further, the present invention provides 1-[4-[[5-[2-(3-chlorophenoxy)pyrimidin-5-yl]-3-pyridyl]amino]-1-piperidyl]prop-2-en-1-one, or a pharmaceutically acceptable salt thereof, for use in the treatment of Pemphigus.

The present invention further provides the use of a compound of Formula I, Ia, and/or Ib, or a pharmaceutical salt thereof for the manufacture of a medicament for treating Rheumatoid Arthritis. The present invention further provides the use of a compound of Formula I, Ia, and/or Ib, or a pharmaceutical salt thereof for the manufacture of a medicament for treating Multiple Sclerosis. The present invention further provides the use of a compound of Formula I, Ia, and/or Ib, or a pharmaceutical salt thereof for the manufacture of a medicament for treating Systemic Lupus Erythematosus. The present invention further provides the use of a compound of Formula I, Ia, and/or Ib, or a pharmaceutical salt thereof for the manufacture of a medicament for treating Sjögren's Syndrome. The present invention further provides the use of a compound of Formula I, Ia, and/or Ib, or a pharmaceutical salt thereof for the manufacture of a medicament for treating Pemphigus.

The present invention provides a pharmaceutical composition comprising a compound or salt of Formula I, Ia, and/or Ib, and a pharmaceutically acceptable carrier or diluent, for use in the treatment of Rheumatoid Arthritis. The present invention provides a pharmaceutical composition comprising a compound or salt of Formula I, Ia, and/or Ib, and a pharmaceutically acceptable carrier or diluent, for use in the treatment of Multiple Sclerosis. The present invention provides a pharmaceutical composition comprising a compound or salt of Formula I, Ia, and/or Ib, and a pharmaceutically acceptable carrier or diluent, for use in the treatment of Systemic Lupus Erythematosus. The present invention provides a pharmaceutical composition comprising a compound or salt of Formula I, Ia, and/or Ib, and a pharmaceutically acceptable carrier or diluent, for use in the treatment of Sjögren's Syndrome. The present invention provides a pharmaceutical composition comprising a compound or salt of Formula I, Ia, and/or Ib, and a pharmaceutically acceptable carrier or diluent, for use in the treatment of Pemphigus.

Further, the present invention provides a method of treating Rheumatoid Arthritis, comprising administering to a patient in need thereof an effective amount of a compound of Formula I, Ia, and/or Ib, or a pharmaceutically acceptable salt thereof. Further, the present invention provides a method of treating Multiple Sclerosis, comprising administering to a patient in need thereof an effective amount of a compound of Formula I, Ia, and/or Ib, or a pharmaceutically acceptable salt thereof. Further, the present invention provides a method of treating Systemic Lupus Erythematosus, comprising administering to a patient in need thereof an effective amount of a compound of Formula I, Ia, and/or Ib, or a pharmaceutically acceptable salt thereof. Further, the present invention provides a method of treating Sjögren's Syndrome, comprising administering to a patient in need thereof an effective amount of a compound of Formula I, Ia, and/or Ib, or a pharmaceutically acceptable salt thereof. Further, the present invention provides a method of treating Pemphigus, comprising administering to a patient in need thereof an effective amount of a compound of Formula I, Ia, and/or Ib, or a pharmaceutically acceptable salt thereof.

The present invention provides a method of treating Rheumatoid Arthritis comprising administrating to a patient in need thereof an effective amount of 1-[(3S)-3-[[5-[2-[3-(difluoromethoxy)phenoxy]pyrimidin-5-yl]-3-pyridyl]amino]pyrrolidin-1-yl]prop-2-en-1-one, or a pharmaceutically acceptable salt thereof. The present invention provides a method of treating Multiple Sclerosis comprising administrating to a patient in need thereof an effective amount of 1-[(3S)-3-[[5-[2-[3-(difluoromethoxy)phenoxy]pyrimidin-5-yl]-3-pyridyl]amino]pyrrolidin-1-yl]prop-2-en-1-one, or a pharmaceutically acceptable salt thereof. The present invention provides a method of treating Systemic Lupus Erythematosus comprising administrating to a patient in need thereof an effective amount of 1-[(3S)-3-[[5-[2-[3-(difluoromethoxy)phenoxy]pyrimidin-5-yl]-3-pyridyl]amino]pyrrolidin-1-yl]prop-2-en-1-one, or a pharmaceutically acceptable salt thereof. The present invention provides a method of treating Sjögren's Syndrome comprising administrating to a patient in need thereof an effective amount of 1-[(3S)-3-[[5-[2-[3-(difluoromethoxy)phenoxy]pyrimidin-5-yl]-3-pyridyl]amino]pyrrolidin-1-yl]prop-2-en-1-one, or a pharmaceutically acceptable salt thereof. The present invention provides a method of treating Pemphigus comprising administrating to a patient in need thereof an effective amount of 1-[(3S)-3-[[5-[2-[3-(difluoromethoxy)phenoxy]pyrimidin-5-yl]-3-pyridyl]amino]pyrrolidin-1-yl]prop-2-en-1-one, or a pharmaceutically acceptable salt thereof.

The term "pharmaceutically acceptable salt" includes an acid addition salt that exists in conjunction with the basic portion of a compound of Formula I, Ia, and/or Ib. Such salts include the pharmaceutically acceptable salts, for example those listed in Handbook of Pharmaceutical Salts: Properties, Selection and Use, P. H. Stahl and C. G. Wermuth (Eds.), Wiley-VCH, New York, 2002 which are known to the skilled artisan.

In addition to pharmaceutically acceptable salts, other salts are contemplated in the invention. They may serve as intermediates in the purification of compounds or in the preparation of other pharmaceutically-acceptable salts, or are useful for identification, characterization or purification of compounds of the invention.

As used herein, the term "patient" refers to a warm blooded animal such as a mammal and includes a human. A human is a preferred patient. In certain embodiments, the patient is further characterized as suffering from an autoimmune or inflammatory disease that would benefit from decreased activity of BTK. An autoimmune or inflammatory disease that are expected to benefit from decreased activity of BTK include RA, MS, Lupus and in particular SLE, MS including relapsing remitting Multiple Sclerosis (RRMS) and primary progressive Multiple Sclerosis (PPMS), Sjögren's Syndrome, and Pemphigus including Pemphigus vulgaris.

One skilled in the art may treat an autoimmune or inflammatory disease by administering to a patient presently displaying symptoms an effective amount of the compound of Formula I, Ia, and/or Ib. Thus as used herein, the terms "treatment" and/or "treating" are intended to refer to all processes wherein there may be a slowing, interrupting, arresting, controlling, or stopping of the progression of an existing disorder and/or symptoms thereof, but does not necessarily indicate a total elimination of all disorder symptoms. Treatment includes administration of a compound of the present invention for treatment of an autoimmune or inflammatory disease or condition in a mammal, particularly in a human, that would benefit from a decreased level of BTK activity, and includes: (a) inhibiting further progression of the disease, i.e., arresting its development; and (b) relieving the disease, i.e., causing regression of the disease or disorder or alleviating symptoms or complications thereof.

As used herein, the term "effective amount" of a compound of Formula I, Ia, and/or Ib, refers to an amount which is effective in treating a disorder, such as an autoimmune or inflammatory disease described herein. In determining an effective amount or dose of a compound of Formula I, Ia, and/or Ib, a number of factors are considered, including, which compound of Formula I, Ia, and/or Ib, is administered; whether co-administration of other agents exists; the species of mammal; its size, age, and general health; the degree of involvement or the severity of the disorder, such as an autoimmune or inflammatory; the response of the individual patient; the mode of administration; the bioavailability characteristics of the preparation administered; the dose regimen selected; and other relevant circumstances.

The compounds of the present invention can be administered alone or in the form of a pharmaceutical composition combined with pharmaceutically acceptable carriers or excipients, the proportion, and nature of which are determined by the solubility and chemical properties, including stability, of the compound selected, the chosen route of administration, and standard pharmaceutical practice. The compounds of the present invention, while effective themselves, may also be formulated and administered in the form of their pharmaceutically acceptable salts. Preferred pharmaceutical compositions can be formulated as a tablet, capsule, solution for oral administration, or solution for injection. The tablet, capsule, or solution can include a compound of the present invention in an amount effective for treating a patient in need of treatment. One skilled in the art of preparing formulations can readily select the proper form and mode of administration depending upon the particular characteristics of the compound selected, the disorder or condition to be treated, the stage of the disorder or condition, and other relevant circumstances (See, e.g., Remington: The Science and Practice of Pharmacy, L. V. Allen, Editor, 22$^{nd}$ Edition, Pharmaceutical Press, 2012).

Certain abbreviations are defined as follows: "AcOH" refers to acetic acid; "Ac" refers to acetyl; "ACN" refers to acetonitrile; "Bn" refers to benzyl;" "BOC" refers to tert-butylcarbonyloxy; "BTK" refers to Bruton's tyrosine kinase; "n-BuLi" refers to n-butyllithium; "sec-BuLi" refers to sec-butyllithium; "Bz" refers to carbobenzyloxy; "CIA" refers to collagen-induced arthritis; "DCM" refers to dichloromethane or methylene chloride; "DIPEA" refers to N,N-diisopropylethylamine; "DMF" refers to N,N-dimethylformamide; "DMA" refers to dimethylacetamide; "DMSO" refers to dimethylsulfoxide; "DTT" refers to dithiothreitol; "EDTA" refers to ethylenediamine tetacetate; "EGFR" refers to epidermal growth factor receptor; "EGTA" refers to ethylene glycol-bis(β-aminoethyl ether)-N,N,N',N'-tetraacetic acid; "Et$_2$O" refers to ethyl ether or diethyl ether; "EtOAc" refers to ethyl acetate; "EtOH" refers to ethanol; "FACS buffer" refers to phosphate-buffered saline (PBS), 2% calf serum, 1 mM EDTA, and 0.1% sodium azide, "h" refers to hour or hours; "GST" refers to glutathione S-transferase; "HEC" refers to hydroxyethyl cellulose; "HEPES" refers to 4-(2-hydroxyethyl)-1-piperazineethanesulfonic acid; "HWB" refers to human whole blood; "IC$_{50}$" refers to the concentration of an agent that produces 50% of the maximal inhibitory response; "LC-ES/MS" refers to Liquid Chromatography Electrospray Mass Spectrometry; "LDA" refers to lithium diisopropylamide; "min" refers to minute or minutes; "Me" refers to methyl; "MeOH" refers to methanol or methyl alcohol; "MTBE" refers to methyl-tert-butyl ether; "NMP" refers to N-methylpyrrolidinone or 1-methylpyrrolidinone; "OAc" refers to acetyloxy; "$^{33}$P" refers to phosphorus-33; "P80" refers to polysorbate-80 surfactant; "Prep." refers to preparation. "PO" refers to oral administration; "psi" refers to pounds per square inch; "RT" refers to room temperature; "TEA" refers to triethylamine; "TFA" refers to trifluoroacetic acid; "THF" refers to tetrahydrofuran. "HATU" refers to N-[(dimethylamino)-1H-1,2,3-triazolo-[4,5-b]pyridin-1-ylmethylene]-N-methylmethanaminium hexafluorophosphate N-oxide; "XPhos Palladacycle Gen 2" refers to chloro(2-dicyclohexylphosphino-2',4',6'-triisopropyl-1,1'-biphenyl)[2-(2'-amino-1,1'-biphenyl)]palladium(II). Isomer 1 refers to the first enantiomer to elute from a chromatograhphic purification under the conditions provided.

$R^{4'}$ may be selected from:

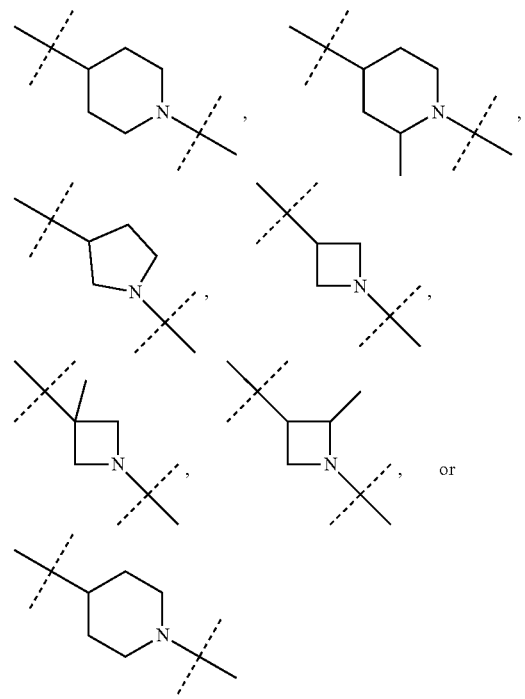

Scheme 1 depicts the amination of 3-bromo-5-iodopyridine (I). As is well-documented in the literature, a variety of conditions may be used to effect this coupling, generally involving a transition metal catalyst and an appropriate ligand complex, such as copper (Ullmann coupling) with the presence of a mild base, or palladium (Buchwald-Hartwig cross-coupling reaction). A suitably protected additional amine moiety (selected from among $R^{4'}$ described above) may be present in the amine substrate involved in the cross-coupling, wherein the protecting group (PG) may be removed and later functionalized in subsequent steps. Suitable protecting groups include, but are not limited to, BOC, Bz, Bn, Me, trityl, or acetyl. More specifically, about 1 equivalent of an appropriately substituted amine containing an additionally protected amino moiety (II) may be heated with about 0.75-1 equivalent 3-bromo-5-iodopyridine in the presence of about 0.1-0.25 equivalents of a copper(I) source, e.g., copper(I) bromide, and about 0.1-0.25 equivalents of a suitable ligand complex, e.g., BINOL or 1,1'-bi-2-naphthol, in a suitable polar solvent, such as DMF or DMSO, containing about 1.25-1.5 equivalents of a suitable base, such as potassium phosphate or sodium carbonate, to obtain the protected N-arylated amine product (III).

Scheme 1

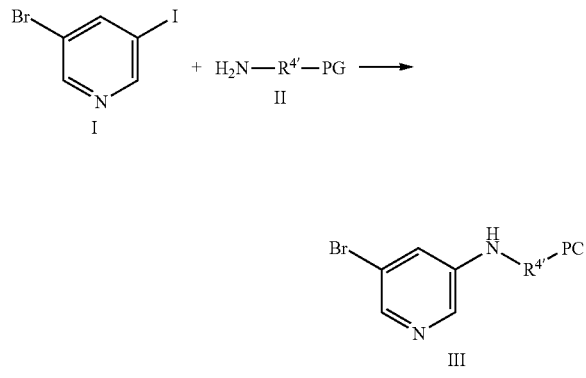

Scheme 2

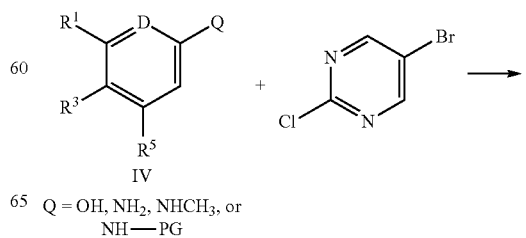

Q = OH, NH$_2$, NHCH$_3$, or NH—PG

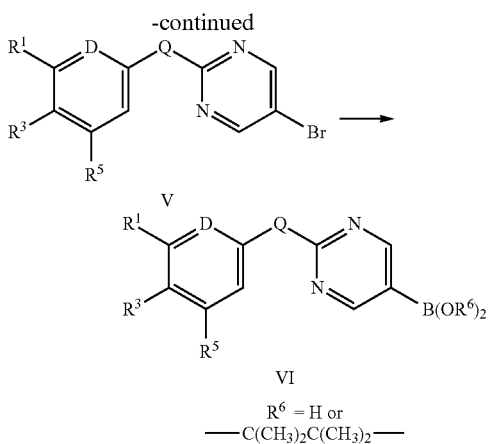

V

R⁶ = H or
—C(CH₃)₂C(CH₃)₂—

VI

Scheme 2 depicts the preparation of 2-oxo-and 2-aminopyrimidin-5-yl boronic acids and esters (VI). Generally, in the S$_n$Ar reaction, as is well known to a skilled artisan, an appropriately substituted or polysubstituted phenol (IV; D=CR², wherein R² is selected from H, F, or OCF₃; Q=OH; R¹, R³, R⁵=H, Cl, Br, F, CH, C$_{1-3}$ alkyl, C$_{1-3}$ alkoxy, CN, OCF₃, OCF₂H), a substituted or polysubstituted aniline (IV; aminopyridine D=CR², wherein R² is selected from H, F, or OCF₃; Q=OH; R¹, R³, R⁵=H, Cl, Br, F, CH, C$_{1-3}$ alkyl, C$_{1-3}$ alkoxy, CN, OCF₃, OCF₂H), a substituted or polysubstituted 2-aminopyridine (IV; D=N; Q=NH₂; R³, R⁵=H, Cl, Br, F, CH, C$_{1-3}$ alkyl, C$_{1-3}$ alkoxy, CN, OCF₃, OCF₂H), or an N-substituted aminopyridine (IV; D=N; Q=NHCH₃ or, e.g., NH-PG, wherein the PG is a protecting group suitable for easy removal as well described in the art), may be coupled to 5-bromo-2-chloropyrimidine, with or without an inorganic or non-nucleophilic base, to provide an appropriately substituted or polysubstituted 2-phenoxy-5-bromopyrimidine (V; D=CR², wherein R² is selected from H, F, or OCF₃; Q=O; R¹, R³, R⁵=H, Cl, Br, F, CH, C$_{1-3}$ alkyl, C$_{1-3}$ alkoxy, CN, OCF₃, OCF₂H), an appropriately substituted or polysubstituted 2-aminophenyl-5-bromopyrimidine (V; D=CR², wherein R² is selected from H, F, or OCF₃; Q=N; R¹, R³, R⁵=H, Cl, Br, F, CH, C$_{1-3}$ alkyl, C$_{1-3}$ alkoxy, CN, OCF₃, OCF₂H), or an appropriately substituted or polysubstituted 2-aminopyridyl-5-bromopyrimidine (V, D=N; Q=NH, R¹, R³, R⁵=H, Cl, Br, F, CH, C$_{1-3}$ alkyl, C$_{1-3}$ alkoxy, CN, OCF₃, OCF₂H), respectively. More specifically, about 1.0-1.25 equivalents of an appropriately substituted or polysubstituted phenol may be heated, to approximately 100° C., together with about 1 equivalent of 5-bromo-2-chloropyrimidine and about 2.5 or more equivalents of a suitable base such as K₂CO₃, in a suitable polar organic solvent, e.g., DMF, to obtain the 2-(substituted or polysubstituted)phenoxy-5-bromopyrimidine compound (V; D=CR², wherein R² is selected from H, F, or OCF₃; Q=O; R¹, R³, R⁵=H, Cl, Br, F, CH, C$_{1-3}$ alkyl, C$_{1-3}$ alkoxy, CN, OCF₃, OCF₂H). More specifically, about 1 equivalent of a substituted or polysubstituted aniline or 2-aminopyridine and about 1 equivalent of 5-bromo-2-chloropyrimidine may be heated together at a suitable temperature in a suitable polar organic solvent, e.g., NMP, under microwave conditions, to afford the 2-(substituted or polysubstituted)anilino-5-bromopyrimidine compound (V; D=CR², wherein R² is selected from H, F, or OCF₃; Q=NH; R¹, R³, R⁵=H, Cl, Br, F, CH, C$_{1-3}$ alkyl, C$_{1-3}$ alkoxy, CN, OCF₃, OCF₂H) or the 2-(substituted or polysubstituted)aminopyridyl-5-bromopyrimidine compound (V; D=N; Q=NH, R¹, R³, R⁵=H, Cl, Br, F, CH, C$_{1-3}$ alkyl, C$_{1-3}$ alkoxy, CN, OCF₃, OCF₂H), respectively.

Conversion of the aryl bromide to either the boronic acid (R⁶=H) or boronate ester [R⁶=—C(CH₃)₂C(CH₃)₂—] is well-appreciated in the art. The boronic acid VI (R⁶=H), may be prepared from compound of type V, for example, in a suitable polar organic solvent or solvent mixture, e.g., THF/toluene, by lithium-halogen exchange using n-BuLi, sec-BuLi, or LDA, at low temperature, with quenching of the in situ-generated aryllithium species with a trialkylborate. Subsequent hydrolysis in a suitable alcoholic solvent may yield the boronic acid. More specifically, about 1 equivalent of an appropriately substituted 2-phenoxy-5-bromopyrimidine may be dissolved in about a 4:1 mixture of toluene:THF and cooled to about −70° C. About 1.2-1.6 equivalents triisopropylborate may be added dropwise, with subsequent slow addition of about 1.3-1.6 equivalents of n-BuLi at −70° C. Addition of excess MeOH, subsequent to warming to RT, and addition of water with pH adjustment for acidification may yield the appropriately substituted 2-phenoxy-pyrimidin-5-yl boronic acid (VI; D=CR² as described above; Q=O; R¹, R³, R⁵=H, Cl, Br, F, CH, C$_{1-3}$ alkyl, C$_{1-3}$ alkoxy, CN, OCF₃, OCF₂H; R⁶=H). Additionally, the pinacol boronic ester may be prepared via a transition metal-mediated coupling reaction, as is well described in the art. More specifically, about 1 equivalent of an appropriate 2-mono- or polysubstituted phenoxy- or anilino-5-bromopyrimidine (V; D=CR² as described above; Q=O or N; R³, R⁵=H, Cl, Br, F, CH, C$_{1-3}$ alkyl, C$_{1-3}$ alkoxy, CN, OCF₃, OCF₂H), or 2-mono- or polysubstituted aminopyridyl-5-bromopyrimidine (V; D=N; Q=NH, R¹, R³, R⁵=H, Cl, Br, F, CH, C$_{1-3}$ alkyl, C$_{1-3}$ alkoxy, CN, OCF₃, OCF₂H), may be treated with about 1.2 equivalents of bis (pinacolato)diboron in the presence of about 0.1-0.2 equivalents of a palladium-ligand complex, e.g., tetrakis (triphenylphosphine) palladium(0) or 1,1'-bis (diphenylphosphino)ferrocene-palladium(II) dichloride—DCM complex, and a mild base, e.g., KOAc, NaOAc, or K₂CO₃, in a polar organic solvent, e.g., Et₂O, THF, DMF, or 1,4-dioxane, under an argon or nitrogen atmosphere with heating to provide the corresponding 2-mono- or polysubstituted phenoxy- or anilino-5-(4,4,5,5-tetramethyl-1,3,2-dioxaborolan-2-yl)pyrimidine (VI; D=CR² as described above; Q=O or NH; R¹, R³, R⁵=H, Cl, Br, F, CH, C$_{1-3}$ alkyl, C$_{1-3}$ alkoxy, CN, OCF₃, OCF₂H; R⁶=—C(CH₃)₂C(CH₃)₂—) or the corresponding 2-mono- or polysubstituted aminopyridyl-5-(4,4,5,5-tetramethyl-1,3,2-dioxaborolan-2-yl)pyrimidine (VI; D=N; Q=NH, R¹, R³, R⁵=H, Cl, Br, F, CH, C$_{1-3}$ alkyl, C$_{1-3}$ alkoxy, CN, OCF₃, OCF₂H), respectively.

Scheme 3

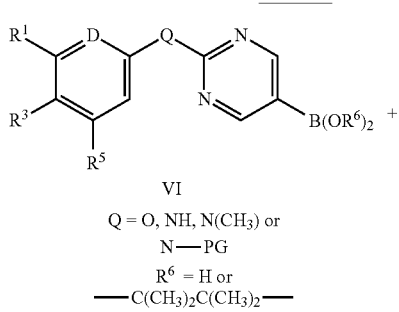

VI

Q = O, NH, N(CH₃) or
N—PG

R⁶ = H or
—C(CH₃)₂C(CH₃)₂—

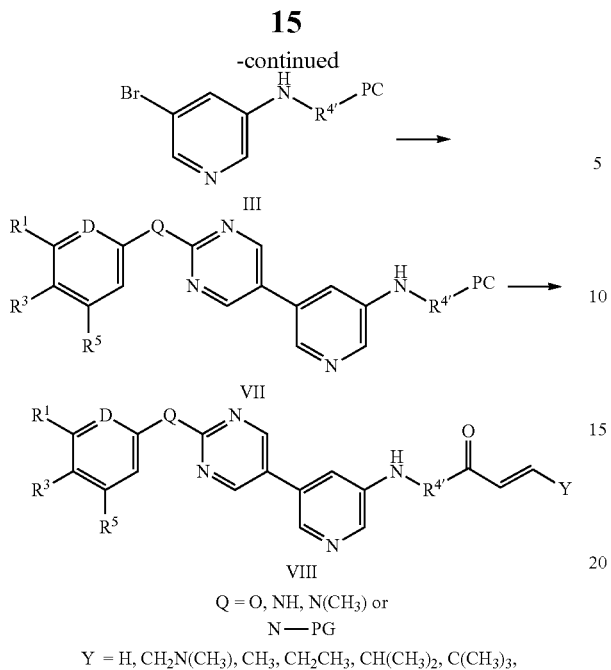

Q = O, NH, N(CH$_3$) or
N—PG

Y = H, CH$_2$N(CH$_3$), CH$_3$, CH$_2$CH$_3$, CH(CH$_3$)$_2$, C(CH$_3$)$_3$,

Scheme 3 depicts the preparation of compounds of type VIII (with R$^{4'}$ chosen from among the groups listed above), which may be prepared via a transition metal-mediated cross coupling, as well-described in the art, of the appropriately 3-substituted 5-bromopridine III (with PG as described in Scheme 1) and the appropriately 2-substituted pyrimidin-2-yl boronic acid or boronic ester, to obtain the amino-protected intermediate VII (with PG as described in Scheme 1; D, R$^1$, R$^3$, R$^5$, and Q as described in Scheme 2), with subsequent deprotection and acylation. More specifically, about 1 equivalent of the appropriately substituted 3-substituted 5-bromopridine (III) may be heated under microwave irradiation with about 1-1.2 equivalents of the appropriate boronic acid or boronic ester (VI, R=H or —C(CH$_3$)$_2$ (CH$_3$)$_2$C—) and about 0.05-0.1 equivalents of a palladium-ligand complex, e.g., tetrakis(triphenylphosphine) palladium(0) or 1,1'-bis(diphenylphosphino)ferrocene-palladium (II) dichloride—DCM complex, in the presence of a suitable mild base, e.g., KOAc, CsCO$_3$, CsF, or NaHCO$_3$, and a mixture of a water and a suitable polar organic solvent, e.g., THF or 1,4-dioxane, to obtain the compounds of type VII (with PG as described in Scheme 1 and D, R$^1$, R$^3$, R$^5$, and Q as described in Scheme 2). Subsequent deprotection of the protecting group may be accomplished under a wide array of conditions appropriate for said protecting group and is well-appreciated in the art. More specifically, about 1 equivalent of an appropriately substituted compound of type VII, wherein PG=BOC, may be treated with an excess of an appropriate acid, e.g., HCl or TFA, in a suitable organic solvent, e.g., DCM, EtOAc, or THF, to provide the crude deprotected amine. Subsequent in situ acylation with acryloyl chloride or a suitably substituted acryloyl chloride may be accomplished in the presence of a suitable non-nucleophilic organic base, e.g., DIPEA or TEA, in a suitable organic solvent, such as DCM or THF, at about RT to −78° C., to obtain compounds of type VIII (with D, R$^1$, R$^3$, R$^5$, and Q as described in Scheme 2). More specifically, about 1 equivalent of the previously described crude deprotected amine may be dissolved in DCM in the presence of excess DIPEA, cooled to −78° C., and treated dropwise with about 1-1.1 equivalents acyloyl chloride dissolved in DCM, to obtain the desired compound of type VIII (Q=O or NH; R$^1$, R$^3$, R$^5$=H, Cl, Br, F, CH, C$_{1-3}$ alkyl, C$_{1-3}$ alkoxy, CN, OCF$_3$, OCF$_2$H; Y=H, CH$_2$N(CH$_3$)$_2$, CH$_3$, CH$_2$CH$_3$, CH(CH$_3$)$_2$, C(CH$_3$)$_3$).

Scheme 4

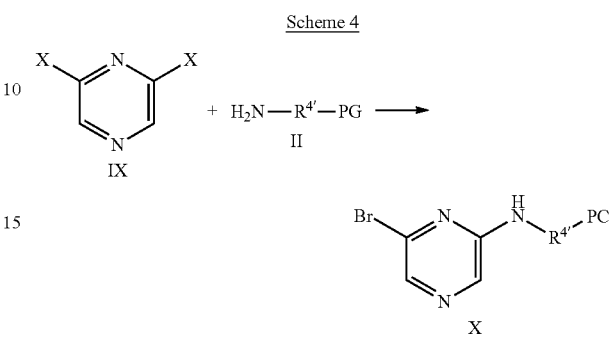

Scheme 4 depicts the amination of 2,3-dihalopyrazine (IX; X=Cl, Br, I). As is well-documented in the literature, a variety of conditions, similar to those described in Scheme 1, may be used to effect this coupling, generally involving S$_N$Ar-type displacement of the 2-halogen of a 2,6-dihalopyrazine, or a transition metal catalyst and an appropriate ligand complex, such as copper (Ullmann coupling) with the presence of a mild base, or palladium (Buchwald-Hartwig cross-coupling reaction). A suitably protected additional amine moiety (selected from among the protected R4' groups as described in Scheme 1) may be present in the amine substrate involved in the displacement or cross-coupling, wherein the protecting group (PG) may be removed and later functionalized in subsequent steps. Suitable protecting groups include, but are not limited to, BOC, Bz, Bn, Me, trityl, or acetyl. More specifically, about 1 equivalent of an appropriately substituted and mono-protected diamine (II) may be heated with about 0.75-1 equivalent 2,6-dibromopyrazine in the presence of about 1.25-1.5 equivalents of a non-nucleophilic amine, such as TEA, in a suitable polar solvent, such as DMF or DMSO, with heating at about 90° C. for about 4-18 h, to obtain the protected N-arylated amine product (X).

Scheme 5

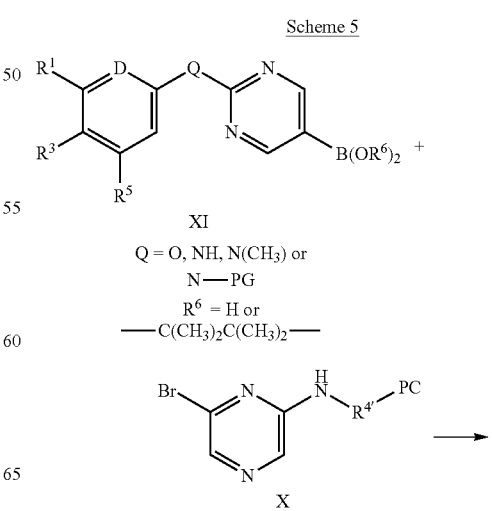

Q = O, NH, N(CH$_3$) or
N—PG
R$^6$ = H or
—C(CH$_3$)$_2$C(CH$_3$)$_2$—

-continued

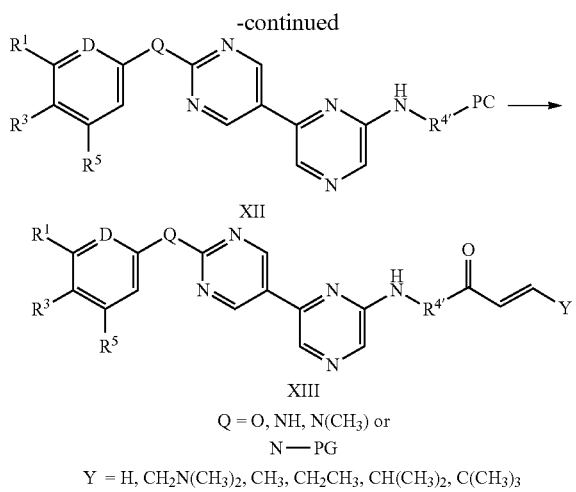

Q = O, NH, N(CH₃) or N—PG

Y = H, CH₂N(CH₃)₂, CH₃, CH₂CH₃, CH(CH₃)₂, C(CH₃)₃

Scheme 5 depicts the preparation of compounds of type VIII, which may be prepared under similar conditions described in Scheme 3, particularly, via a transition metal-mediated cross coupling, as well-described in the art, of the appropriately 2-substituted 5-halopyrazine X (with PG as described in Scheme 4) and the appropriately 5-substituted pyrimidin-2-yl boronic acid or boronic ester XI (with D, $R^1$, $R^3$, $R^5$, and Q as described in Scheme 2), to obtain the amino-protected intermediate XII (with PG as described in Scheme 1; D, $R^1$, $R^3$, $R^5$, and Q as described in Scheme 2). Subsequent deprotection and acylation as described in Scheme 3 may be performed to obtain the desired compounds of type XII. More specifically, about 1 equivalent of the appropriately substituted 2-substituted 6-halopyrazine (X) may be heated under microwave irradiation with about 1-1.2 equivalents of the appropriate boronic acid or boronic ester XI and about 0.05-0.1 equivalents of a palladium-ligand complex, e.g., tetrakis(triphenylphosphine) palladium(0) or 1,1'-bis(diphenylphosphino)ferrocene-palladium (II) dichloride—DCM complex, in the presence of a suitable mild base, e.g., KOAc, CsCO₃, CsF, or NaHCO₃, and a mixture of a water and a suitable polar organic solvent, e.g., THF or 1,4-dioxane, to obtain the compounds of type XI (with PG as described in Scheme 4, and D, $R^1$, $R^3$, $R^5$, and Q as described in Scheme 2). Subsequent deprotection of the protecting group may be accomplished under a wide array of conditions appropriate for said protecting group and is well-appreciated in the art. More specifically, about 1 equivalent of an appropriately substituted compound of type XII, wherein PG=BOC, may be treated with an excess of an appropriate acid, e.g., HCl or TFA, in a suitable organic solvent, e.g., DCM, EtOAc, or THF, to provide the crude deprotected amine. Subsequent in situ acylation with acryloyl chloride or a suitably substituted acryloyl chloride may be accomplished in the presence of a suitable non-nucleophilic organic base, e.g., DIPEA or TEA, in a suitable organic solvent, such as DCM or THF, at about RT to −78° C., to obtain compounds of type XIII (with D, $R^1$, $R^3$, $R^5$, and Q as described in Scheme 2). More specifically, about 1 equivalent of the previously described crude deprotected amine may be dissolved in DCM in the presence of excess DIPEA, cooled to −78° C., and treated dropwise with about 1-1.1 equivalents of the appropriately substituted acryloyl chloride dissolved in DCM, to obtain the desired compound of type XIII (D=$CR^2$ or N, wherein $R^2$ is as described in Scheme 2; Q=O or NH; $R^{4'}$ selected from the group described in Scheme 1; $R^1$, $R^3$, $R^5$=H, Cl, Br, F, CH, $C_{1-3}$ alkyl, $C_{1-3}$ alkoxy, CN, OCF₃, OCF₂H; Y=H, CH₂N(CH₃)₂, CH₃, CH₂CH₃, CH(CH₃)₂, C(CH₃)₃).

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

LC-ES/MS is performed on an AGILENT® HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C18 2.1×50 mm 3.5 µm; gradient: 5-100% B in 3 min, then 100% B for 0.75 min, or 5-95% B in 1.5 min, then 95% B for 0.25 min; column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: XTERRA® MS C18 columns 2.1×50 mm, 3.5 µm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min or 5-95% B in 1.5 min, then 95% B for 0.25 min; column temperature: 50° C.+/−10° C.; flow rate: 1.2 mL/min; Solvent A: 10 mM NH₄HCO₃ pH 9; Solvent B: ACN; wavelength: 214 nm.

NMR spectra are performed on a Bruker AVIII HD 400 MHz NMR Spectrometer or a Varian VNMRS 300 or 400 MHz NMR Spectrometer, obtained as CDCl₃ or DMSO-d₆ solutions reported in ppm, using residual solvent [CDCl₃, 7.26 ppm; DMSO-d₆, 2.05 ppm] as reference standard. When peak multiplicities are reported, the following abbreviations may be used: s (singlet), d (doublet), t (triplet), q (quartet), m (multiplet), br s (broad singlet), dd (doublet of doublets), dt (doublet of triplets). Coupling constants (J), when reported, are reported in hertz (Hz).

Preparation 1 tert-butyl 4-[(5-bromo-3-pyridyl)amino]piperidine-1-carboxylate

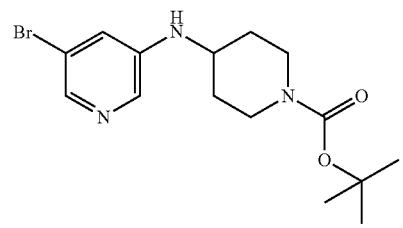 [SMILES: CC(C)(C)OC(=O)N1CCC(Nc2cncc(Br)c2)CC1]

A dry 20 mL reaction vial is charged with 3-bromo-5-iodopyridine (2.0 g, 6.9 mmol), tert-butyl 4-aminopiperidine-1-carboxylate (1.8 g, 9.0 mmol), copper(I) bromide (0.2 g, 1.4 mmol), 1,1'-bi-2-naphthol (0.4 g, 1.4 mmol), K₃PO₄ (2.9 g, 13.8 mmol), and DMF (6.5 g, 6.9 mL). Dry nitrogen is bubbled subsurface for 5 minutes. The vial is sealed and heated to 85° C. for a total of 3 h and then cooled to RT. The mixture is diluted with EtOAc and the mixture filtered over diatomaceous earth and a pad of silica gel. The filtrate is washed with saturated aqueous NaCl, dried over MgSO$_4$, and concentrated under reduced pressure. The resulting residue is purified by silica gel flash column chromatography, using a gradient of 40 to 100% EtOac in hexanes, to yield the title compound (1.6 g, 65% yield). ES/MS m/z ($^{79}$Br/$^{81}$Br) 356.0/358.0 [M+H].

The following compounds are prepared essentially by the method of Preparation 1, using 3-bromo-5-iodonvridine and an appropriately substituted amine.

reduced pressure and is dissolved in acetone (14 mL). The resulting suspension is cooled to 0° C. and a solution of potassium peroxymonosulfate (3.1 g, 5.0 mmol) in water (13.8 mL) is added over 10 min. After stirring for 2 h while maintaining the temperature at 0° C., the reaction mixture is diluted with water (40 mL), and the mixture is extracted with EtOAc (3×40 mL). The resulting layers are separated, and the combined organic layers are washed with saturated aqueous NaCl, dried over Na$_2$SO$_4$, filtered and concentrated under reduced pressure. The resulting residue is purified by silica gel flash column chromatography, using a gradient of

| Prep. | Structure | Name | MS ES/MS m/z ($^{79}$Br/$^{81}$Br) [M + H] |
|---|---|---|---|
| 2 | 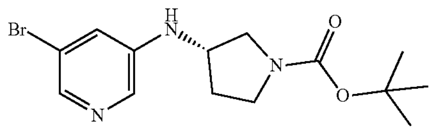 [SMILES: CC(C)(C)OC(=O)N1CC[C@H](Nc2cncc(Br)c2)C1] | tert-butyl (3S)-3-[(5-bromo-3-pyridyl)amino]pyrrolidine-1-carboxylate | 342.0/344.0 |
| 3 | 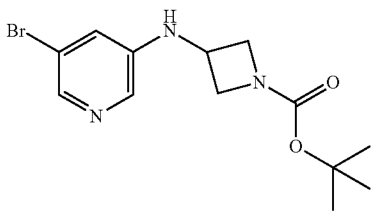 [SMILES: CC(C)(C)OC(=O)N1CC(Nc2cncc(Br)c2)C1] | tert-butyl 3-[(5-bromo-3-pyridyl)amino]azetidine-1-carboxylate | 328.0/330.0 |
| 4 | 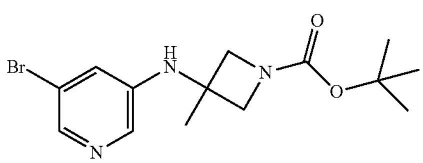 [SMILES: CC1(Nc2cncc(Br)c2)CN(C(=O)OC(C)(C)C)C1] | tert-butyl 3-[(5-bromo-3-pyridyl)amino]-3-methyl-azetidine-1-carboxylate | 342.0/344.0 |
| 5 | 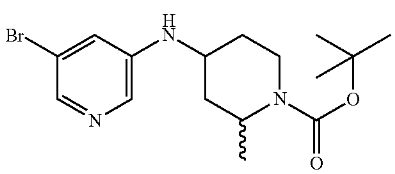 [SMILES: CC1CC(Nc2cncc(Br)c2)CCN1C(=O)OC(C)(C)C] | tert-butyl 4-((5-bromopyridin-3-yl)amino)-2-methylpiperidine-1-carboxylate | 370.1/372.1 |

Preparation 6

3-(difluoromethoxy)-4-fluoro-phenol

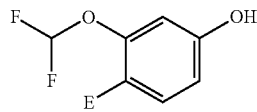

5-bromo-2-fluoro-1-difluoromethoxybenzene (1.0 g, 4.1 mmol), bis(pinacolato)diboron (1.3 g, 5.0 mmol), 1,1-bis(diphenylphosphino)ferrocene-palladium(II) dichloride dichloromethane complex (0.3 g, 0.4 mmol), KOAc (0.8 g, 8.3 mmol), and anhydrous 1,4-dioxane (8.3 mL) are added to a pressure vessel. Argon is bubbled through the solution for several minutes. The vessel is sealed and is heated at 85° C. overnight. After cooling to RT, the reaction mixture is diluted with EtOAc and filtered through diatomaceous earth. The filtrate is concentrated to crude blackish oil under 10-50% EtOAc in hexanes, to yield the title compound (0.77 g, quantitative yield) as a yellow oil. ES/MS m/z 176.8 [M–H].

Preparation 7

3-(2-triisopropylsilylethynyl)phenol

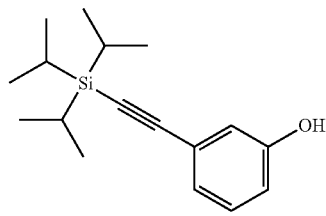 [SMILES: CC(C)[Si](C#Cc1cccc(O)c1)(C(C)C)C(C)C]

Argon gas is bubbled through a solution of 3-iodophenol (2.0 g, 8.9 mmol) in anhydrous THF (44 mL) and TEA (11 mL) for several minutes. Bis (triphenylphosphine)palladium (II) dichloride (0.25 g, 0.36 mmol), cuprous iodide (0.1 g, 0.5 mmol), and (triisopropylsilyl)acetylene (2.4 mL, 11.0 mmol) are added sequentially. The reaction mixture is stirred overnight at RT. The reaction mixture is diluted with Et$_2$O and the mixture is filtered through diatomaceous earth. The filtrate is concentrated under reduced pressure to a dark oil, which is purified by silica gel flash column chromatography, using 10% EtOAc in hexanes, to obtain the title compound (2.0 g, 98% yield). ES/MS m/z 273.2 [M−H].

Preparation 8

5-bromo-2-(3-chlorophenoxy)pyrimidine

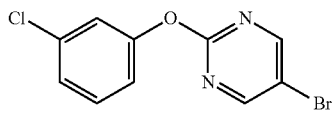 [SMILES: Clc1cccc(Oc2ncc(Br)cn2)c1]

3-Chlorophenol (6.0 g, 44.0 mmol), 5-bromo-2-chloropyrimidine (8.1 g, 40.9 mmol) and K$_2$CO$_3$ (45.0 g, 105.0 mmol) are suspended in DMF (30 mL). The resulting mixture is heated for 2 h at 100° C. The suspension is diluted with water and extracted several times with EtOAc. The resulting layers are separated, and the combined organic extracts are washed with saturated aqueous NaCl, dried over Na$_2$SO$_4$, filtered, and concentrated under reduced pressure. The crude residue is purified by silica gel flash column chromatography, using 100% DCM as the eluent, to obtain the title compound (11.0 g, 99% yield). ES/MS m/z ($^{79}$Br/$^{81}$Br) 284.8/286.8 [M+H].

The following compounds are prepared essentially by the method of Preparation 8, using 5-bromo-2-chloropyrimidine and an appropriately substituted phenol.

| Prep. | Structure | Name | ES/MS m/z ($^{79}$Br/$^{81}$Br) [M + H] |
|---|---|---|---|
| 9 | 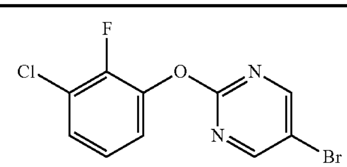 | 5-bromo-2-(3-chloro-2-fluoro-phenoxy)pyrimidine | ($^{35}$Cl$^{79}$Br/$^{37}$Cl$^{79}$Br, $^{35}$Cl$^{81}$Br/$^{37}$Cl$^{81}$Br) 302.8/304.8/306.8 |
| 10 | 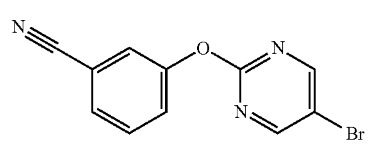 [SMILES: N#Cc1cccc(Oc2ncc(Br)cn2)c1] | 3-(5-bromopyrimidin-2-yl)oxybenzonitrile | 275.8/277.8 |
| 11 | 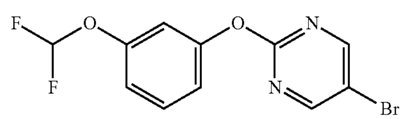 [SMILES: FC(F)Oc1cccc(Oc2ncc(Br)cn2)c1] | 5-bromo-2-[3-(difluoromethoxy)phenoxy]pyrimidine | 316.8/318.8 |
| 12 | 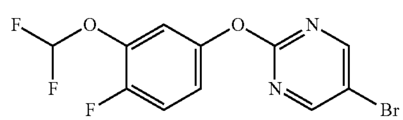 [SMILES: Fc1ccc(Oc2ncc(Br)cn2)cc1OC(F)F] | 5-bromo-2-[3-(difluoromethoxy)-4-fluoro-phenoxy]pyrimidine | 334.8/336.8 |
| 13 | 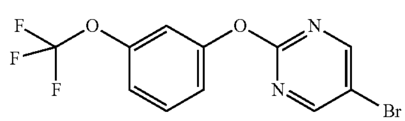 [SMILES: FC(F)(F)Oc1cccc(Oc2ncc(Br)cn2)c1] | 5-bromo-2-[3-(trifluoromethoxy)phenoxy]pyrimidine | 334.8/336.8 |
| 14 | 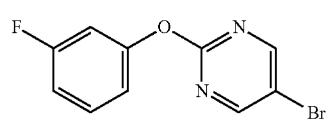 [SMILES: Fc1cccc(Oc2ncc(Br)cn2)c1] | 5-bromo-2-(3-fluorophenoxy)pyrimidine | 268.8/270.8 |
| 15 | 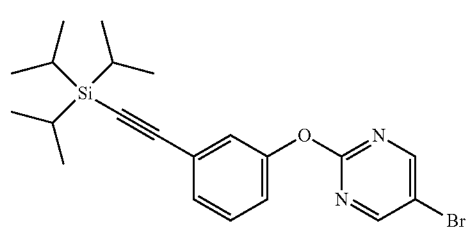 [SMILES: CC(C)[Si](C#Cc1cccc(Oc2ncc(Br)cn2)c1)(C(C)C)C(C)C] | 2-[3-(5-bromopyrimidin-2-yl)oxyphenyl]ethynyl-triisopropyl-silane | 431.0/433.0 |

-continued

| Prep. | Structure | Name | ES/MS m/z ($^{79}$Br/$^{81}$Br) [M + H] |
|---|---|---|---|
| 16 | 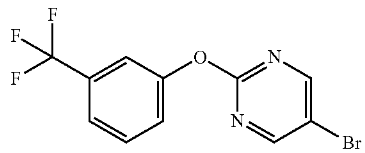 [SMILES: FC(F)(F)c1cccc(Oc2ncc(Br)cn2)c1] | 5-bromo-2-[3-(trifluoromethyl)phenoxy]pyrimidine | 318.8/320.8 |
| 17 | 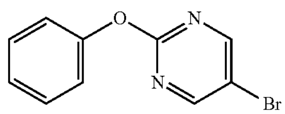 [SMILES: Brc1cnc(Oc2ccccc2)nc1] | 5-bromo-2-phenoxy-pyrimidine | 250.8/252.8 |
| 18 | 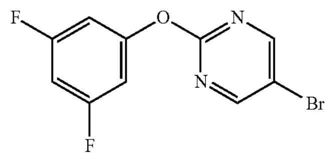 [SMILES: Fc1cc(F)cc(Oc2ncc(Br)cn2)c1] | 5-bromo-2-(3,5-difluorophenoxy)pyrimidine | 286.8/288.8 |
| 19 | 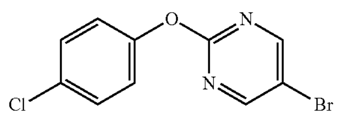 [SMILES: Clc1ccc(Oc2ncc(Br)cn2)cc1] | 5-bromo-2-(4-chlorophenoxy)pyrimidine | ($^{35}$Cl$^{79}$Br/$^{37}$Cl$^{79}$Br, $^{35}$Cl$^{81}$Br/$^{37}$Cl$^{81}$Br) 284.8/286.8/288.8 |
| 20 | 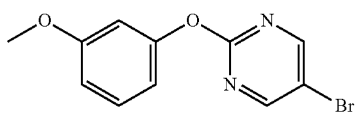 [SMILES: COc1cccc(Oc2ncc(Br)cn2)c1] | 5-bromo-2-(3-methoxyphenoxy)pyrimidine | 280.8/282.8 |

Preparation 21

5-bromo-N-[3-(trifluoromethyl)phenyl]pyrimidin-2-amine

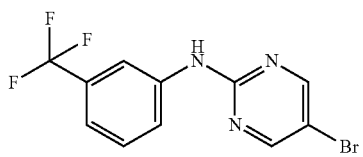 [SMILES: FC(F)(F)c1cccc(Nc2ncc(Br)cn2)c1]

3-Aminobenzotrifluoride (2.5 g, 16.0 mmol), 5-bromo-2-chloropyrimidine (3.1 g, 16.0 mmol) and NMP (8.0 g, 81 mmol) are added to a 20 mL microwave vial. The sealed vial is heated in a microwave for 1 hour at 150° C. The reaction mixture is transferred to a separatory funnel, diluted with EtOAc (150 mL), and is sequentially washed with 1N NaOH (3×50 mL) and saturated aqueous NaCl. The resulting layers are separated. The organic phase is dried over Na$_2$SO$_4$, filtered, and concentrated under reduced pressure to give a solid.

The crude material is purified by silica gel flash column chromatography, using 30% EtOAc in hexanes as eluant, to obtain the title compound (3.37 g, 67% yield) as a yellow solid. ES/MS m/z ($^{79}$Br/$^{81}$Br) m/z 317.9/319.9 [M+H].

The following compounds are prepared essentially by the method of Preparation 21, using 5-bromo-2-chloropyrimidine and an appropriately substituted aniline.

| Prep. | Structure | Name | MS ES/MS m/z ($^{79}$Br/$^{81}$Br) [M + H] |
|---|---|---|---|
| 22 | 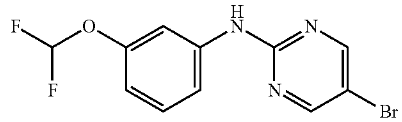 [SMILES: FC(F)Oc1cccc(Nc2ncc(Br)cn2)c1] | 5-bromo-N-[3-(difluoromethoxy)phenyl]pyrimidin-2-amine | 315.8/317.8 |
| 23 | 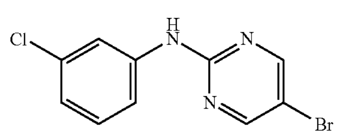 [SMILES: Clc1cccc(Nc2ncc(Br)cn2)c1] | 5-bromo-N-(3-chlorophenyl)pyrimidin-2-amine | ($^{35}$Cl$^{79}$Br/$^{37}$Cl$^{79}$Br, $^{35}$Cl$^{81}$Br/$^{37}$Cl$^{81}$Br) 283.8/285.8/287.8 |

| Prep. | Structure | Name | MS ES/MS m/z ($^{79}$Br/$^{81}$Br) [M + H] |
|---|---|---|---|
| 24 | 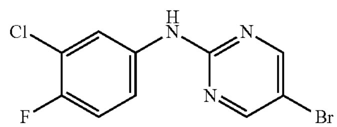 [SMILES: Fc1ccc(Nc2ncc(Br)cn2)cc1Cl] | 5-bromo-N-(3-chloro-4-fluoro-phenyl)pyrimidin-2-amine | ($^{35}$Cl$^{79}$Br/$^{37}$Cl$^{79}$Br, $^{35}$Cl$^{81}$Br/$^{37}$Cl$^{81}$Br) 301.8/303.8/305.8 |
| 25 | 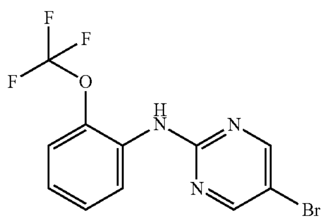 [SMILES: FC(F)(F)Oc1ccccc1Nc1ncc(Br)cn1] | 5-bromo-N-[2-(trifluoromethoxy)phenyl]pyrimidin-2-amine | 334.0/335.8 |
| 26 | 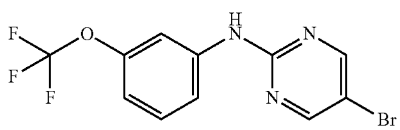 [SMILES: FC(F)(F)Oc1cccc(Nc2ncc(Br)cn2)c1] | 5-bromo-N-[3-(trifluoromethoxy)phenyl]pyrimidin-2-amine | 333.8/335.8 |

Preparation 27

2-[3-(difluoromethoxy)phenoxy]-5-(4,4,5,5-tetramethyl-1,3,2-dioxaborolan-2-yl)pyrimidine

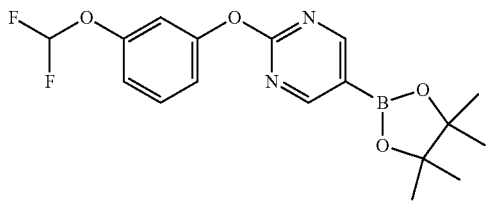 [SMILES: CC1(C)OB(c2cnc(Oc3cccc(OC(F)F)c3)nc2)OC1(C)C]

A pressure vial is charged with 5-bromo-2-[3-(difluoromethoxy)phenoxy]pyrimidine (3.1 g, 9.8 mmol), bis(pinacolato)diboron (3.0 g, 12 mmol), 1,1'-bis(diphenylphosphino)ferrocene-palladium(II) dichloride—DCM complex (0.8 g, 1.0 mmol), KOAc (2.0 g, 20.0 mmol), and anhydrous 1,4-dioxane (20 mL). Argon is bubbled subsurface for several minutes. The pressure vial is sealed and heated at 85° C. overnight. The cooled reaction mixture is diluted with EtAOc and filtered through diatomaceous earth. The filtrate is washed sequentially with water and saturated aqueous NaCl. The layers are separated and the organic extract is dried over Na$_2$SO$_4$, filtered, and concentrated under reduced pressure to obtain the title compound (5.4 g, 91% yield) as a dark solid at an assumed 60% purity. ES/MS m/z 365.0 [M+H].

The following compounds are prepared essentially by the method of Preparation 27, using bis(pinacolato)diboron and an appropriately 2-substituted 5-bromopyrimidine.

| Prep. | Structure | Name | ES/MS m/z |
|---|---|---|---|
| 28 | 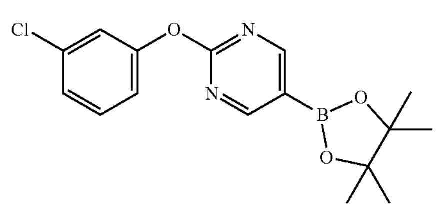 [SMILES: CC1(C)OB(c2cnc(Oc3cccc(Cl)c3)nc2)OC1(C)C] | 2-(3-chlorophenoxy)-5-(4,4,5,5-tetramethyl-1,3,2-dioxaborolan-2-yl)pyrimidine | ($^{35}$Cl/$^{37}$Cl) 333.0/335.0 [M + H]$^+$ |

-continued

| Prep. | Structure | Name | ES/MS m/z |
|---|---|---|---|
| 29 | 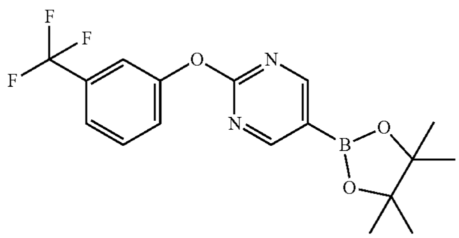 [SMILES: CC1(C)OB(c2cnc(Oc3cccc(C(F)(F)F)c3)nc2)OC1(C)C] | 5-(4,4,5,5-tetramethyl-1,3,2-dioxaborolan-2-yl)-2-[3-(trifluoromethyl)phenoxy]pyrimidine | 367.0 [M + H] |
| 30 | 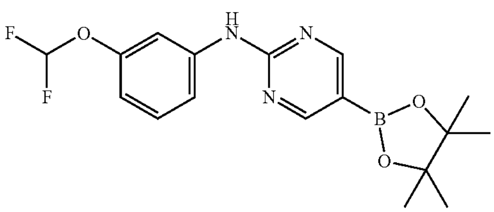 | N-[3-(difluoromethoxy)phenyl]-5-(4,4,5,5-tetramethyl-1,3,2-dioxaborolan-2-yl)pyrimidin-2-amine | 282.0 [M + H − $C_6H_{10}$] |
| 31 | 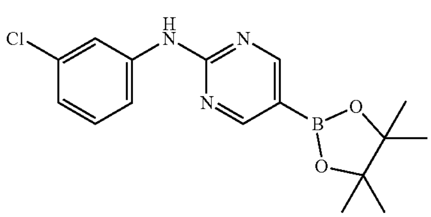 | N-(3-chlorophenyl)-5-(4,4,5,5-tetramethyl-1,3,2-dioxaborolan-2-yl)pyrimidin-2-amine | 250.0/252.0 [M + H − $C_6H_{10}$] |
| 32 | 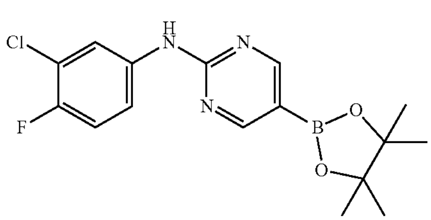 | N-(3-chloro-4-fluoro-phenyl)-5-(4,4,5,5-tetramethyl-1,3,2-dioxaborolan-2-yl)pyrimidin-2-amine | ($^{35}Cl/^{37}Cl$) 268.0/270.0 [M + H − $C_6H_{10}$] |

| Prep. | Structure | Name | ES/MS m/z |
|---|---|---|---|
| 33 | 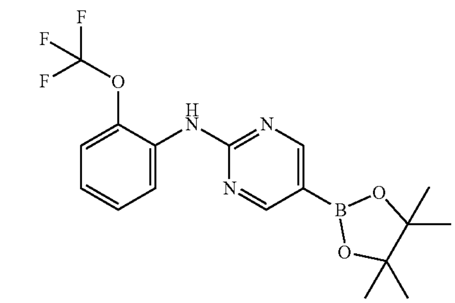 | 5-(4,4,5,5-tetramethyl-1,3,2-dioxaborolan-2-yl)-N-[2-(trifluoromethoxy)phenyl]pyrimidin-2-amine | 300.0 [M + H − $C_6H_{10}$] |
| 34 | 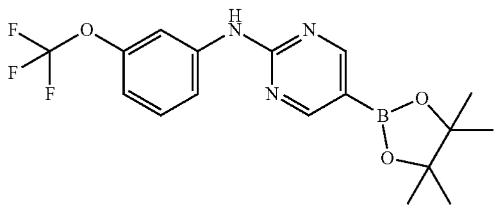 | 5-(4,4,5,5-tetramethyl-1,3,2-dioxaborolan-2-yl)-N-[3-(trifluoromethoxy)phenyl]pyrimidin-2-amine | 300.0 [M + H − $C_6H_{10}$] |

Preparation 35 tert-butyl 3-[[5-(4,4,5,5-tetramethyl-1,3,2-dioxaborolan-2-yl)-3-pyridyl]amino]azetidine-1-carboxylate

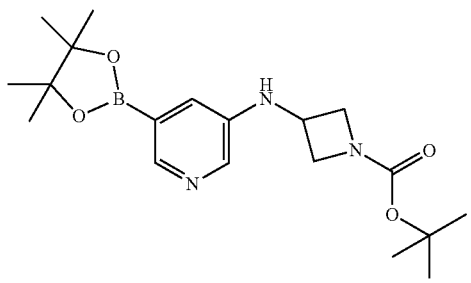 [SMILES: CC(C)(C)OC(=O)N1CC(Nc2cncc(B3OC(C)(C)C(C)(C)O3)c2)C1]

A pressure vial is charged with tert-butyl 3-[(5-bromo-3-pyridyl)amino]azetidine-1-carboxylate (2.6 g, 7.9 mmol), bis(pinacolato)diboron (2.5 g, 9.5 mmol), 1,1'-bis(diphenylphosphino)ferrocene-palladium(II) dichloride—DCM complex (0.7 g, 0.8 mmol), KOAc (1.6 g, 16.0 mmol), and anhydrous 1,4-dioxane (16 mL). Argon is bubbled subsurface for several minutes. The pressure vial is sealed and heated at 85° C. overnight. The reaction mixture is diluted with EtOAc and filtered through diatomaceous earth. The filtrate is concentrated under reduced pressure. The resulting residue is dissolved in EtOAc and water; the layers are separated. The organic layer is washed with saturated aqueous NaCl, dried over $Na_2SO_4$, filtered, and concentrated to obtain the title compound (3.1 g, 63% yield) as a brown foam of 60% purity. ES/MS m/z 294 (M+H−$C_6H_{10}$).

Preparation 36 tert-butyl 3-[[5-[2-[3-(2-triisopropylsilylethynyl)phenoxy]pyrimidin-5-yl]-3-pyridyl]amino]azetidine-1-carboxylate

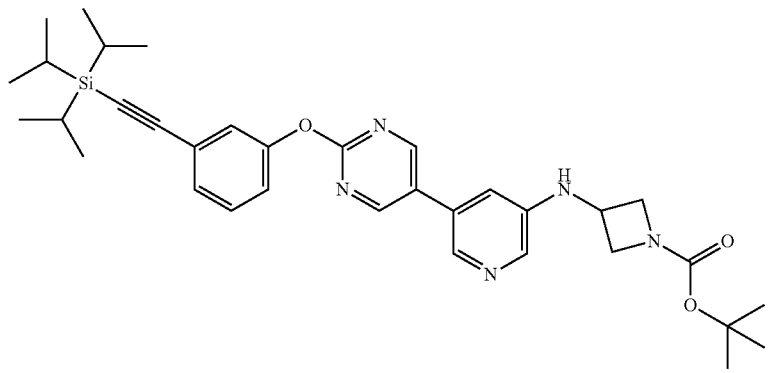 [SMILES: CC(C)[Si](C#Cc1cccc(Oc2ncc(-c3cncc(NC4CN(C(=O)OC(C)(C)C)C4)c3)cn2)c1)(C(C)C)C(C)C]

A microwave vial is charged with tert-butyl 3-[[5-(4,4,5,5-tetramethyl-1,3,2-dioxaborolan-2-yl)-3-pyridyl]amino]azetidine-1-carboxylate (0.6 g, 0.9 mmol), 2-[3-(5-bromopyrimidin-2-yl)oxyphenyl]ethynyl-triisopropylsilane (0.45 g, 1.0 mmol), 1,1'-bis(diphenylphosphino)ferrocene-palladium(II) dichloride—DCM complex (0.08 g, 0.09 mmol), Cs$_2$CO$_3$ (0.6 g, 1.9 mmol), 1,4-dioxane (3.1 mL) and water (0.9 mL). Argon is bubbled through the mixture for 2 minutes. The vial is sealed and heated in the microwave for 15 minutes at 120° C. The reaction mixture is diluted with EtOAc, filtered through diatomaceous earth, and concentrated under reduced pressure. The resulting residue is purified by flash column chromatography, using a gradient of 5% MeOH in EtOAc, to obtain the title compound (0.2 g, 36% yield) as oil. ES/MS m/z 600.4 [M+H]

The following compounds are prepared essentially by the method of Preparation 36, using tert-butyl 3-[[5-(4,4,5,5-tetramethyl-1,3,2-dioxaborolan-2-yl)-3-pyridyl]amino]azetidine-1-carboxylate and the appropriately substituted 5-bromopyrimidine.

| Prep. | Structure | Name | MS m/z [M + H] |
|---|---|---|---|
| 37 | 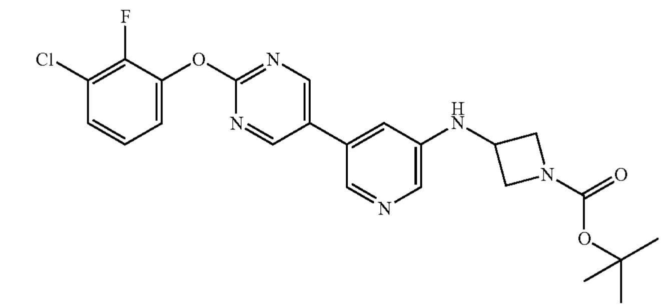 [SMILES: CC(C)(C)OC(=O)N1CC(Nc2cncc(-c3cnc(Oc4cccc(Cl)c4F)nc3)c2)C1] | tert-butyl 3-[[5-[2-(3-chloro-2-fluoro-phenoxy)pyrimidin-5-yl]-3-pyridyl]amino]azetidine-1-carboxylate | ($^{35}$Cl/$^{37}$Cl) 472.0/474.0 [M + H]$^+$ |
| 38 | 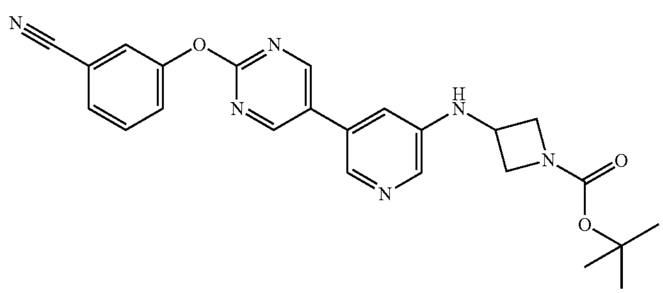 [SMILES: CC(C)(C)OC(=O)N1CC(Nc2cncc(-c3cnc(Oc4cccc(C#N)c4)nc3)c2)C1] | tert-butyl 3-[[5-[2-(3-cyanophenoxy)pyrimidin-5-yl]-3-pyridyl]amino]azetidine-1-carboxylate | 445.2 |
| 39 | 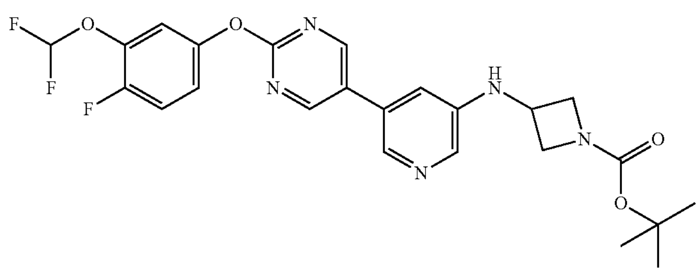 [SMILES: CC(C)(C)OC(=O)N1CC(Nc2cncc(-c3cnc(Oc4ccc(F)c(OC(F)F)c4)nc3)c2)C1] | tert-butyl 3-[[5-[2-[3-(difluoromethoxy)-4-fluoro-phenoxy]pyrimidin-5-yl]-3-pyridyl]amino]azetidine-1-carboxylate | 504.2 |
| 40 | 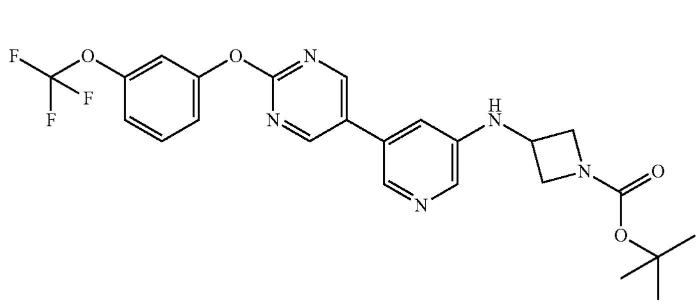 [SMILES: CC(C)(C)OC(=O)N1CC(Nc2cncc(-c3cnc(Oc4cccc(OC(F)(F)F)c4)nc3)c2)C1] | tert-butyl 3-[[5-[2-[3-(trifluoromethoxy)phenoxy]pyrimidin-5-yl]-3-pyridyl]amino]azetidine-1-carboxylate | 504.2 |

| Prep. | Structure | Name | MS m/z [M + H] |
|---|---|---|---|
| 41 | 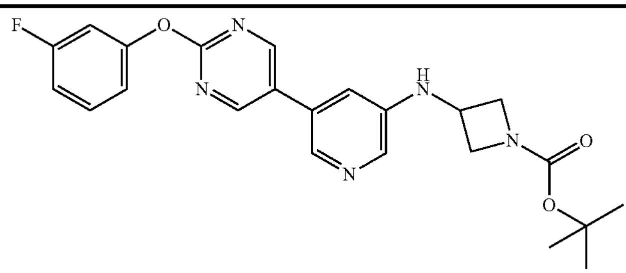 | tert-butyl 3-[[5-[2-(3-fluorophenoxy)pyrimidin-5-yl]-3-pyridyl]amino]azetidine-1-carboxylate | 438.2 |

Preparation 42 tert-butyl 4-[[5-[2-(3-chlorophenoxy)pyrimidin-5-yl]-3-pyridyl]amino]piperidine-1-carboxylate

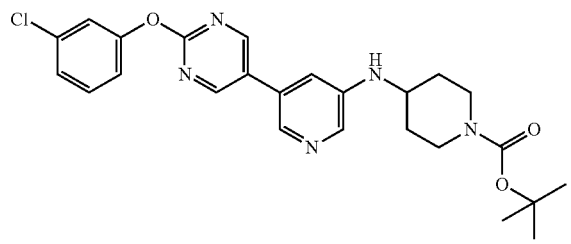 [SMILES: CC(C)(C)OC(=O)N1CCC(Nc2cncc(-c3cnc(Oc4cccc(Cl)c4)nc3)c2)CC1]

A 20 mL microwave vial is charged with tert-butyl 4-[(5-Dromo-3-pyridyl)amino]piperidine-1-carboxylate (0.5 g, 1.4 mmol), [2-(3-chlorophenoxy)pyrimidin-5-yl]boronic acid (0.4 g, 1.5 mmol), 1,4-dioxane (4.6 mL), water (1.4 mL), and $Cs_2CO_3$ (0.7 g, 2.1 mmol). Anhydrous nitrogen is bubbled subsurface for 5 minutes and 1,1'-bis(diphenylphosphino)ferrocene-palladium(II) dichloride (0.052 g, 0.069 mmol) is added. The vessel is flushed with additional nitrogen, sealed, and heated in a microwave at 130° C. for 30 minutes. The reaction mixture is diluted with water and extracted with EtOAc (3×10 mL). The combined organic extracts are washed with saturated aqueous NaCl, dried over $MgSO_4$, filtered, and concentrated under reduced pressure. The residue is purified by silica gel flash chromatography, eluting with a gradient of 20 to 100% EtOAc in hexanes, to yield the title compound (0.44 g, 66% yield). ES/MS m/z ($^{35}Cl/^{37}Cl$) 482.2/484.2 [M+H].

The following compounds are prepared essentially by the method of Preparation 42, using the appropriately substituted 3-bromopyridine and the appropriately substituted pyrimid-5-yl boronic acid or boronic ester.

| Prep | Structure | Name | ES/MS m/z [M + H] |
|---|---|---|---|
| 43 | 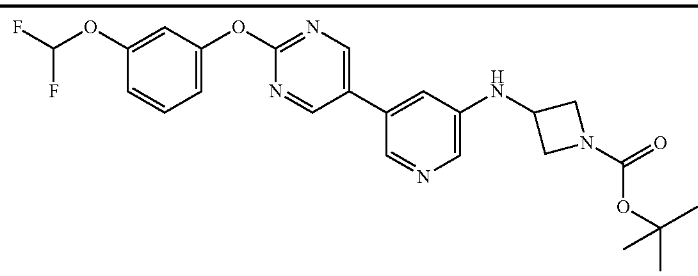 | tert-butyl 3-[[5-[2-[3-(difluoromethoxy)phenoxy]pyrimidin-5-yl]-3-pyridyl]amino]azetidine-1-carboxylate | 486.0 |
| 44 | 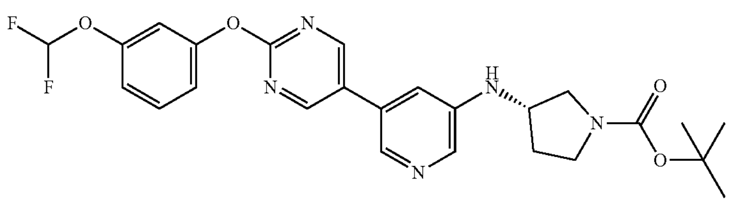 [SMILES: CC(C)(C)OC(=O)N1CC[C@H](Nc2cncc(-c3cnc(Oc4cccc(OC(F)F)c4)nc3)c2)C1] | tert-butyl (3S)-3-[[5-[2-[3-(difluoromethoxy)phenoxy]pyrimidin-5-yl]-3-pyridyl]amino]pyrrolidine-1-carboxylate | 500.2 |
| 45 | 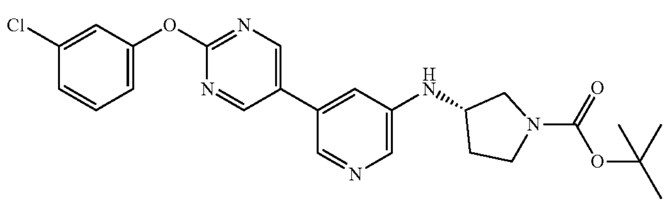 [SMILES: CC(C)(C)OC(=O)N1CC[C@H](Nc2cncc(-c3cnc(Oc4cccc(Cl)c4)nc3)c2)C1] | tert-butyl (3S)-3-[[5-[2-(3-chlorophenoxy)pyrimidin-5-yl]-3-pyridyl]amino]pyrrolidine-1-carboxylate | 468.0/470.0 ($^{35}Cl/^{37}Cl$) |

-continued

| Prep | Structure | Name | ES/MS m/z [M + H] |
|---|---|---|---|
| 46 | 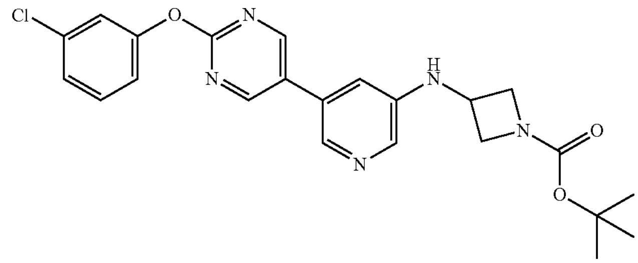 [SMILES: CC(C)(C)OC(=O)N1CC(Nc2cncc(-c3cnc(Oc4cccc(Cl)c4)nc3)c2)C1] | tert-butyl 3-[[5-[2-(3-chlorophenoxy)pyrimidin-5-yl]-3-pyridyl]amino]azetidine-1-carboxylate | 454.1/456.1 ($^{35}$Cl/$^{37}$Cl) |
| 47 | 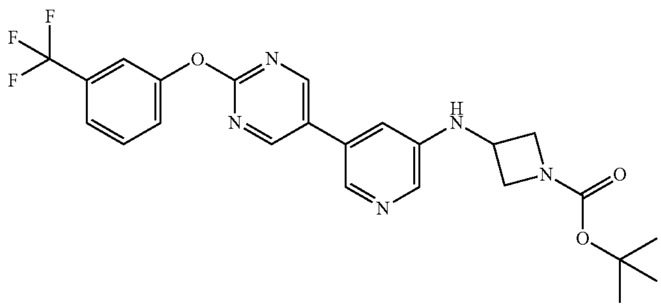 [SMILES: CC(C)(C)OC(=O)N1CC(Nc2cncc(-c3cnc(Oc4cccc(C(F)(F)F)c4)nc3)c2)C1] | tert-butyl 3-[[5-[2-[3-(trifluoromethyl)phenoxy]pyrimidin-5-yl]-3-pyridyl]amino]azetidine-1-carboxylate | 488.0 |
| 48 | 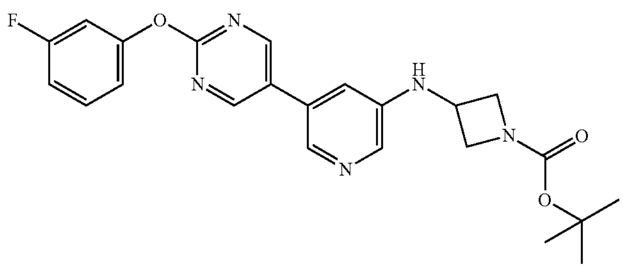 [SMILES: CC(C)(C)OC(=O)N1CC(Nc2cncc(-c3cnc(Oc4cccc(F)c4)nc3)c2)C1] | tert-butyl 3-[[5-[2-(3-fluorophenoxy)pyrimidin-5-yl]-3-pyridyl]amino]azetidine-1-carboxylate | 438.2 |
| 49 | 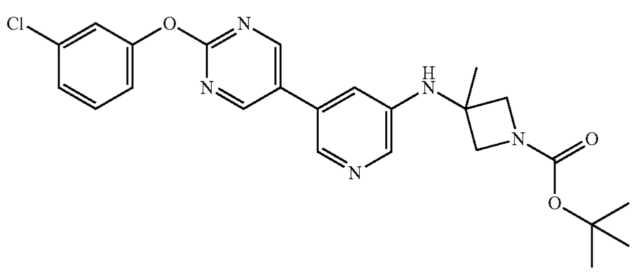 [SMILES: CC1(Nc2cncc(-c3cnc(Oc4cccc(Cl)c4)nc3)c2)CN(C(=O)OC(C)(C)C)C1] | tert-butyl 3-[[5-[2-(3-chlorophenoxy)pyrimidin-5-yl]-3-pyridyl]amino]-3-methyl-azetidine-1-carboxylate | 468.2 ($^{35}$Cl/$^{37}$Cl) |
| 50 | 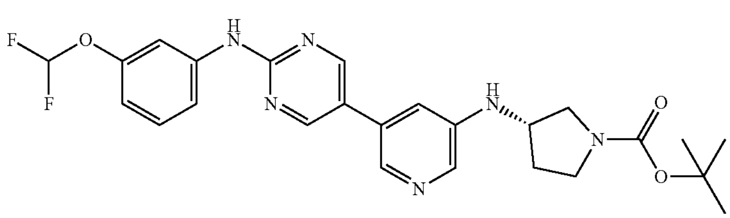 [SMILES: CC(C)(C)OC(=O)N1CC[C@H](Nc2cncc(-c3cnc(Nc4cccc(OC(F)F)c4)nc3)c2)C1] | tert-butyl (3S)-3-[[5-[2-[3-(difluoromethoxy)anilino]pyrimidin-5-yl]-3-pyridyl]amino]pyrrolidine-1-carboxylate | 499.2 |
| 51 | 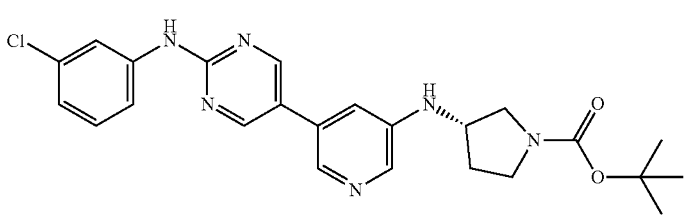 [SMILES: CC(C)(C)OC(=O)N1CC[C@H](Nc2cncc(-c3cnc(Nc4cccc(Cl)c4)nc3)c2)C1] | tert-butyl (3S)-3-[[5-[2-(3-chloroanilino)pyrimidin-5-yl]-3-pyridyl]amino]pyrrolidine-1-carboxylate | 467.2/469.2 ($^{35}$Cl/$^{37}$Cl) |

-continued

| Prep | Structure | Name | ES/MS m/z [M + H] |
|---|---|---|---|
| 52 | 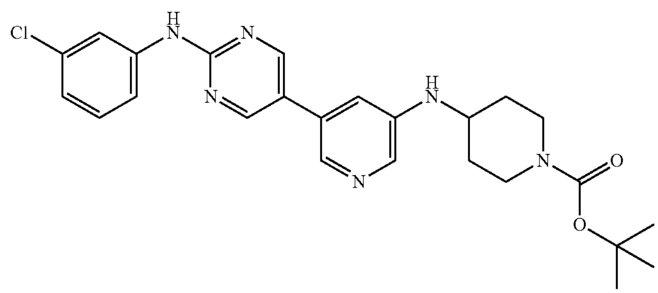 [SMILES: CC(C)(C)OC(=O)N1CCC(Nc2cncc(-c3cnc(Nc4cccc(Cl)c4)nc3)c2)CC1] | tert-butyl 4-[[5-[2-(3-chloroanilino)pyrimidin-5-yl]-3-pyridyl]amino]piperidine-1-carboxylate | 481.2/483.2 ($^{35}$Cl/$^{37}$Cl) |
| 53 | 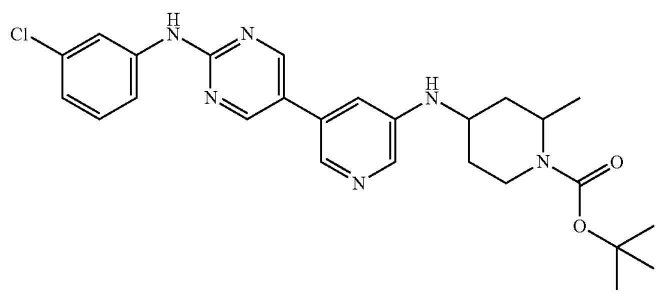 [SMILES: CC1CC(Nc2cncc(-c3cnc(Nc4cccc(Cl)c4)nc3)c2)CCN1C(=O)OC(C)(C)C] | tert-butyl 4-[[5-[2-(3-chloroanilino)pyrimidin-5-yl]-3-pyridyl]amino]-2-methyl-piperidine-1-carboxylate | 495.2/497.2 ($^{35}$Cl/$^{37}$Cl) |

Preparation 54

5-(5-bromo-3-pyridyl)-2-chloro-pyrimidine

A round bottom flask is charged with (2-chloropyrimidin-5-yl)boronic acid (2.9 g, 18.0 mmol), 3-bromo-5-iodo-pyridine (5.0 g, 17.6 mmol), [1,1'-bis(diphenylphosphino)ferrocene]dichloropalladium(II), (700 mg, 0.96 mmol), K$_2$CO$_3$ (3.89 g, 27.9 mmol), 1,4-dioxane (150 mL), and water (15 mL). The reaction mixture is heated to 60° C. for 24 h and cooled to RT. The suspension is filtered over diatomaceous earth and the filtrate concentrated under reduced pressure. The resulting residue is suspended in DCM, dried over Na$_2$SO$_4$, filtered, and concentrated under reduced pressure. The resulting residue is purified by silica gel flash column chromatography, using DCM as an eluent, to obtain the title compound (2.4 g, 50% yield) as a grey solid. MS m/z ($^{35}$Cl$^{79}$Br/$^{37}$Cl$^{79}$Br,$^{35}$Cl$^{81}$Br/$^{37}$Cl$^{81}$Br) 270.0/272.0/274.0 [M+H].

Preparation 55

5-(5-bromo-3-pyridyl)-2-(3-chloro-4-fluoro-phenoxy)pyrimidine

To a 20 ml microwave vial is added 5-(5-bromo-3-pyridyl)-2-chloro-pyrimidine (450 mg, 1.7 mmol), 3-chloro-4-fluoro-phenol (293 mg, 2.0 mmol), Cs$_2$CO$_3$ (1.1 g, 3.31 mmol) and DMF (6 mL). Nitrogen is bubbled through the resulting mixture for several minutes. The reaction is stirred at RT overnight. The mixture is diluted with EtOAc and filtered over a bed of diatomaceous earth. The filtrate is sequentially washed with saturated aq. NaHCO$_3$ (1×30 mL), water (1×30 ml), and saturated aqueous NaCl. The organic layer is separated, dried over MgSO$_4$, filtered, and concentrated to dryness under reduced pressure to obtain the title compound (710 mg, 101% Yield) with an assumed purity of 90% sufficient for use without additional purification. ES/MS m/z ($^{35}$Cl$^{79}$Br/$^{37}$Cl$^{79}$Br,$^{35}$Cl$^{81}$Br/$^{37}$Cl$^{81}$Br) 380.0/382.0/384.0 [M+H].

Preparation 56

5-(5-bromo-3-pyridyl)-2-(3-chloro-4-fluoro-phenoxy)pyrimidine

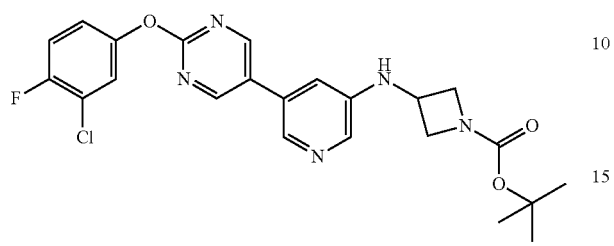

To a microwave vial with a stir bar is added 5-(5-bromo-3-pyridyl)-2-(3-chloro-4-fluoro-phenoxy)pyrimidine (710 mg, 1.68 mmol), [(2-di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate (5 mg, 0.005 mmol), and sodium tert-butoxide (194 mg, 2.0 mmol). The vial is sealed with a septum, vacuum evacuated, and back-filled with nitrogen three times. Tert-butyl 3-aminoazetidine-1-carboxylate (0.32 mL, 2.0 mmol) and 1,4-dioxane (17 mL) are added. The sealed vial is heated in a microwave at 120° C. for 1 h. The reaction mixture is diluted with DCM, filtered through diatomaceous earth, and the filtrate is concentrated under reduced pressure. The resulting crude residue is purified by silica gel flash chromatography to yield the title compound (360 mg, 45% yield). ES/MS m/z ($^{35}$Cl/$^{37}$Cl) 472.0/474.0 [M+H].

Preparation 57 tert-butyl 3-[[5-[2-(3-ethynylphenoxy)pyrimidin-5-yl]-3-pyridyl]amino]azetidine-1-carboxylate

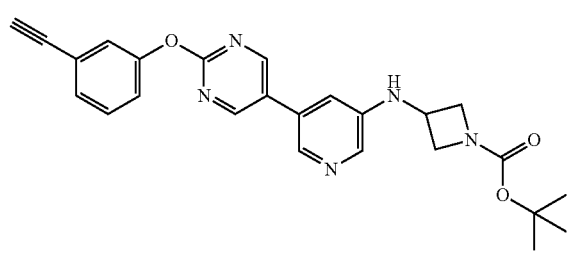 [SMILES: C#Cc1cccc(Oc2ncc(-c3cncc(NC4CN(C(=O)OC(C)(C)C)C4)c3)cn2)c1]

A solution of 1M tetrabutylammonium fluoride in THF (0.6 mL, 0.6 mmol) is added to a solution of tert-butyl 3-[[5-[2-[3-(2-triisopropylsilylethynyl)phenoxy]pyrimidin-5-yl]-3-pyridyl]amino]azetidine-1-carboxylate (202 mg, 0.3 mmol) in anhydrous THF (1.33 mL) at RT under an atmosphere of argon. The reaction mixture is stirred at RT for 1 h. Water is added and the resulting solution is extracted three times with EtAOc. The layers are separated, and the combined organic extracts are washed with saturated aqueous NaCl, dried over Na$_2$SO$_4$, filtered, and concentrated under reduced pressure to obtain the title compound (172 mg, quantitative yield), sufficient for use without additional purification. MS m/z 444.2 [M+H].

Preparation 58 tert-butyl (3S)-3-[[5-(2-chloropyrimidin-5-yl)-3-pyridyl]amino]pyrrolidine-1-carboxylate

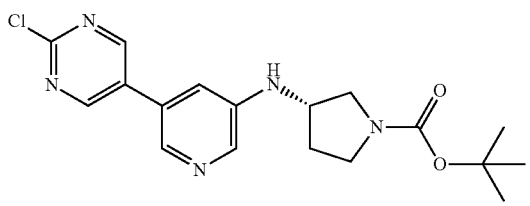 [SMILES: CC(C)(C)OC(=O)N1CC[C@H](Nc2cncc(-c3cnc(Cl)nc3)c2)C1]

Tert-butyl (3S)-3-[(5-bromo-3-pyridyl)amino]pyrrolidine-1-carboxylate (5.0 g, 14.6 mmol), 2-chloropyrimidine-5-boronic acid (4.8 g, 29.2 mmol), CsF (8.9 g, 58.4 mmol) and tri-tert-butylphosphonium tetrafluoroborate (350 mg, 1.2 mmol) are added to a dry 250 mL pressure flask. 1,4-dioxane (146 mL) is added and nitrogen gas is bubbled through the solution for 15 minutes. Tris(dibenzylideneacetone)dipalladium(0) (552 mg, 0.6 mmol) is added and the sealed vessel heated is heated to 85° C. for 5 h. Upon cooling to RT, the reaction is diluted with EtOAc and water. The suspension is filtered over diatomaceous earth and is the resulting layers in the filtrate are separated. The aqueous phase is extracted with EtAOc (2×150 mL). The combined organic extracts are washed with saturated aqueous NaCl (75 mL), dried over MgSO$_4$, filtered, and concentrated under reduced pressure. The resulting residue is purified by silica gel flash column chromatography, using a gradient of 0 to 10% MeOH in DCM. The purified product is recrystallized from EtOH, and the precipitate is collected by filtration. Additional product is crystalized from the filtrate, isolated by filtration and washed with cold ethanol. Products are combined to yield the title compound (4.4 g, 71% yield) in 88% purity. ES/MS m/z ($^{35}$Cl/$^{37}$Cl) 376.0/378.0 [M+H].

The following compounds are prepared essentially by the method of Preparation 58:

| Prep. | Structure | Name | ES/MS m/z ($^{35}Cl/^{37}Cl$) [M + H] |
|---|---|---|---|
| 59 | 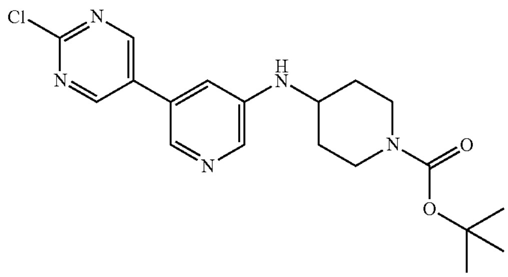 [SMILES: CC(C)(C)OC(=O)N1CCC(Nc2cncc(-c3cnc(Cl)nc3)c2)CC1] | tert-butyl 4-[[5-(2-chloro-pyrimidin-5-yl)-3-pyridyl]amino]piperidine-1-carboxylate | 390/392.0 |

Preparation 60 tert-butyl (3S)-3-[[5-[2-[(6-methyl-2-pyridyl)amino]pyrimidin-5-yl]-3-pyridyl]amino]pyrrolidine-1-carboxylate

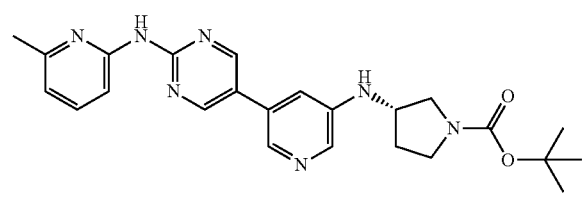 [SMILES: Cc1cccc(Nc2ncc(-c3cncc(N[C@H]4CCN(C(=O)OC(C)(C)C)C4)c3)cn2)n1]

Tert-butyl (3S)-3-[[5-(2-chloropyrimidin-5-yl)-3-pyridyl]amino]pyrrolidine-1-carboxylate (750 mg, 2.0 mmol), 2-amino-6-methylpyridine (264 mg, 2.4 mmol), $K_2CO_3$ (690 mg, 4.99 mmol, 0.295 mL), tert-butanol (10 mL), and [(2-di-tert-butylphosphino-3,6-dimethoxy-2',4',6'-triisopropyl-1,1'-biphenyl)-2-(2'-amino-1,1'-biphenyl)]palladium(II) methanesulfonate (90 mg, 0.1 mmol) are placed in a 20 mL vial. Dry nitrogen is bubbled subsurface for 15 minutes. The sealed vial is heated in a microwave at 120° C. for 45 minutes. The solution is diluted with water and extracted with EtOAc (3×15 mL). The combined organic extracts are washed with saturated aqueous NaCl, dried over $MgSO_4$, filtered, and concentrated under reduced pressure. The resulting residue is purified by silica gel flash column chromatography, using a gradient of 70 to 100% EtOAc in hexanes followed by 5% MeOH in EtOAc, to obtain the title compound (0.55 g, 62% yield). ES/MS m/z 448.2 [M+H].

The following compounds are prepared essentially by the method of Preparation 60:

| Prep. | Structure | Name | ES/MS m/z [M + H] |
|---|---|---|---|
| 61 | 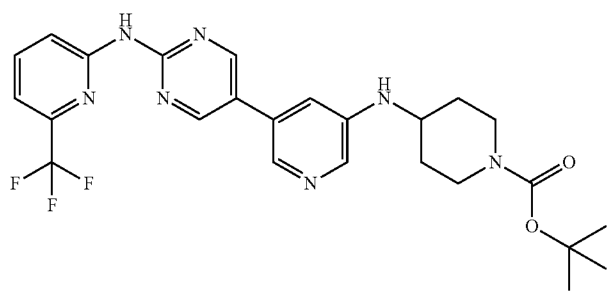 [SMILES: CC(C)(C)OC(=O)N1CCC(Nc2cncc(-c3cnc(Nc4cccc(C(F)(F)F)n4)nc3)c2)CC1] | tert-butyl 4-[[5-[2-[[6-(trifluoromethyl)-2-pyridyl]amino]pyrimidin-5-yl]-3-pyridyl]amino]piperidine-1-carboxylate | 516.2 |
| 62 | 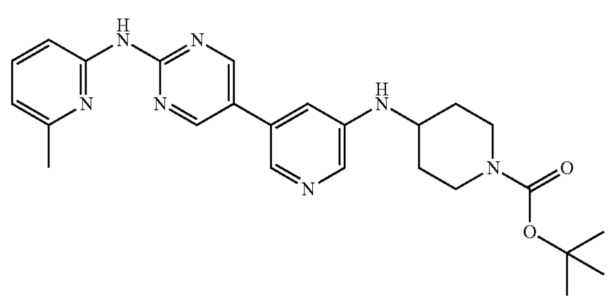 [SMILES: Cc1cccc(Nc2ncc(-c3cncc(NC4CCN(C(=O)OC(C)(C)C)CC4)c3)cn2)n1] | tert-butyl 4-[[5-[2-[(6-methyl-2-pyridyl)amino]pyrimidin-5-yl]-3-pyridyl]amino]piperidine-1-carboxylate | 462.2 |

| Prep. | Structure | Name | ES/MS m/z [M + H] |
|---|---|---|---|
| 63 | 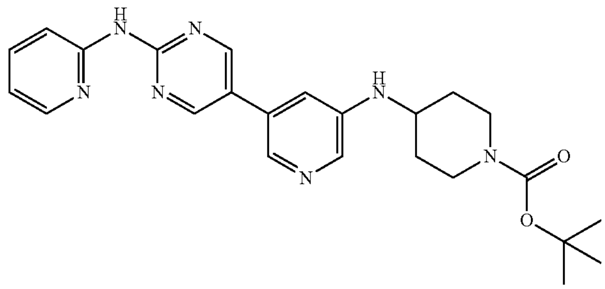 [SMILES: CC(C)(C)OC(=O)N1CCC(Nc2cncc(-c3cnc(Nc4ccccn4)nc3)c2)CC1] | tert-butyl 4-[[5-[2-(2-pyridylamino)pyrimidin-5-yl]-3-pyridyl]amino]piperidine-1-carboxylate | 448.2 |

Preparation 64 tert-butyl 3-[(6-bromopyrazin-2-yl)amino]azetidine-1-carboxylate

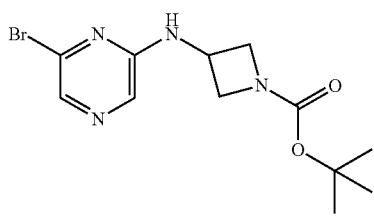

An 8 mL vial with stir bar is charged with 2,6-dibromopyrazine (25.0 g, 110.0 mmol) and tert-butyl-3-aminoazetidine-1-carboxylate (21.0 g, 120.0 mmol), dimethyl sulfoxide (100 mL) and TEA (22.0 mL, 160.0 mmol). The sealed vessel is heated 90° C. for 4 h. The suspension is cooled to RT, diluted with saturated aqueous NaHCO$_3$, and extracted with EtOAc (2×150 mL). The combined extracts are washed with saturated aqueous NaHCO$_3$ (2×50 mL) and saturated aqueous NaCl. The organic extracts are dried over MgSO$_4$, filtered, and concentrated under reduced pressure. The resulting residue is dissolved in DCM (~200 mL). Hexanes (~1 L) are added dropwise to the stirred solution over ~1 h. The suspension is stirred for 1 h and then cooled to 0° C. The resulting white precipitate is isolated by filtration to yield the title compound (25.0 g, 72% yield). ES/MS m/z ($^{79}$Br/$^{81}$Br) 329.0/331.0 [M+H].

The following compounds are prepared essentially by the method of Preparation 64, using 2,6-dihalopyrazine and the appropriately substituted amine.

| Prep. | Structure | Name | MS ES/MS m/z ($^{79}$Br/$^{81}$Br) [M + H] |
|---|---|---|---|
| 65 | 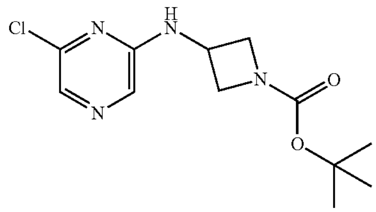 [SMILES: CC(C)(C)OC(=O)N1CC(Nc2cncc(Cl)n2)C1] | tert-butyl 3-[(6-chloropyrazin-2-yl)amino]azetidine-1-carboxylate | ($^{35}$Cl/$^{37}$Cl) 285.0/287.0 [M + H] |
| 66 | 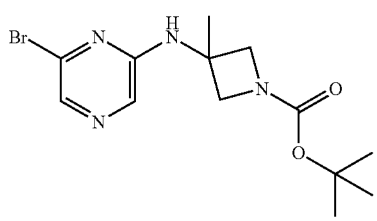 [SMILES: CC1(Nc2cncc(Br)n2)CN(C(=O)OC(C)(C)C)C1] | tert-butyl 3-[(6-bromopyrazin-2-yl)amino]-3-methyl-azetidine-1-carboxylate | ($^{79}$Br/$^{81}$Br) 343.0/345.0 [M + H] |
| 67 | 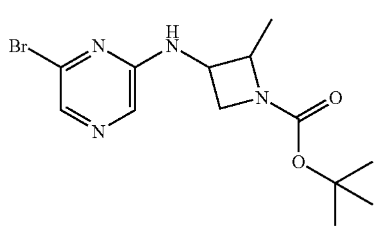 [SMILES: CC1C(Nc2cncc(Br)n2)CN1C(=O)OC(C)(C)C] | tert-butyl 3-[(6-bromopyrazin-2-yl)amino]-2-methyl-azetidine-1-carboxylate | ($^{79}$Br/$^{81}$Br) 343.0/345.0 [M + H] |

| Prep. | Structure | Name | MS ES/MS m/z ($^{79}$Br/$^{81}$Br) [M + H] |
|---|---|---|---|
| 68 | 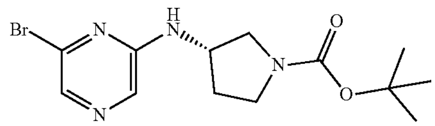 [SMILES: CC(C)(C)OC(=O)N1CC[C@H](Nc2cncc(Br)n2)C1] | tert-butyl (3S)-3-[(6-bromopyrazin-2-yl)amino]pyrrolidine-1-carboxylate | ($^{79}$Br/$^{81}$Br) 365.0/366.80 [M + Na] |
| 69 | 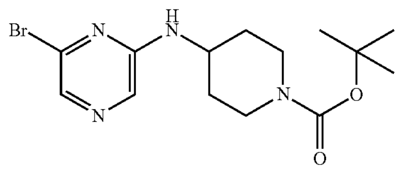 [SMILES: CC(C)(C)OC(=O)N1CCC(Nc2cncc(Br)n2)CC1] | tert-butyl 4-[(6-bromopyrazin-2-yl)amino]piperidine-1-carboxylate | ($^{79}$Br/$^{81}$Br) 301.0/303 [M + H − tBu] |

Preparation 70

[2-[3-(trifluoromethoxy)anilino]pyrimidin-5-yl]boronic acid hydrochloride

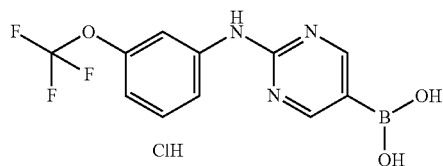 [SMILES: OB(O)c1cnc(Nc2cccc(OC(F)(F)F)c2)nc1 ; Cl]

A 100 mL RBF is charged with (2-chloropyrimidin-5-yl)boronic acid (5.0 g, 32 mmol), 3-(trifluoromethoxy)aniline (6.7 g, 38 mmol), ethanol (16 mL) and hydrochloric acid (12 M in water, 0.13 mL, 1.6 mmol). The mixture is heated to 80° C. for 30 minutes. The flask is removed from heat and water is slowly added to the stirred solution. The heterogeneous solution becomes homogenous and then a spongy precipitate is formed. The solution is diluted with 300 mL EtOH and 800 mL water. The precipitate is isolated by filtration and dried under reduced pressure to obtain the title compound as an off-white solid. ES/MS m/z 300.0 [M+H].

The following compounds are prepared essentially by the method of Preparation 70 with suitable starting materials.

Preparation 73

[2-(3-chlorophenoxy)pyrimidin-5-yl]boronic acid

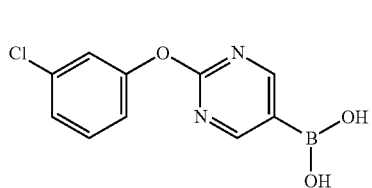

5-bromo-2-(3-chlorophenoxy)pyrimidine (2.0 g, 6.7 mmol) is weighed into a 50 mL flask with a stir bar and is dissolved in THF (5 mL) and toluene (20 mL). Triisopropylborate (1.9 mL, 8.2 mmol) is added under a nitrogen atmosphere. The resulting solution is stirred and cooled in a dry ice-acetone bath (>−70° C.). A 2.5 M solution of n-BuLi in hexanes (3.5 mL, 8.8 mmol) is added slowly to the mixture via a syringe over 10 min. The solution becomes a vivid yellow color. After 15 minutes, the mixture is quenched with ~3 mL MeOH while still in the cooling bath. The cooling bath is removed, water (10 mL) is added, and the pH is adjusted to between 5 and 6 using 1 M aqueous HCl and 2 M aqueous $K_3PO_4$. The resulting white solid is collected by filtration and washed with water. The solid is

| Prep. | Structure | Name | ES/MS m/z [M + H] |
|---|---|---|---|
| 71 | 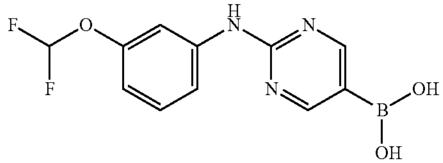 [SMILES: OB(O)c1cnc(Nc2cccc(OC(F)F)c2)nc1] | [2-[3-(difluoromethoxy)anilino]pyrimidin-5-yl]boronic acid | 282.0 |
| 72 | | [2-(3-chloroanilino)pyrimidin-5-yl]boronic acid | 250.0/252.0 | dried at 5 mbar with gentle warming for ~1 hour to obtain the title compound (1.09 g, 61% yield). ES/MS m/z ($^{35}$Cl/$^{37}$Cl) 251.0/253.0 [M+H].

The following compounds are prepared essentially by the method of Preparation 73, using an appropriately substituted 5-bromo-2-aryloxypyrimidine.

| Prep. | Structure | Name | ES/MS m/z [M + H] |
|---|---|---|---|
| 74 | 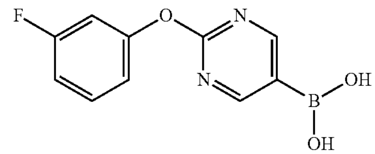 [SMILES: OB(O)c1cnc(Oc2cccc(F)c2)nc1] | [2-(3-fluorophenoxy)pyrimidin-5-yl]boronic acid | 235.0 |
| 75 | 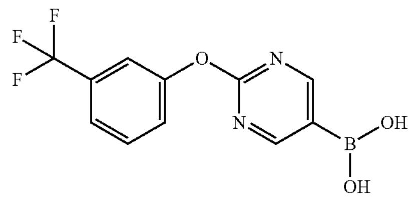 [SMILES: OB(O)c1cnc(Oc2cccc(C(F)(F)F)c2)nc1] | [2-[3-(trifluoromethyl)phenoxy]pyrimidin-5-yl]boronic acid | 285.0 |
| 76 | 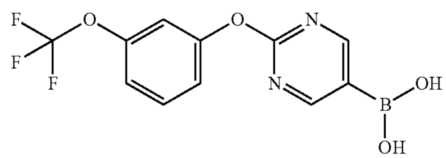 [SMILES: OB(O)c1cnc(Oc2cccc(OC(F)(F)F)c2)nc1] | [2-[3-(trifluoromethoxy)phenoxy]pyrimidin-5-yl]boronic acid | 301.0 |
| 77 | 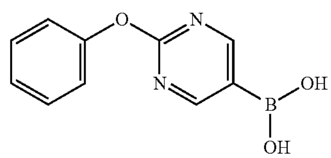 [SMILES: OB(O)c1cnc(Oc2ccccc2)nc1] | (2-phenoxypyrimidin-5-yl)boronic acid | 217.0 |
| 78 | 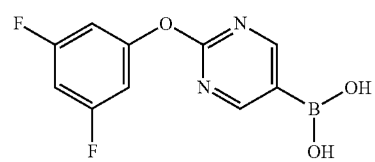 [SMILES: OB(O)c1cnc(Oc2cc(F)cc(F)c2)nc1] | [2-(3,5-difluorophenoxy)pyrimidin-5-yl]boronic acid | 253.0 |
| 79 | 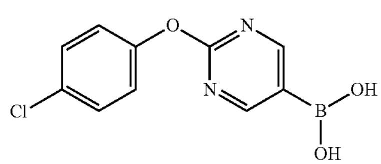 [SMILES: OB(O)c1cnc(Oc2ccc(Cl)cc2)nc1] | [2-(4-chlorophenoxy)pyrimidin-5-yl]boronic acid | ($^{35}$Cl/$^{37}$Cl) 251.0/253.0 |
| 80 | 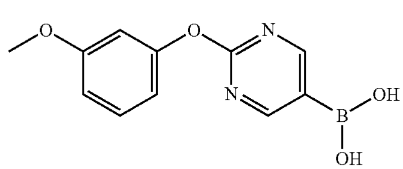 [SMILES: COc1cccc(Oc2ncc(B(O)O)cn2)c1] | [2-(3-methoxyphenoxy)pyrimidin-5-yl]boronic acid | 247.0 |

Preparation 81

[2-[3-(difluoromethoxy)phenoxy]pyrimidin-5-yl]boronic acid

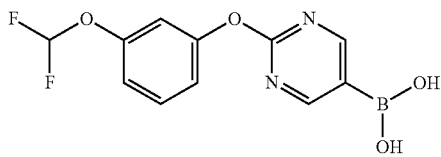 [SMILES: OB(O)c1cnc(Oc2cccc(OC(F)F)c2)nc1]

A round bottom flask is charged with 5-bromo-2-[3-(difluoromethoxy)phenoxy]pyrimidine (2.5 g, 7.9 mmol), KOAc (2.3, 24 mmol), XPhos Palladacycle Gen 2 (0.063 g, 0.079 mmol), $B_2H_4O_4$ (2.2 g, 24 mmol), EtOH (39 mL) and ethylene glycol (1.3 mL). The mixture is heated to 50° C. for 30 min. The reaction is cooled to RT and the solvent is removed under reduced pressure. Water (30 mL) is added to the resulting residue and the suspension is extracted with MTBE (40 mL). The organic layer is washed with 0.5 M aqueous NaOH (30 mL), the phases are separated, and the basic aqueous layer is acidified to pH~2 with aqueous HCl and extracted with MTBE (40 mL). The organic extracts are dried over MgSO4, filtered, and concentrated under reduced pressure to obtain the title compound (1.2 g, 52% yield). ES/MS m/z 283.0 [M+H].

Preparation 82 tert-butyl 3-[[6-[2-[3-(difluoromethoxy)phenoxy]pyrimidin-5-yl]pyrazin-2-yl]amino]azetidine-1-carboxylate

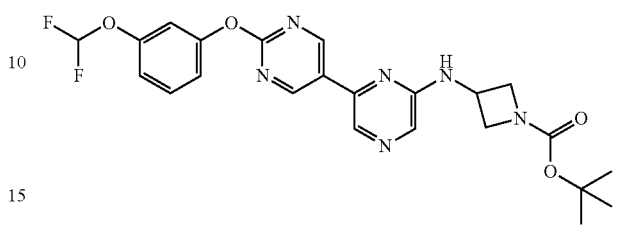

A pressure vial is charged with [2-[3-(difluoromethoxy)phenoxy]pyrimidin-5-yl]boronic acid (5.0 g, 18.0 mmol), tert-butyl 3-[(6-bromopyrazin-2-yl)amino]azetidine-1-carboxylate (5.8 g, 18.0 mmol), [1,1'-bis(diphenylphosphino)ferrocenepalladium(II) dichloride dichloromethane complex (1.5 g, 1.8 mmol), $Cs_2CO_3$ (12 g, 35.0 mmol), 1,4-dioxane (59 mL) and water (18 mL). Argon is bubbled subsurface for 2 min. The sealed flask is heated in an oil bath for 4 h at 80° C. The reaction mixture is diluted with EtOAc and filtered over diatomaceous earth. The filtrate is concentrated under reduced pressure and the resulting residue is purified by flash chromatography over silica gel, eluting with EtOAc, to obtain the title compound (4.8 g, 55% yield). ES/MS m/z 509.0 [M+Na].

The following compounds are prepared essentially by the method of Preparation 82, using the appropriate 2-substituted pyrimidin-5-yl-boronic acid or boronic ester and the appropriate 6-substituted-2-bromo- or 6-substituted-2-chloropyrazine.

| Prep. | Structure | Name | ES/MS m/z |
|---|---|---|---|
| 83 | 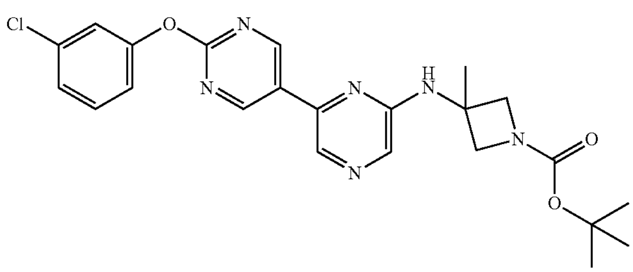 | tert-butyl 3-[[6-[2-(3-chlorophenoxy)pyrimidin-5-yl]pyrazin-2-yl]amino]-3-methyl-azetidine-1-carboxylate | 413.0/415.0 [M + H − $C_4H_8$] |
| 84 | 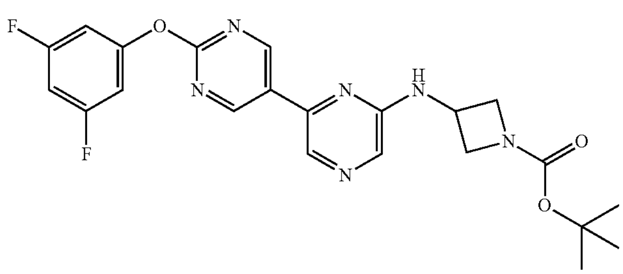 [SMILES: CC(C)(C)OC(=O)N1CC(Nc2cncc(-c3cnc(Oc4cc(F)cc(F)c4)nc3)n2)C1] | tert-butyl 3-[[6-[2-(3,5-difluorophenoxy)pyrimidin-5-yl]pyrazin-2-yl]amino]azetidine-1-carboxylate | 479.0 [M + Na] |

-continued

| Prep. | Structure | Name | ES/MS m/z |
|---|---|---|---|
| 85 | 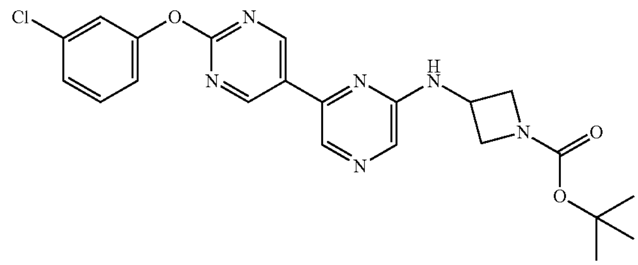 [SMILES: CC(C)(C)OC(=O)N1CC(Nc2cncc(-c3cnc(Oc4cccc(Cl)c4)nc3)n2)C1] | tert-butyl 3-[[6-[2-(3-chlorophenoxy)pyrimidin-5-yl]pyrazin-2-yl]amino]azetidine-1-carboxylate | ($^{35}$Cl/$^{37}$Cl) 477.0/479.0 [M + Na] |
| 86 | 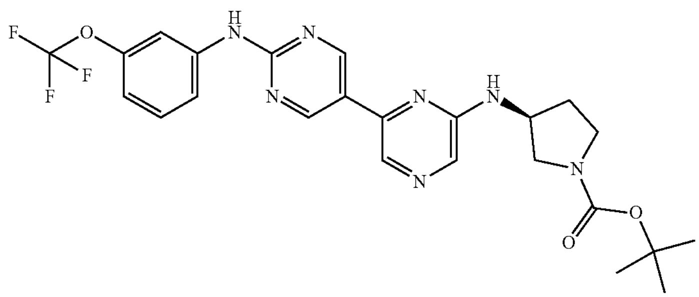 [SMILES: CC(C)(C)OC(=O)N1CC[C@H](Nc2cncc(-c3cnc(Nc4cccc(OC(F)(F)F)c4)nc3)n2)C1] | tert-butyl (3S)-3-[[6-[2-[3-(trifluoromethoxy)anilino]pyrimidin-5-yl]pyrazin-2-yl]amino]pyrrolidine-1-carboxylate | 540 [M + Na] |
| 87 | 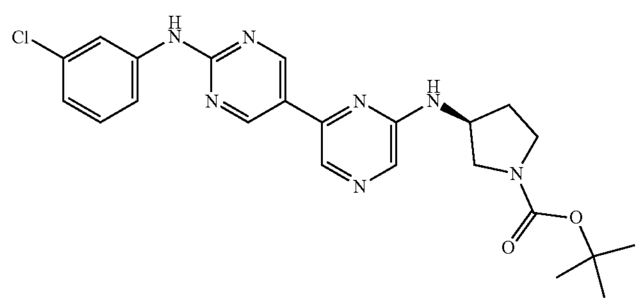 [SMILES: CC(C)(C)OC(=O)N1CC[C@H](Nc2cncc(-c3cnc(Nc4cccc(Cl)c4)nc3)n2)C1] | tert-butyl (3S)-3-[[6-[2-(3-chloroanilino)pyrimidin-5-yl]pyrazin-2-yl]amino]pyrrolidine-1-carboxylate | ($^{35}$Cl/$^{37}$Cl) 468.2/470.2 [M + H] |
| 88 | 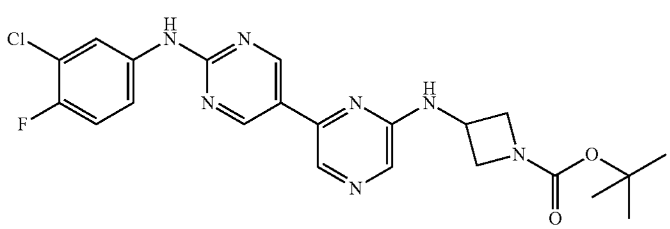 [SMILES: CC(C)(C)OC(=O)N1CC(Nc2cncc(-c3cnc(Nc4ccc(F)c(Cl)c4)nc3)n2)C1] | tert-butyl 3-[[6-[2-(3-chloro-4-fluoro-anilino)pyrimidin-5-yl]pyrazin-2-yl]amino]azetidine-1-carboxylate | ($^{35}$Cl/$^{37}$Cl) 472.0/7474.0 [M + H] |
| 89 | 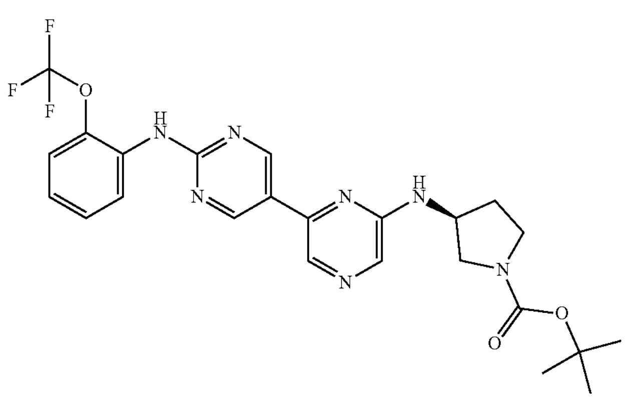 [SMILES: CC(C)(C)OC(=O)N1CC[C@H](Nc2cncc(-c3cnc(Nc4ccccc4OC(F)(F)F)nc3)n2)C1] | tert-butyl (3S)-3-[[6-[2-[2-(trifluoromethoxy)anilino]pyrimidin-5-yl]pyrazin-2-yl]amino]pyrrolidine-1-carboxylate | 518.2 [M + H] |

-continued

| Prep. | Structure | Name | ES/MS m/z |
|---|---|---|---|
| 90 | 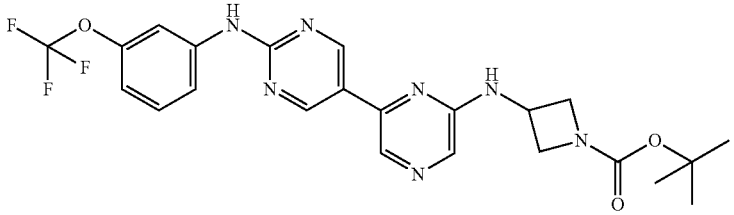 [SMILES: CC(C)(C)OC(=O)N1CC(Nc2cncc(-c3cnc(Nc4cccc(OC(F)(F)F)c4)nc3)n2)C1] | tert-butyl 3-[[6-[2-[3-(trifluoromethoxy)anilino]pyrimidin-5-yl]pyrazin-2-yl]amino]azetidine-1-carboxylate | 504.0 [M + H] |
| 91 | 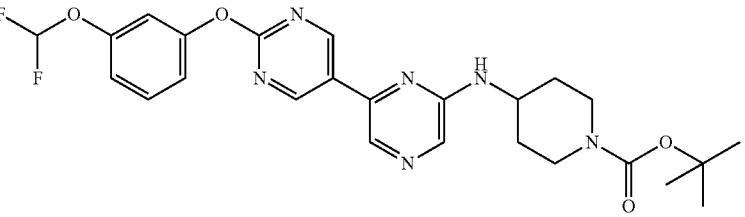 [SMILES: CC(C)(C)OC(=O)N1CCC(Nc2cncc(-c3cnc(Oc4cccc(OC(F)F)c4)nc3)n2)CC1] | tert-butyl 4-[[6-[2-[3-(difluoromethoxy)phenoxy]pyrimidin-5-yl]pyrazin-2-yl]amino]piperidine-1-carboxylate | 515.2 [M + H] |
| 92 | 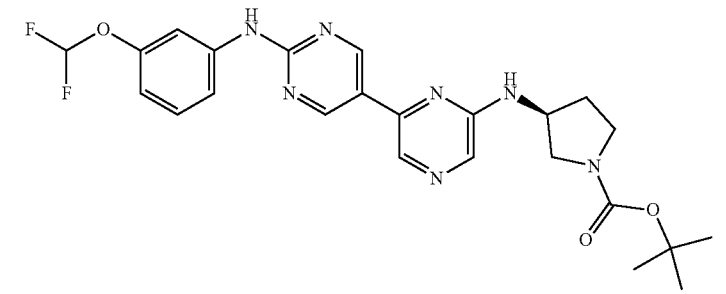 [SMILES: CC(C)(C)OC(=O)N1CC[C@H](Nc2cncc(-c3cnc(Nc4cccc(OC(F)F)c4)nc3)n2)C1] | tert-butyl (3S)-3-[[6-[2-[3-(difluoromethoxy)anilino]pyrimidin-5-yl]pyrazin-2-yl]amino]pyrrolidine-1-carboxylate | 500.2 [M + H] |
| 93 | 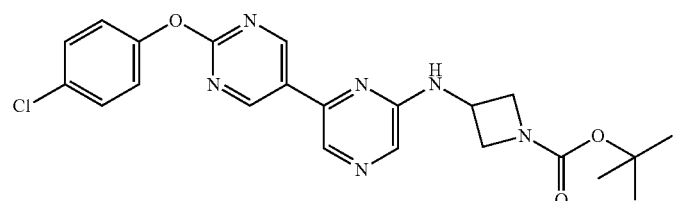 | tert-butyl 3-[[6-[2-(4-chlorophenoxy)pyrimidin-5-yl]pyrazin-2-yl]amino]azetidine-1-carboxylate | ($^{35}$Cl/$^{37}$Cl) 455.0/457.0 [M + H] |
| 94 | 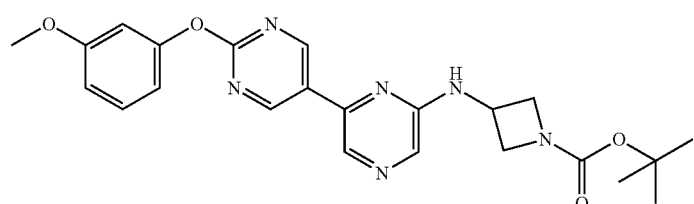 | tert-butyl 3-[[6-[2-(3-methoxyphenoxy)pyrimidin-5-yl]pyrazin-2-yl]amino]azetidine-1-carboxylate | 473.0 [M + Na] |
| 95 | 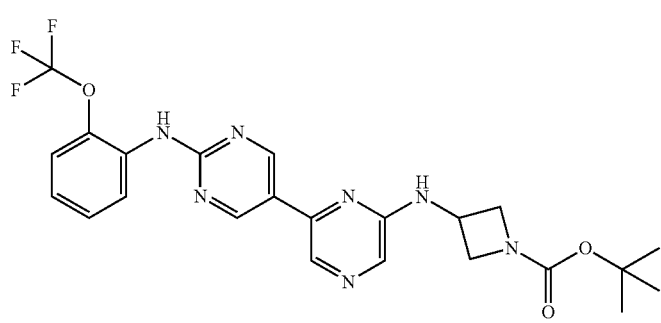 [SMILES: CC(C)(C)OC(=O)N1CC(Nc2cncc(-c3cnc(Nc4ccccc4OC(F)(F)F)nc3)n2)C1] | tert-butyl 3-[[6-[2-[2-(trifluoromethoxy)anilino]pyrimidin-5-yl]pyrazin-2-yl]amino]azetidine-1-carboxylate | 504.0 [M + H] |

| Prep. | Structure | Name | ES/MS m/z |
|---|---|---|---|
| 96 | 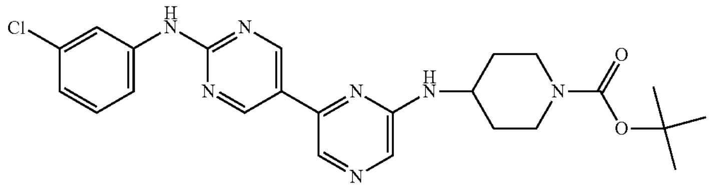 [SMILES: CC(C)(C)OC(=O)N1CCC(Nc2cncc(-c3cnc(Nc4cccc(Cl)c4)nc3)n2)CC1] | tert-butyl 4-[[6-[2-(3-chloroanilino)pyrimidin-5-yl]pyrazin-2-yl]amino]piperidine-1-carboxylate | ($^{35}$Cl/$^{37}$Cl) 482.0/484.0 [M + H] |
| 97 | 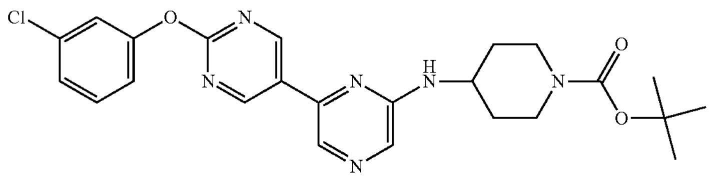 [SMILES: CC(C)(C)OC(=O)N1CCC(Nc2cncc(-c3cnc(Oc4cccc(Cl)c4)nc3)n2)CC1] | tert-butyl 4-[[6-[2-(3-chlorophenoxy)pyrimidin-5-yl]pyrazin-2-yl]amino]piperidine-1-carboxylate | 505.0/507.0 [M + Na] |

Preparation 98 tert-butyl (2S,3R)-3-[[6-[2-(3-chlorophenoxy)pyrimidin-5-yl]pyrazin-2-yl]amino]-2-methyl-azetidine-1-carboxylate, Isomer 1

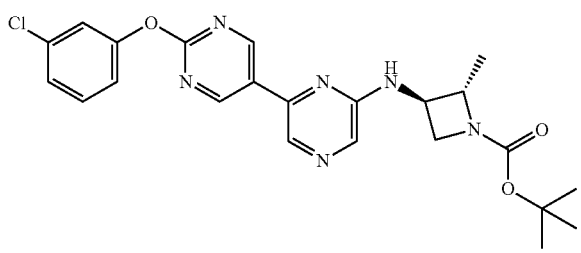 [SMILES: C[C@H]1[C@H](Nc2cncc(-c3cnc(Oc4cccc(Cl)c4)nc3)n2)CN1C(=O)OC(C)(C)C]

A microwave vial is charged with tert-butyl 3-[(6-bromopyrazin-2-yl)amino]-2-methyl-azetidine-1-carboxylate (0.29 g, 0.8 mmol), 2-(3-chlorophenoxy)-5-(4,4,5,5-tetramethyl-1,3,2-dioxaborolan-2-yl)pyrimidine (0.5 g, 0.9 mmol), [1,1'-bis(diphenylphosphino)ferrocene]dichloropalladium (II)-DCM complex (0.07 g, 0.08 mmol), Cs$_2$CO$_3$ (0.5 g, 0.13 mL, 1.7 mmol), 1,4-dioxane (2.80 mL) and water (0.8 mL). Argon is bubbled subsurface for 2 min. The sealed vial is heated in a microwave reactor for 15 min at 120° C. The reaction mixture is diluted with EtAOc and filtered through diatomaceous earth. The filtrate is concentrated under reduced pressure, and the resulting residue is purified by flash chromatography over silica gel, eluting with 80% EtOAc in hexanes, to obtain the title compound (0.5 g) as a mixture of stereoisomers. The material is dissolved in MeOH (5 mL) and is subjected to preparative chiral HPLC (CHIRALPAK® IA, 30×250 mm, using 40/60 ACN/MeOH as the mobile phase, flow rate 30 mL/min) by injecting 1 mL portions of solution and repeating until all the material has been subjected to chiral purification. For each purification run, the first eluting peak is collected. The combined desired fractions are concentrated under reduced pressure to obtain the title compound (94.0 mg, 25% yield). $^1$H NMR (400 MHz, DMSO-d$_6$) δ 1.39 (s, 9H), 1.43 (d, J=6.4 Hz, 3H), 3.67 (dd, J=8.3, 5.7 Hz, 1H), 4.28-4.04 (m, 3H), 7.27 (ddd, J=8.2, 2.2, 0.8 Hz), 7.38 (ddd, J=8.1, 2.0, 0.8 Hz, 1H), 7.51 (t, J=8.5 Hz, 1H), 7.57 (t, J=2.1 Hz, 1H), 7.88 (d, J=6.1 Hz, 1H), 7.96 (s, 1H), 8.42 (s, 1H), 9.25 (s, 2H). ES/MS m/z 467.0 [M−H].

Preparation 99 tert-butyl 3-[[6-(2-chloropyrimidin-5-yl)pyrazin-2-yl]amino]azetidine-1-carboxylate

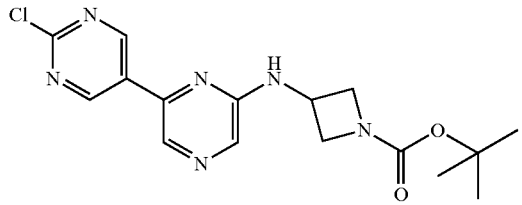 [SMILES: CC(C)(C)OC(=O)N1CC(Nc2cncc(-c3cnc(Cl)nc3)n2)C1]

Nitrogen is bubbled subsurface through a 2 M solution of aqueous NaHCO$_3$ (50 mL) and 1,4-dioxane (126 mL) for 20 min in a round-bottom flask, and tert-butyl 3-[(6-bromopyrazin-2-yl)amino]azetidine-1-carboxylate (8.9 g, 27.2 mmol), (2-chloropyrimidin-5-yl)boronic acid (4.0 g, 25.3 mmol) and [1,1'-bis(di-t-butylphosphino)ferrocene]dichloropalladium(II) (0.5 g, 0.7 mmol) are added under a nitrogen atmosphere. The flask is fitted with a reflux condenser and heated in an aluminum heat block at 70° C. overnight. The reaction mixture is diluted with 800 mL EtOAc and heated to boiling with stirring for ~15 min. The mixture is hot filtered over a bed of diatomaceous earth. The filtrate is partially concentrated under reduced pressure to ~300 mL, and hexanes (~200 mL) are added dropwise to the stirred suspension. The resulting light yellow precipitate is isolated by filtration and dried under reduced pressure to obtain the title compound (5.6 g, 61% yield). ES/MS m/z ($^{35}$Cl/$^{37}$Cl) 385.0/387.0 [M+Na].

Preparation 100 tert-butyl 3-[[6-[2-[(6-methyl-2-pyridyl)amino]pyrimidin-5-yl]pyrazin-2-yl]amino]azetidine-1-carboxylate

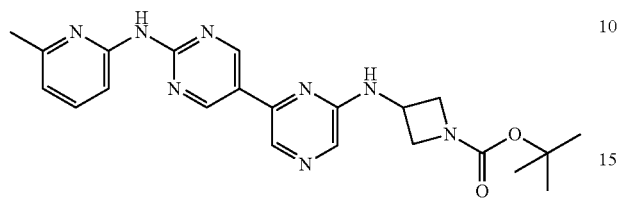

A dry 20 mL vial is charged with tert-butyl 3-[[6-(2-chloropyrimidin-5-yl)pyrazin-2-yl]amino]azetidine-1-carboxylate (0.75 g, 2.1 mmol), 2-amino-6-methylpryidine (0.27 g, 2.5 mmol), $K_2CO_3$ (0.7 g, 5.2 mmol), tert-butanol (10.3 mL), and [(2-di-tert-butylphosphino-3,6-dimethoxy-2',4',6'-triisopropyl-1,1'-biphenyl)-2-(2'-amino-1,1'-biphenyl)]palladium(II) methanesulfonate (0.092 g, 0.1 mmol). The vial is capped and dry nitrogen is bubbled subsurface for 15 min. The vial is heated in a microwave reactor for 45 min at 120° C. The reaction mixture is diluted with water and extracted with EtOAc (3×15 mL). The combined organic extracts are washed with saturated aqueous NaCl, dried over $MgSO_4$, filtered, and concentrated under reduced pressure. The resulting residue is purified by flash chromatography over silica gel, eluting with a gradient of 0 to 20% MeOH in DCM, to obtain the title compound (0.3 g, 37% yield). ES/MS m/z 435.2 [M+H].

Preparation 101

5-bromo-2-[3-(difluoromethoxy)phenoxy]pyrimidine

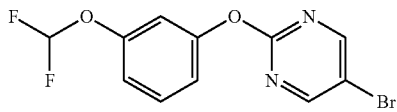 [SMILES: FC(F)Oc1cccc(Oc2ncc(Br)cn2)c1]

A suspension of 5-bromo-2-chloro-pyrimidine (12 g, 63 mmol), 3-(difluoromethoxy)phenol (9.7 g, 58 mmol), $K_2CO_3$ (24 g, 170 mmol) and DIVIF (120 mL) is heated at 80° C. for 1 hour. The reaction is diluted with EtOAc and filtered. The filtrate is concentrated and the resulting residue is purified by silica gel flash column chromatography using 15% EtOAc in hexanes as the eluent to obtain the title compound (16.5 g, 90% Yield) as clear oil. ES/MS m/z ($^{79}$Br/$^{81}$Br) 316.8/318.8 [M+H].

Preparation 102

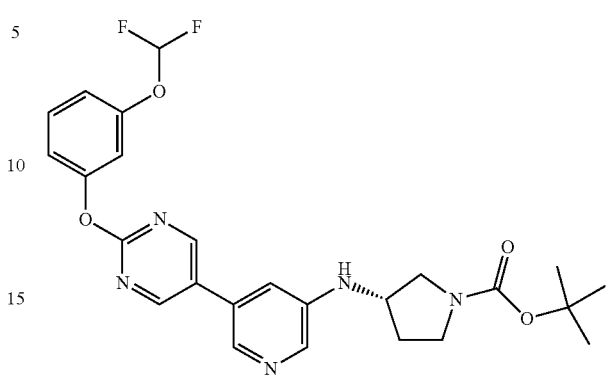

tert-butyl (3S)-3-[[5-[2-[3-(difluoromethoxy)phenoxy]pyrimidin-5-yl]-3-pyridyl]amino]pyrrolidine-1-carboxylate A round bottom flask is charged with 5-bromo-2-[3-difluoromethoxy)phenoxy]pyrimidine (40 g, 113 mmol), bis(pinacolato)diboron (34.6 g, 126 mmol), $K_2OAc$ (27.9 g, 283 mmol), THF (320 mL), (320 mL,), and 1,1'-bis(di-tert-butylphosphino)ferrocene pallidum dichloride (2.26 g, 3.40 mmol). The mixture is purged with nitrogen and is then heated to 60° C. After 1 hour, an aqueous 2 M solution of $K_2CO_3$ (227 mL, 454 mmol) is added, followed by tert-butyl (3S)-3-[(5-bromo-3-pyridyl)amino]pyrrolidine-1-carboxylate (39.7 g, 113.5 mmol). After 1 hour, the mixture is cooled to RT and diluted with EtOAc (200 mL). The organic layer is isolated, dried over $MgSO_4$, filtered, and concentrated. The resulting residue is purified by silica gel flash column chromatography, using a gradient of 50% to 100% EtOAc in hexanes. Impure fractions are further purified silica gel flash column chromatography, using 10% ACN in EtOAc. The pure fractions are combined to obtain the title compound (36 g, 63% yield) as a white solid. ES/MS m/z 316.8/318.8 [M+H].

Example 1

1-[4-[[5-[2-(3-chlorophenoxy)pyrimidin-5-yl]-3-pyridyl]amino]-1-piperidyl]prop-2-en-1-one

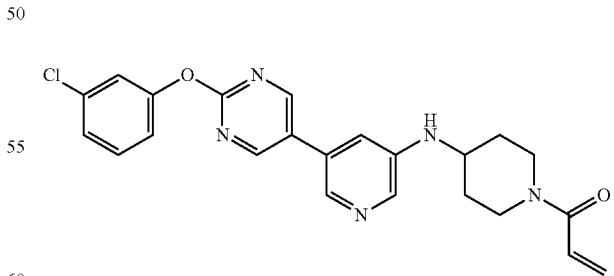

A solution of tert-butyl 4-[[5-[2-(3-chlorophenoxy)pyrimidin-5-yl]-3-pyridyl]amino]piperidine-1-carboxylate (400 mg, 0.9 mmol) in DCM (4.6 mL) under a nitrogen atmosphere is cooled in an ice bath to 0° C. TFA (3.5 mL, 46.0 mmol) is added dropwise via an addition funnel. The resulting suspension is stirred for 90 min at 0° C., and the solution is concentrated under reduced pressure. The resulting residue is suspended in DCM (18 mL), N,N-diisopropylamine (0.95 mL, 5.5 mmol) is added, and the resulting mixture is cooled to −78° C. under a nitrogen atmosphere. Acryloyl chloride (77 μL, 0.9 mmol) in 2 mL of DCM is added dropwise. The resulting suspension is stirred at −78° C. for 15 minutes. The reaction mixture is warmed to RT, diluted with saturated aqueous NaHCO$_3$, and the resulting mixture is extracted with DCM (3×20 mL). The combined organic extracts are washed with saturated aqueous NaCl, dried over MgSO$_4$, filtered, and concentrated under reduced pressure. The residue is purified by silica gel flash column chromatography using a gradient of 0 to 20% methanol in dichloromethane to obtain the title compound (148 mg, 37% yield) MS m/z ($^{35}$Cl/$^{37}$Cl) 436.2/438.2 [M+H].

An alternative preparation of Example 1 is as follows. A suspension of tert-butyl 4-[[5-[2-(3-chlorophenoxy)pyrimidin-5-yl]-3-pyridyl]amino]piperidine-1-carboxylate (20.0 g, 41.5 mmol) is slurried in 2-methyltetrahydrfuran (0.1 L) for several minutes. A solution of aqueous HCl (5M, 33 mL, 170 mmol) is added. The solids dissolve to form a clear brown solution. After several minutes, the solution is warmed to 50° C. and is stirred at that temperature for approximately 1 hour. The solution is cooled to 25° C. in a cool water bath. Water (60 mL) and aqueous potassium carbonate (6.0 M, 55 mL, 330 mmol) are added sequentially. After a few minutes, 3-chloropropionyl chloride (6.0 mL, 63 mmol) is added to the rapidly stirring mixture over two minutes. After 10 minutes, additional, 3-chloropropionyl chloride (1.0 mL, 11 mmol) is added. The mixture is allowed to separate to a biphasic mixture. The suspension is diluted in isopropyl acetate (0.2 L) and water and partitioned. The aqueous layer is re-extracted with isopropyl acetate (0.1 L). The combined organics are washed with aqueous potassium carbonate (2M, 50 mL). Residual tar residue is dissolved in MeOH and combined with the organics layer, which is then concentrated under reduced pressure at 50° C. to approximately 0.2 L. To the cloudy suspension sodium trifluoroacetate (7 g, 50 mmol) and 1,8-diazabicyclo[5.4.0]undec-7-ene (16 mL 107 mmol) are added sequentially. The tarry residue is slowly consumed and a fine solid suspension is observed. The mixture is washed with water (0.15 L). The isolated aqueous layer which contained an oil is back-extracted with isopropyl acetate (0.1 L) and ethyl acetate (0.1 L). The combined organics are washed with water (0.1 L) and then twice with aqueous K$_2$HPO$_4$ (2.0 M, 0.1 L). The solution is concentrated under reduced pressure to ~200 mL and poured onto an ethyl acetate washed silica pad (4×6 cm). The initital filtrate is discarded and the pad washed using 3×0.25 L portions of 20% ethanol in dichloromethane. Fractions 2 and 3 are combined. The eluents are concentrated under reduced pressure to ~45 g. The clear yellow solution is stirred at RT. A seed crystal is added followed by addition of heptane (0.1 L) over 1.15 hours. The mixture is warmed to 60° C. for 1 hour, heating is removed and the mixture allowed to cool overnight. The white solid is isolated by vacuum filtration to yield the title compound (10.5 g, 23.6 mmol, 57% yield.)

The following compounds are prepared essentially by the first method of Example 1, using the appropriately substituted carbamate and acryloyl chloride.

| Example | Structure | Name | ESMS m/z [M + H] |
|---|---|---|---|
| 2 | 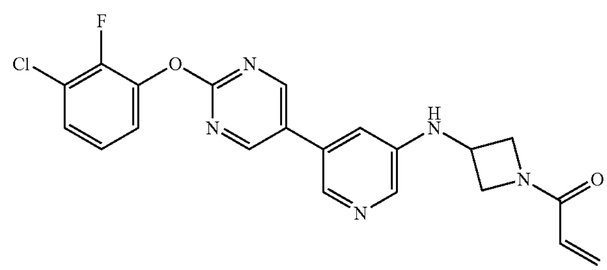 [SMILES: C=CC(=O)N1CC(Nc2cncc(-c3cnc(Oc4cccc(Cl)c4F)nc3)c2)C1] | 1-[3-[[5-[2-(3-chloro-2-fluoro-phenoxy)pyrimidin-5-yl]-3-pyridyl]amino]azetidin-1-yl]prop-2-en-1-one | ($^{35}$Cl/$^{37}$Cl) 426.2/428.2 |
| 3 | 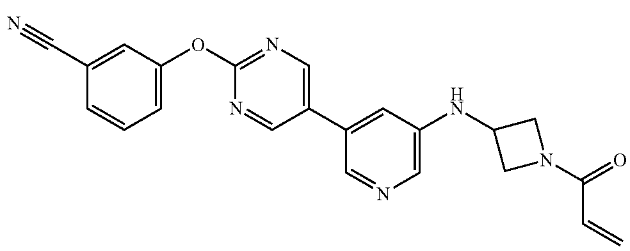 [SMILES: C=CC(=O)N1CC(Nc2cncc(-c3cnc(Oc4cccc(C#N)c4)nc3)c2)C1] | 3-[5-[5-[(1-prop-2-enoylazetidin-3-yl)amino]-3-pyridyl]pyrimidin-2-yl]oxybenzonitrile | 345.0 |
| 4 | 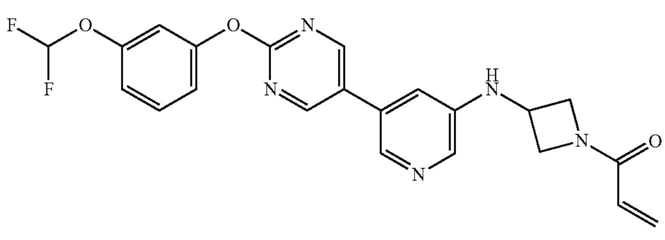 [SMILES: C=CC(=O)N1CC(Nc2cncc(-c3cnc(Oc4cccc(OC(F)F)c4)nc3)c2)C1] | 1-[3-[[5-[2-[3-(difluoromethoxy)phenoxy]pyrimidin-5-yl]-3-pyridyl]amino]azetidin-1-yl]prop-2-en-1-one | 440.0 |

-continued

| Example | Structure | Name | ESMS m/z [M + H] |
|---|---|---|---|
| 5 | 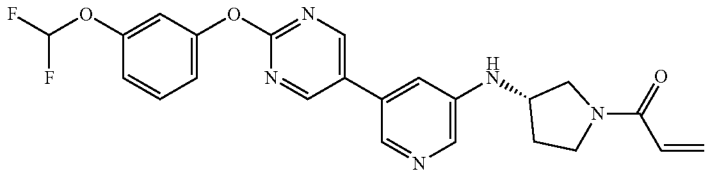 [SMILES: C=CC(=O)N1CC[C@H](Nc2cncc(-c3cnc(Oc4cccc(OC(F)F)c4)nc3)c2)C1] | 1-[(3S)-3-[[5-[2-[3-(difluoromethoxy)phenoxy]pyrimidin-5-yl]-3-pyridyl]amino]pyrrolidin-1-yl]prop-2-en-1-one | 400.0 |
| 6 | 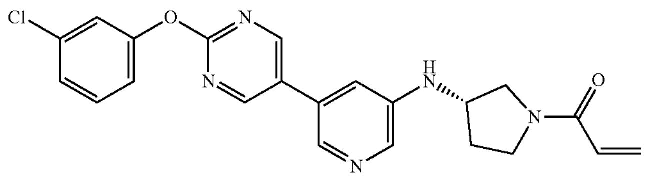 [SMILES: C=CC(=O)N1CC[C@H](Nc2cncc(-c3cnc(Oc4cccc(Cl)c4)nc3)c2)C1] | 1-[(3S)-3-[[5-[2,-(3-chlorophenoxy)pyrimidin-5-yl]-3-pyridyl]amino]pyrrolidin-1-yl]prop-2-en-1-one | ($^{35}$Cl/$^{37}$Cl) 422.2/424.2 |
| 7 | 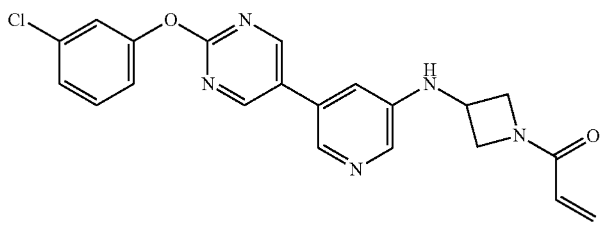 [SMILES: C=CC(=O)N1CC(Nc2cncc(-c3cnc(Oc4cccc(Cl)c4)nc3)c2)C1] | 1-[3-[[5-[2-(3-chlorophenoxy)pyrimidin-5-yl]-3-pyridyl]amino]azetidin-1-yl]prop-2-en-1-one | ($^{35}$Cl/$^{37}$Cl) 408.0/410.0 |
| 8 | 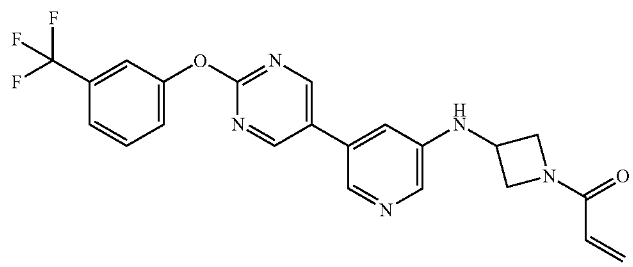 [SMILES: C=CC(=O)N1CC(Nc2cncc(-c3cnc(Oc4cccc(C(F)(F)F)c4)nc3)c2)C1] | 1-[3-[[5-[2-[3-(trifluoromethyl)phenoxy]pyrimidin-5-yl]-3-pyridyl]amino]azetidin-1-yl]prop-2-en-1-one | 442.1 |
| 9 | 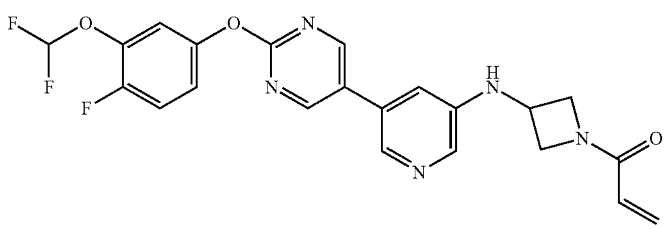 [SMILES: C=CC(=O)N1CC(Nc2cncc(-c3cnc(Oc4ccc(F)c(OC(F)F)c4)nc3)c2)C1] | 1-[3-[[5-[2-[3-(difluoromethoxy)-4-fluoro-phenoxy]pyrimidin-5-yl]-3-pyridyl]amino]azetidin-1-yl]prop-2-en-1-one | 458.1 |
| 10 | 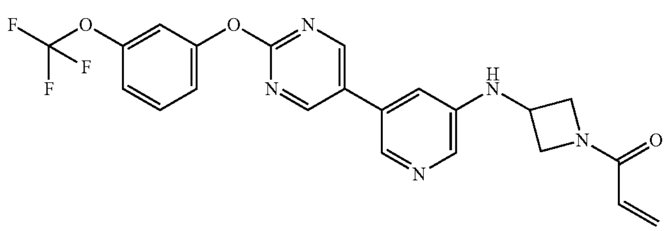 [SMILES: C=CC(=O)N1CC(Nc2cncc(-c3cnc(Oc4cccc(OC(F)(F)F)c4)nc3)c2)C1] | 1-[3-[[5-[2-[3-(trifluoromethoxy)phenoxy]pyrimidin-5-yl]-3-pyridyl]amino]azetidin-1-yl]prop-2-en-1-one | 458.0 |
| 11 | 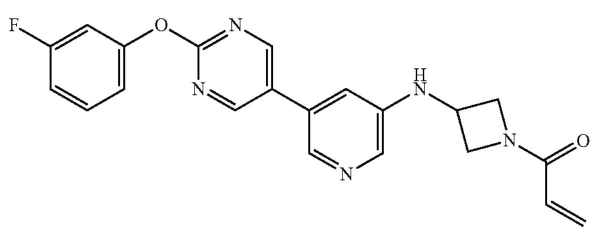 [SMILES: C=CC(=O)N1CC(Nc2cncc(-c3cnc(Oc4cccc(F)c4)nc3)c2)C1] | 1-[3-[[5-[2-(3-fluorophenoxy)pyrimidin-5-yl]-3-pyridyl]amino]azetidin-1-yl]prop-2-en-1-one | 392.2 |

-continued

| Example | Structure | Name | ESMS m/z [M + H] |
|---|---|---|---|
| 12 | 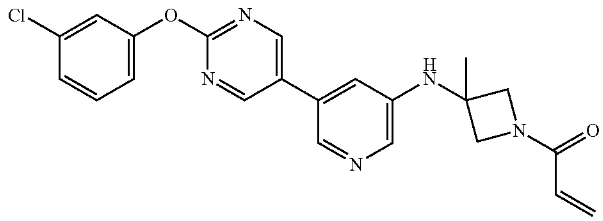 [SMILES: C=CC(=O)N1CC(C)(Nc2cncc(-c3cnc(Oc4cccc(Cl)c4)nc3)c2)C1] | 1-[3-[[5-[2-(3-chlorophenoxy)pyrimidin-5-yl]-3-pyridyl]amino]-3-methyl-azetidin-1-yl]prop-2-en-1-one | ($^{35}$Cl/$^{37}$Cl) 422.0/424.0 |
| 13 | 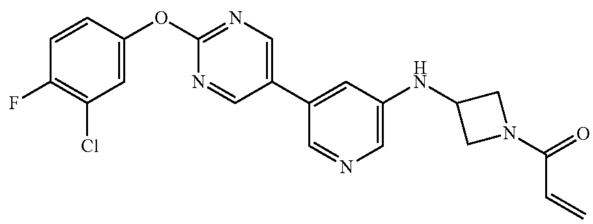 [SMILES: C=CC(=O)N1CC(Nc2cncc(-c3cnc(Oc4ccc(F)c(Cl)c4)nc3)c2)C1] | 1-[3-[[5-[2-(3-chloro-4-fluoro-phenoxy)pyrimidin-5-yl]-3-pyridyl]amino]azetidin-1-yl]prop-2-en-1-one | ($^{35}$Cl/$^{37}$Cl) 426.0/428.0 |
| 14 | 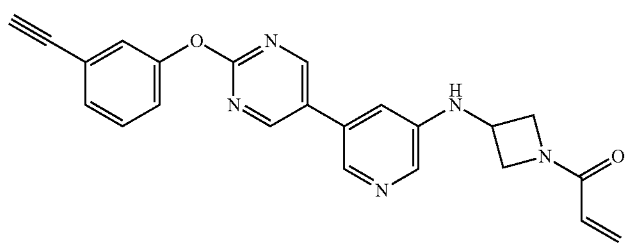 [SMILES: C#Cc1cccc(Oc2ncc(-c3cncc(NC4CN(C(=O)C=C)C4)c3)cn2)c1] | 1-[3-[[5-[2-(3-ethynylphenoxy)pyrimidin-5-yl]-3-pyridyl]amino]azetidin-1-yl]prop-2-en-1-one | 398.2 |
| 15 | 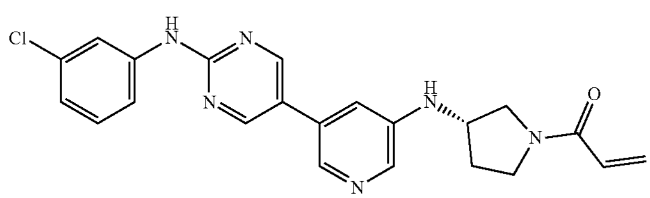 [SMILES: C=CC(=O)N1CC[C@H](Nc2cncc(-c3cnc(Nc4cccc(Cl)c4)nc3)c2)C1] | 1-[3-[[5-[2-(3-chloroanilino)pyrimidin-5-yl]-3-pyridyl]amino]azetidin-1-yl]prop-2-en-1-one | ($^{35}$Cl/$^{37}$Cl) 421.2/423.2 |
| 16 | 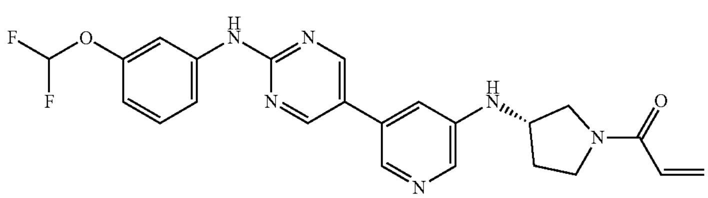 [SMILES: C=CC(=O)N1CC[C@H](Nc2cncc(-c3cnc(Nc4cccc(OC(F)F)c4)nc3)c2)C1] | (S)-1-(3-((5-(2-((3-(difluoromethoxy)phenyl)amino)pyrimidin-5-yl)pyridin-3-yl)amino)pyrrolidin-1-yl)prop-2-en-1-one | 452.5 |
| 17 | 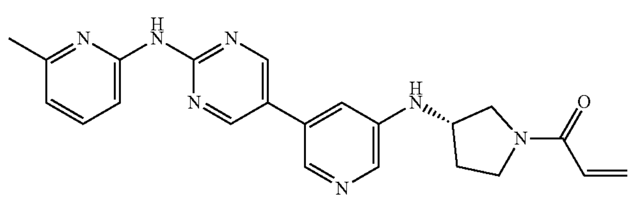 [SMILES: C=CC(=O)N1CC[C@H](Nc2cncc(-c3cnc(Nc4cccc(C)n4)nc3)c2)C1] | 1-{(3S)-3-[[5-{2-[(6-methylpyridin-2-yl)amino]pyrimidin-5-yl}pyridin-3-yl]amino]pyrrolidin-1-yl}prop-2-en-1-one | 401.5 |
| 18 | 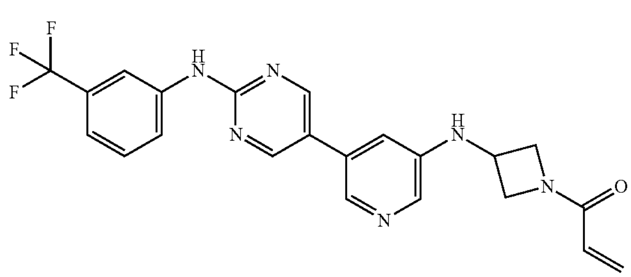 [SMILES: C=CC(=O)N1CC(Nc2cncc(-c3cnc(Nc4cccc(C(F)(F)F)c4)nc3)c2)C1] | 1-[3-[[5-[2-[3-(trifluoromethyl)anilino]pyrimidin-5-yl]-3-pyridyl]amino]azetidin-1-yl]prop-2-en-1-one | 441.2 |

| Example | Structure | Name | ESMS m/z [M + H] |
|---|---|---|---|
| 19 | 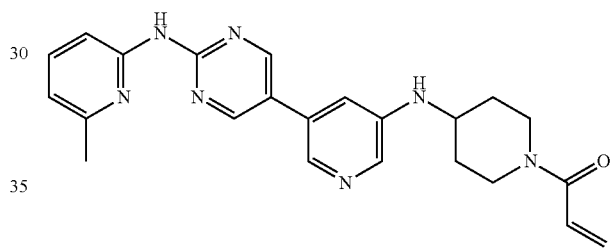 | 1-[4-[[5-[2-(3-chloroanilino)pyrimidin-5-yl]-3-pyridyl]amino]-1-piperidyl]prop-2-en-1-one | ($^{35}$Cl/$^{37}$Cl) 435.0/437 |

Alternative Procedure for Example 5

1-[(3S)-3-[[5-[2-[3-(difluoromethoxy)phenoxy]pyrimidin-5-yl]-3-pyridyl]amino]pyrrolidin-1-yl]prop-2-en-1-one

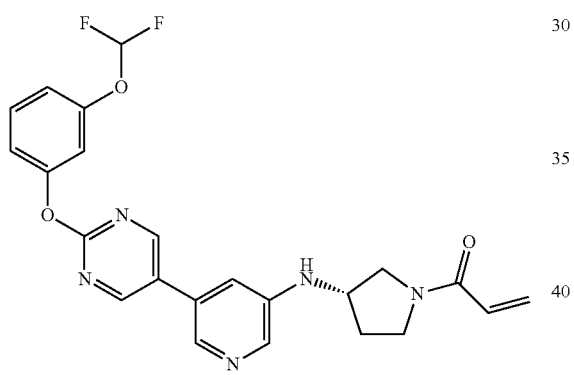

A round bottom flask is charged with tert-butyl (3S)-3-[[5-[2-[3-(difluoromethoxy)phenoxy]pyrimidin-5-yl]-3-pyridyl]amino]pyrrolidine-1-carboxylate (36 g, 72 mmol), DCM(144 mL), and TFA (38.1 mL, 505 mmol), and the resulting mixture is stirred at 40° C. After 4 hours, heating is removed and the reaction is stirred to RT overnight. The mixure is cooled to 0° C. A solution of TEA (111 mL, 793 mmol) in EtOAc (288 mL), acrylic acid (5.92 mL, 86.5 mmol), and 2,4,6-tripropyl-1,3,5,2,4,6-trioxatriphosphorinane-2,4,6-trioxide (1.68 mol/L in EtOAC, 60.1 mL, 101 mmol) are added sequentially. Cooling is removed and the reaction is stirred at RT for 1 hour. The solution is washed with saturated aqueous NaHCO$_3$ (300 mL). The organic layer is separated, dried over MgSO$_4$, filtered, and concentrated to dryness. The residue is purified by silica gel flash column chromatography, using a gradient of 0 to 10% EtOH in EtOAc, to obtain the title compound (13.2 g, 39.2% Yield) as a white foam. ES/MS m/z 453.8 [M+H].

Example 20

1-[4-[[5-[2-[(6-methyl-2-pyridyl)amino]pyrimidin-5-yl]-3-pyridyl]amino]-1-piperidyl]prop-2-en-1-one A solution of tert-butyl 4-[[5-[2-[(6-methyl-2-pyridyl)amino]pyrimidin-5-yl]-3-pyridyl]amino]piperidine-1-carboxylate (0.39 g, 0.85 mmol) in dichloromethane (4.2 mL) is cooled in an ice bath to 0° C. under a nitrogen atmosphere. Trifluoroacetic acid (3.2 mL, 42 mmol) is added dropwise via an addition funnel. The suspension is stirred for 90 minutes at 0° C. The solution is concentrated in vacuo. The residue is suspended in ethyl acetate (4.2 mL) and cooled to 0° C. under a nitrogen atmosphere. Acrylic acid (0.070 mL, 1.02 mmol) is added followed by a solution 1-propanephosphonic anhydride in acetonitrile (50 mass %, 0.71 mL, 1.2 mmol). After 15 minutes, the reaction is diluted with water and the resulting suspension is stirred for 5 minutes. The mixture is extracted with ethyl acetate (150 mL then 2×100 mL). The combined organic are washed with saturated aqueous sodium bicarbonate and saturated aqueous sodium chloride. The organic layer is dried over MgSO$_4$, filtered and concentrated under reduced pressure. The resulting residue is purified by silica gel flash column chromatography using 10% methanol in dichloromethane as the eluent to yield 1-[4-[[5-[2-[(6-methyl-2-pyridyl)amino]pyrimidin-5-yl]-3-pyridyl]amino]-1-piperidyl]prop-2-en-1-one (0.082 g, 0.197 mmol, 23% yield). MS m/z 416.2 [M+H]

The following compounds are prepared essentially by the method of Example 20:

| Example | Structure | Name | ESMS m/z [M + H] |
|---|---|---|---|
| 21 | 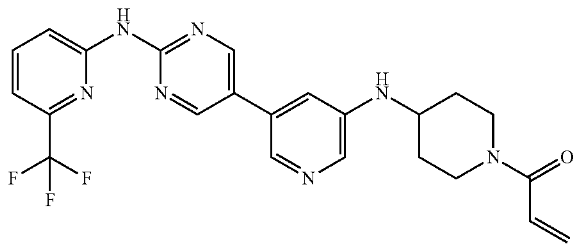 [SMILES: C=CC(=O)N1CCC(Nc2cncc(-c3cnc(Nc4cccc(C(F)(F)F)n4)nc3)c2)CC1] | 1-[4-[[5-[2-[[6-(trifluoromethyl)-2-pyridyl]amino]pyrimidin-5-yl]-3-pyridyl]amino]-1-piperidyl]prop-2-en-1-one | 470.2 |
| 22 | 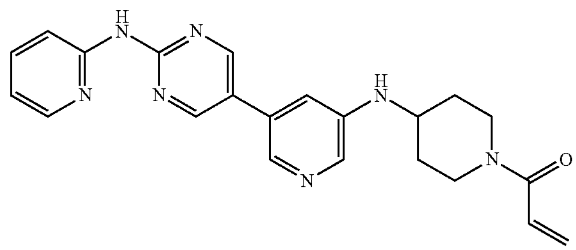 [SMILES: C=CC(=O)N1CCC(Nc2cncc(-c3cnc(Nc4ccccn4)nc3)c2)CC1] | 1-[4-[[5-[2-(2-pyridylamino)pyrimidin-5-yl]-3-pyridyl]amino]-1-piperidyl]prop-2-en-1-one | 402.2 |

Example 23

(E)-1-[4-[[5-[2-(3-chloroanilino)pyrimidin-5-yl]-3-pyridyl]amino]-1-piperidyl]-4-(dimethylamino)but-2-en-1-one

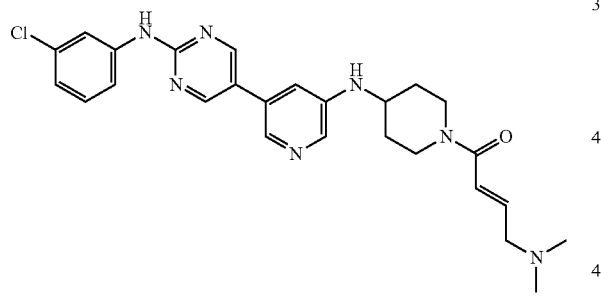

A 50 mL round-bottom flask equipped with addition funnel is charged with tert-butyl 4-[[5-[2-(3-chloroanilino)pyrimidin-5-yl]-3-pyridyl]amino]piperidine-1-carboxylate (0.40 g, 0.83 mmol) and dichloromethane (4.2 mL). The vessel is cooled in an ice bath to 0° C. under a nitrogen atmosphere. Trifluoroacetic acid (3.4 mL, 45 mmol) is added dropwise via the addition funnel and the solution is then stirred for 15 minutes. The suspension is removed from the cooling bath and is concentrated under reduced pressure. The residue is suspended in 1 mL of N,N-dimethylformamide and is added to solution formed by sequential addition of (2E)-4-(dimethylamino)but-2-enoic acid hydrogen chloride (0.17 g, 1.0 mmol) and HATU (0.36 g, 0.98 mmol) in N,N-dimethylformamide (4.2 mL). N,N-Diisopropylethylamine (1.45 mL, 8.30 mmol) is then added to the reaction mixture. The solution is stirred at RT for 20 minutes. The mixture is diluted with aqueous saturated NaHCO$_3$ and then extracted with ethyl acetate (3×15 mL). Combined organics are washed with saturated aqueous NaCl, dried over MgSO$_4$, filtered and concentrated under reduced pressure. The residue is purified by silica gel flash column chromatography using a gradient of 5 to 25% methanol in dichloromethane to yield (E)-1-[4-[[5-[2-(3-chloroanilino)pyrimidin-5-yl]-3-pyridyl]amino]-1-piperidyl]-4-(dimethylamino)but-2-en-1-one (0.25 g, 0.52 mmol, 62% yield). ES/MS m/z ($^{35}$Cl/$^{37}$Cl) 494.4/494.4 [M+H]

Example 24

1-[3-[[6-[2-[3-(difluoromethoxy)phenoxy]pyrimidin-5-yl]pyrazin-2-yl]amino]azetidin-1-yl]prop-2-en-1-one

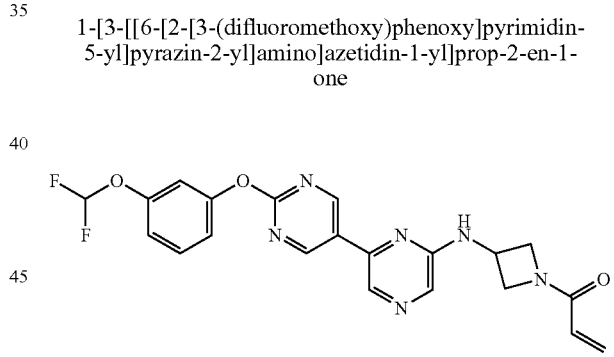

TFA (2.7 mL, 36.0 mmol) is added to a solution of tert-butyl 3-[[6-[2-[3-(difluoromethoxy)phenoxy]pyrimidin-5-yl]pyrazin-2-yl]amino]azetidine-1-carboxylate (0.4 g, 0.9 mmol) in anhydrous DCM (2.6 mL) at RT. After stirring for 1 h, the reaction is concentrated under reduced pressure to a dark oil. The residue is suspended in anhydrous DCM (18 mL) and TEA (0.9 mL, 6.3 mmol). The resulting mixture is stirred at RT and then placed in a −78° C. cooling bath. Acryloyl chloride (0.08 mL, 1.0 mmol) is added dropwise. The reaction mixture is stirred at −78° C. for 30 min. Water (0.5 mL) is added at reduced temperature and the solution is allowed to warm to about 0° C. The solution is directly loaded onto silica gel for purification by flash chromatography, eluting with 7% MeOH in DCM, to obtain the title compound (0.13 g, 32% yield) ES/MS m/z 441.0 [M+H].

The following compounds are prepared essentially by the method of Example 24, using the appropriately substituted carbamate and acryloyl chloride.

| Example | Structure | Name | ES/MS m/z [M + H] |
|---|---|---|---|
| 25 | 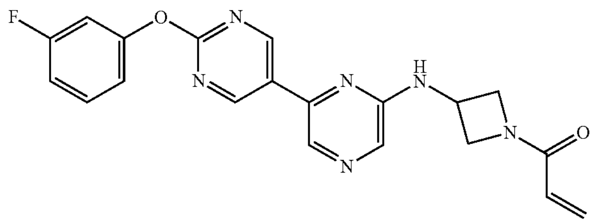 [SMILES: C=CC(=O)N1CC(Nc2cncc(-c3cnc(Oc4cccc(F)c4)nc3)n2)C1] | 1-[3-[[6-[2-(3-fluorophenoxy)pyrimidin-5-yl]pyrazin-2-yl]amino]azetidin-1-yl]prop-2-en-1-one | 393.0 |
| 26 | 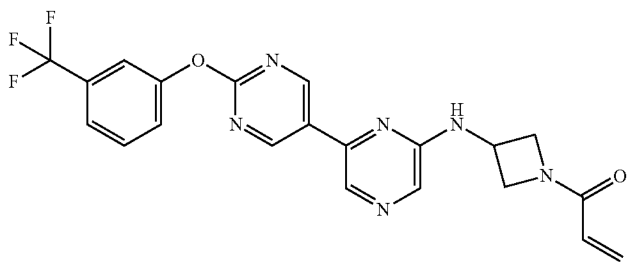 [SMILES: C=CC(=O)N1CC(Nc2cncc(-c3cnc(Oc4cccc(C(F)(F)F)c4)nc3)n2)C1] | 1-[3-[[6-[2-[3-(trifluoromethyl)phenoxy]pyrimidin-5-yl]pyrazin-2-yl]amino]azetidin-1-yl]prop-2-en-1-one | 443.0 |
| 27 | 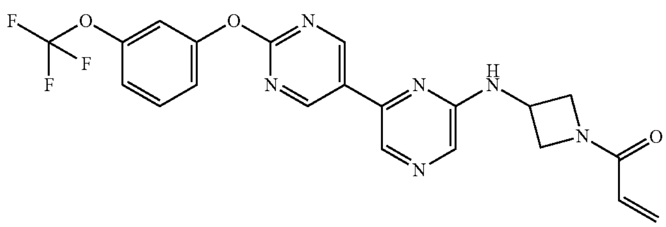 [SMILES: C=CC(=O)N1CC(Nc2cncc(-c3cnc(Oc4cccc(OC(F)(F)F)c4)nc3)n2)C1] | 1-[3-[[6-[2-[3-(trifluoromethoxy)phenoxy]pyrimidin-5-yl]pyrazin-2-yl]amino]azetidin-1-yl]prop-2-en-1-one | 459.1 |
| 28 | 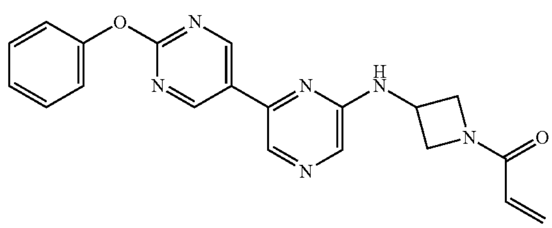 [SMILES: C=CC(=O)N1CC(Nc2cncc(-c3cnc(Oc4ccccc4)nc3)n2)C1] | 1-[3-[[6-(2-phenoxypyrimidin-5-yl)pyrazin-2-yl]amino]azetidin-1-yl]prop-2-en-1-one | 375.0 |
| 29 | 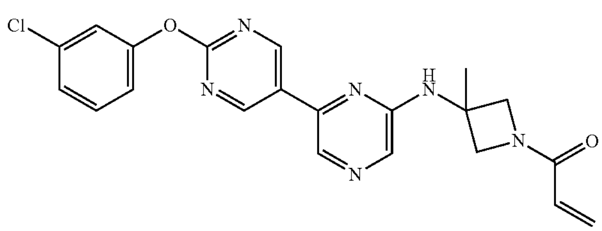 [SMILES: C=CC(=O)N1CC(C)(Nc2cncc(-c3cnc(Oc4cccc(Cl)c4)nc3)n2)C1] | 1-[3-[[6-[2-(3-chlorophenoxy)pyrimidin-5-yl]pyrazin-2-yl]amino]-3-methyl-azetidin-1-yl]prop-2-en-1-one | ($^{35}$Cl/$^{37}$Cl) 423.2 |
| 30 | 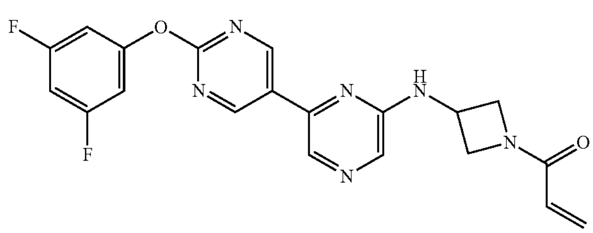 [SMILES: C=CC(=O)N1CC(Nc2cncc(-c3cnc(Oc4cc(F)cc(F)c4)nc3)n2)C1] | 1-[3-[[6-[2-(3,5-difluorophenoxy)pyrimidin-5-yl]pyrazin-2-yl]amino]azetidin-1-yl]prop-2-en-1-one | 411.1 |

| Example | Name | ES/MS m/z [M + H] |
|---|---|---|
| 31 | 1-[3-[[6-[2-(3-chlorophenoxy)pyrimidin-5-yl]pyrazin-2-yl]amino]azetidin-1-yl]prop-2-en-1-one | ($^{35}$Cl/$^{37}$Cl) 409.1/411.1 |
| 32 | 1-[(2S,3R)-3-[[6-[2-(3-chlorophenoxy)pyrimidin-5-yl]pyrazin-2-yl]amino]-2-methyl-azetidin-1-yl]prop-2-en-1-one, Isomer 1 | ($^{35}$Cl/$^{37}$Cl) 423.1/425.1 |
| 33 | 1-[(3S)-3-[[6-[2-[3-(trifluoromethoxy)anilino]pyrimidin-5-yl]pyrazin-2-yl]amino]pyrrolidin-1-yl]prop-2-en-1-one | 472.4 |
| 34 | 1-[(3S)-3-[[6-[2-(3-chloroanilino)pyrimidin-5-yl]pyrazin-2-yl]amino]pyrrolidin-1-yl]prop-2-en-1-one | ($^{35}$Cl/$^{37}$Cl) 422.2/424.2 |
| 35 | 1-[3-[[6-[2-(3-chloro-4-fluoro-anilino)pyrimidin-5-yl]pyrazin-2-yl]amino]azetidin-1-yl]prop-2-en-1-one | ($^{35}$Cl/$^{37}$Cl) 426.0/428.0 |
| 36 | 1-[(3S)-3-[[6-[2-[2-(trifluoromethoxy)anilino]pyrimidin-5-yl]pyrazin-2-yl]amino]pyrrolidin-1-yl]prop-2-en-1-one | 472.0 |

-continued

| Example | Structure | Name | ES/MS m/z [M + H] |
|---|---|---|---|
| 37 | 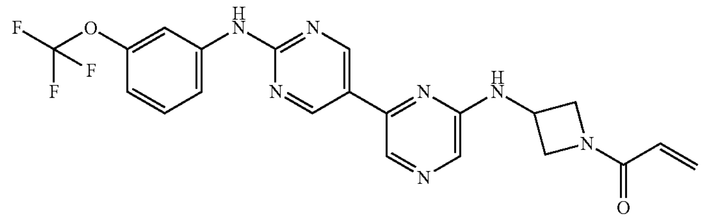 [SMILES: C=CC(=O)N1CC(Nc2cncc(-c3cnc(Nc4cccc(OC(F)(F)F)c4)nc3)n2)C1] | 1-[3-[[6-[2-[3-(trifluoromethoxy)anilino]pyrimidin-5-yl]pyrazin-2-yl]amino]azetidin-1-yl]prop-2-en-1-one | 458.2 |
| 38 | 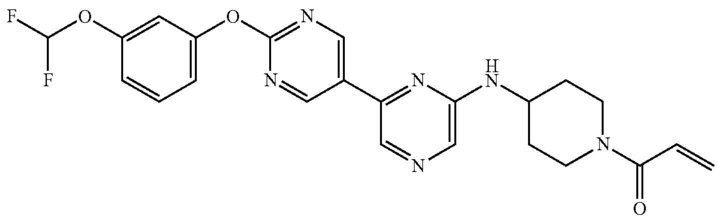 [SMILES: C=CC(=O)N1CCC(Nc2cncc(-c3cnc(Oc4cccc(OC(F)F)c4)nc3)n2)CC1] | 1-[4-[[6-[2-[3-(difluoromethoxy)phenoxy]pyrimidin-5-yl]pyrazin-2-yl]amino]-1-piperidyl]prop-2-en-1-one | 469.2 |
| 39 | 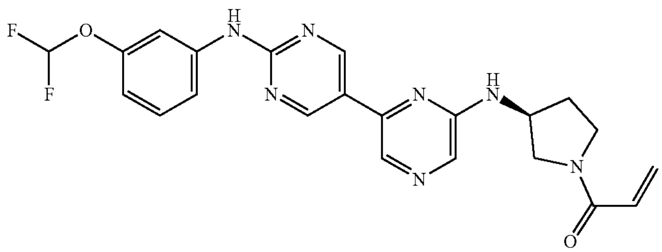 [SMILES: C=CC(=O)N1CC[C@H](Nc2cncc(-c3cnc(Nc4cccc(OC(F)F)c4)nc3)n2)C1] | 1-[(3S)-3-[[6-[2-[3-(difluoromethoxy)anilino]pyrimidin-5-yl]pyrazin-2-yl]amino]pyrrolidin-1-yl]prop-2-en-1-one | 454.2 |
| 40 | 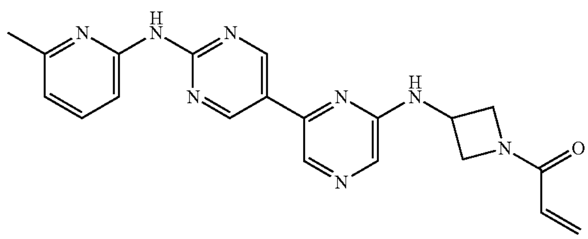 [SMILES: C=CC(=O)N1CC(Nc2cncc(-c3cnc(Nc4cccc(C)n4)nc3)n2)C1] | 1-[3-[[6-[2-[(6-methyl-2-pyridyl)amino]pyrimidin-5-yl]pyrazin-2-yl]amino]azetidin-1-yl]prop-2-en-1-one | 389.2 |
| 41 | 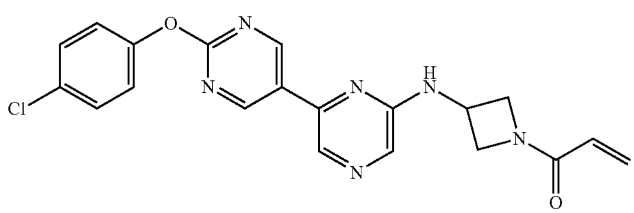 [SMILES: C=CC(=O)N1CC(Nc2cncc(-c3cnc(Oc4ccc(Cl)cc4)nc3)n2)C1] | 1-[3-[[6-[2-(4-chlorophenoxy)pyrimidin-5-yl]pyrazin-2-yl]amino]azetidin-1-yl]prop-2-en-1-one | ($^{35}$Cl/$^{37}$Cl) 409.1/411.2 |
| 42 | 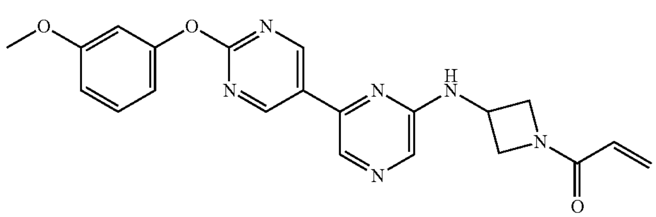 [SMILES: C=CC(=O)N1CC(Nc2cncc(-c3cnc(Oc4cccc(OC)c4)nc3)n2)C1] | 1-[3-[[6-[2-(3-methoxyphenoxy)pyrimidin-5-yl]pyrazin-2-yl]amino]azetidin-1-yl]prop-2-en-1-one | 405.0 |

-continued

| Example | Structure | Name | ES/MS m/z [M + H] |
|---|---|---|---|
| 43 | 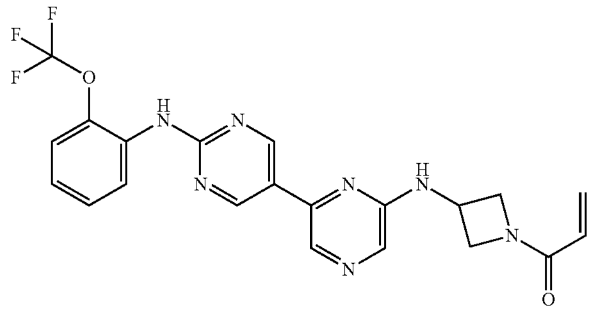 [SMILES: C=CC(=O)N1CC(Nc2cncc(-c3cnc(Nc4ccccc4OC(F)(F)F)nc3)n2)C1] | 1-[3-[[6-[2-[2-(trifluoromethoxy)anilino]pyrimidin-5-yl]pyrazin-2-yl]amino]azetidin-1-yl]prop-2-en-1-one | 458.2 |
| 44 | 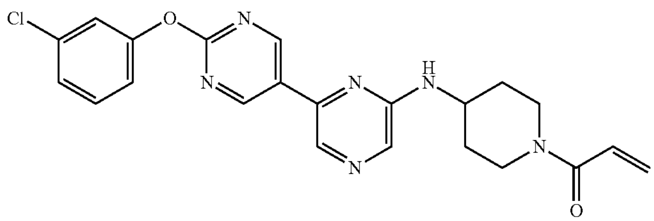 [SMILES: C=CC(=O)N1CCC(Nc2cncc(-c3cnc(Oc4cccc(Cl)c4)nc3)n2)CC1] | 1-[4-[[6-[2-(3-chlorophenoxy)pyrimidin-5-yl]pyrazin-2-yl]amino]-1-piperidyl]prop-2-en-1-one | ($^{35}$Cl/$^{37}$Cl) 437.2/439.2 |

Example 45

(E)-1-[4-[[6-[2-(3-chlorophenoxy)pyrimidin-5-yl]pyrazin-2-yl]amino]-1-piperidyl]-4-(dimethylamino)but-2-en-1-one

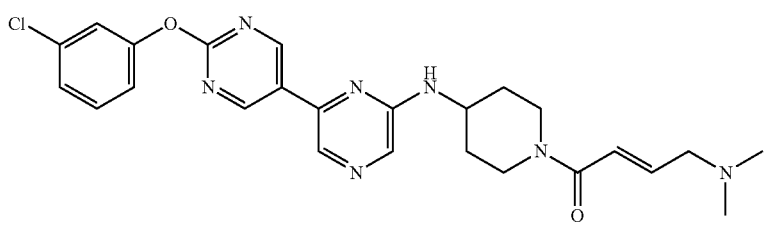 [SMILES: CN(C)C/C=C/C(=O)N1CCC(Nc2cncc(-c3cnc(Oc4cccc(Cl)c4)nc3)n2)CC1]

A 50 mL round-bottom flask equipped with addition funnel is charged with tert-butyl 4-[[6-[2-(3-chlorophenoxy)pyrimidin-5-yl]pyrazin-2-yl]amino]piperidine-1-carboxylate (0.4 g, 0.9 mmol) and DCM (4.5 mL). The vessel is cooled in an ice bath to 0° C. under a nitrogen atmosphere. TFA (3.4 mL, 44.5 mmol) is added dropwise via an addition funnel and the solution is stirred for 15 min. The suspension is removed from the cooling bath and concentrated under reduced pressure. The resulting residue is suspended in 1 mL of DMF and is added to a solution formed by sequential addition of (2E)-4-(dimethylamino)but-2-enoic acid (0.1 g, 1.1 mmol) and HATU (0.4 g, 1.0 mmol) in DMF (4.45 mL). DIPEA (1.6 mL, 8.9 mmol) is added to the reaction mixture and the solution is stirred at RT for 20 min. The mixture is diluted with aqueous saturated NaHCO$_3$ and extracted with EtOAc (3×15 mL). The combined organic extracts are washed with saturated aqueous NaCl, dried over MgSO$_4$, filtered, and concentrated under reduced pressure. The resulting residue is purified by C18 reverse phase liquid chromatography, eluting with a gradient of 40/60 to 70/30 ACN/10 mM NH$_4$HCO$_3$ in water, to obtain the title compound (0.4 g, 81% yield) after solvent evaporation. ES/MS m/z ($^{35}$Cl/$^{37}$Cl) 494.2/496.2 [M+H].

The following compounds are prepared essentially by the method of Example 45, using the appropriately substituted carbamate.

| Example | Structure | Name | ES/MS m/z |
|---|---|---|---|
| 46 | 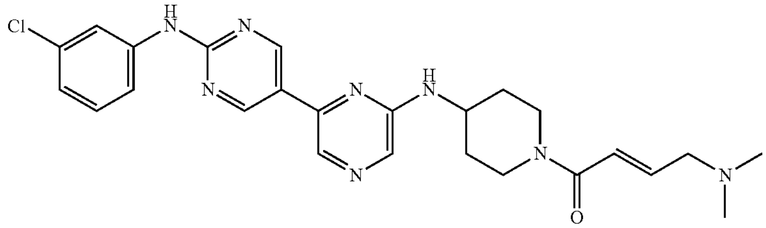 [SMILES: CN(C)C/C=C/C(=O)N1CCC(Nc2cncc(-c3cnc(Nc4cccc(Cl)c4)nc3)n2)CC1] | (E)-1-[4-[[6-[2-(3-chloroanilino)pyrimidin-5-yl]pyrazin-2-yl]amino]-1-piperidyl]-4-(dimethylamino)but-2-en-1-one | ($^{35}$Cl/$^{37}$Cl) 493.2/495.2 |
| 47 | 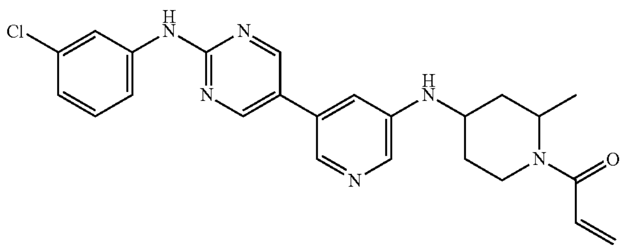 [SMILES: C=CC(=O)N1CCC(Nc2cncc(-c3cnc(Nc4cccc(Cl)c4)nc3)c2)CC1C] | 1-[4-[[5-[2-(3-chloroanilino)pyrimidin-5-yl]-3-pyridyl]amino]-2-methyl-1-pipendyl]prop-2-en-1-one | ($^{35}$Cl/$^{37}$Cl) 449.2/451.2 |

Biological Assays

BTK and EGFR in Vitro Assays:

The BTK and EGFR biochemical assays utilize LANTHASCREEN® Eu Kinase Binding Assays from Thermo Fisher Scientific, measuring the binding of the kinase with a fluorinated tracer. The assay buffer consists of 50 mM HEPES pH 7.5, 0.01% BRU™-35, 10 mM $MgCl_2$, 1 mM EGTA, and 1 mM DTT. The test compounds are diluted and added to the assay plate with a Labcyte ECHO® 555 liquid handler. The compounds are tested in 10 point dose response curves (100 μM-0.005 μM) with a maximum DMSO concentration of 1%. The assays are performed in 20 μL in low-volume 384-well white proxiplates. For the BTK assay, the concentration of full-length His-labeled BTK in the assay is 5 nM, the Eu-anti-His antibody is 2 nM, and the kinase tracer 236 is 60 nM. For the EGFR assay, the concentration of truncated (amino acids 668-1210) GST-labeled EGFR is 5 nM, the Eu-anti-GST antibody is 2 nM, and the kinase tracer 199 is 10 nM. The components of the assay (compound, enzyme/antibody, tracer) are assembled and incubated for 30 min prior to being read on a Perkin-Elmer EnVision with excitation at 340 nM, tracer emission at 665 nM, and antibody emission at 615 nM. The signal ratio is converted to percent inhibition using the following equation: % Inhibition=100−[(Test Compound−Median Minimum)/(Median Maximum−Median Minimum)×100]. The relative $IC_{50}$ is determined by fitting the percent inhibition at each inhibitor concentration to the following equation using Next Generation Results Rel-IC50: Data is analyzed using a 4-paramer nonlinear logistic equation y=(A+((B−A)/(1+((C/x)^D)))) where, y=% specific inhibition, A=bottom of the curve, B=top of the curve, C=relative $IC_{50}$=concentration causing 50% inhibition based on the range of the data from top to bottom, D=Hill Slope=slope of the curve.

Human Whole Blood CD69 in Vitro Assay:

The HWB CD69 assay measures activated B cells in human whole blood using a flow cytometer. Compounds are diluted and added to assay plates with a Labcyte ECHO® 555 liquid handler. Compounds are tested in 10 point dose response curves (20 μM-0.001 μM) in 96-well v-bottom plates with a maximum DMSO concentration of 0.2%. Fresh blood from individual healthy volunteer is mixed with HEPES (0.5 ml HEPES added per 10 ml blood) and 100 μl/well is added to compound plates. The plates are sealed and incubated in a 37° C. incubator for 3 h. Anti-human-IgD-Dextran is added to each well to give a final concentration of 100 ng/ml, mixed, and put back into the incubator. After 1 h, the cells are washed with cold FACS buffer and transferred to a deep well plate. The cells are incubated with anti-human CD69-PE (BIOLEGEND®, clone FN50) and anti-human CD19-APC (BIOLEGEND®, clone HIB19) antibodies on ice for 20 min. The cells are washed and incubated in eBioscience™ 1-step Fix/Lyse solution (10×) at RT to lyse the red blood cells and fix the other cells. The white cells are pelleted and washed in FACS buffer and then brought up in read buffer. The suspended cells are transferred to 96-well round bottom plates and read on an IntelliCyt iQue® Screener Plus flow cytometer. From the SSC (Side Scatter Channel) vs FSC (Forward Scatter Channel) graph, the lymphocytes are identified. Lymphocytes are identified with gated on positive CD19 marker for quantify CD69 (a marker of activated B lymphocytes) MFI (mean fluorescent intensity/cell). The signal ratio is converted to percent inhibition using the following equation: % Inhibition=100−[(Test Compound−Median Min)/(Median Max−Median Min)×100]. The relative $IC_{50}$ is determined by fitting the percent inhibition at each inhibitor concentration to the following equation using Next Generation Results Rel-IC50: Data is analyzed using a 4-paramer nonlinear logistic equation y=(A+((B−A)/(1+((C/x)^D)))) where y=% specific inhibition, A=bottom of the curve, B=top of the curve, C=relative $IC_{50}$=concentration causing 50% inhibition based on the range of the data from top to bottom, D=Hill Slope=slope of the curve.

The following Table 1 and Table 2 describes the relative $IC_{50}$ data vs. human BTK, human EGFR, and human whole blood CD69.

TABLE 1

Relative IC$_{50}$ values of Examples 1-23
[IC$_{50}$ value ± standard deviation (n = number of times tested)]

| Example No. | hBTK Rel IC$_{50}$ (μM) | hEGFR Rel IC$_{50}$ (μM) | HWB CD69 Rel IC$_{50}$ (μM) |
|---|---|---|---|
| 1 | 0.0253 ± 0.00542 (n = 3) | 0.470 ± 0.0936 (n = 3) | 0.393 ± 0.128 (n = 12) |
| 2 | 0.00689 ± 0.00262 (n = 3) | 0.121 ± 0.0664 (n = 3) | 0.141 ± 0.0413 (n = 8) |
| 3 | 0.0758 ± 0.000500 (n = 2) | 6.52 ± 4.60 (n = 2) | 0.595 ± 0.326 (n = 6) |
| 4 | 0.00998 ± 0.00430 (n = 3) | 0.872 ± 0.456 (n = 3) | 0.110 ± 0.0794 (n = 8) |
| 5 | 0.0555 ± 0.0244 (n = 5) | 28.5 ± 21.2 (n = 5) | 0.485 ± 0.234 (n = 14) |
| 6 | 0.0724 ± 0.00422 (n = 2) | 5.18 ± 0.441 (n = 2) | 0.671 ± 0.236 (n = 6) |
| 7 | 0.00973 ± 0.00201 (n = 5) | 0.129 ± 0.0553 (n = 5) | 0.180 ± 0.0460 (n = 7) |
| 8 | 0.0231 ± 0.0000341 (n = 2) | 0.724 ± 0.375 (n = 2) | 0.239 ± 0.0345 (n = 4) |
| 9 | 0.0606 ± 0.000351 (n = 2) | 3.76 ± 1.40 (n = 2) | 0.655 ± 0.295 (n = 4) |
| 10 | 0.0345 ± 0.00808 (n = 2) | 21.2 ± 3.82 (n = 2) | 0.263 ± 0.129 (n = 6) |
| 11 | 0.0181 ± 0.00305 (n = 2) | 0.644 ± 0.0618 (n = 2) | 0.242 ± 0.0912 (n = 4) |
| 12 | 0.00695 ± 0.000395 (n = 2) | 0.509 ± 0.246 (n = 3) | 0.200 ± 0.0524 (n = 9) |
| 13 | 0.0382 ± 0.0169 (n = 2) | 0.450 ± 0.0532 (n = 2) | 0.715 ± 0.0935 (n = 4) |
| 14 | 0.0178 ± 0.00377 (n = 2) | 0.242 ± 0.231 (n = 2) | 0.299 ± 0.143 (n = 8) |
| 15 | 0.00601 ± 0.000579 (n = 2) | 1.37 ± 1.21 (n = 3) | 0.219 ± 0.0860 (n = 5) |
| 16 | 0.00608 (n = 1) | 8.65 ± 2.37 (n = 3) | 0.118 ± 0.0560 (n = 7) |
| 17 | 0.0329 ± 0.000137 (n = 2) | 16.1 ± 8.31 (n = 3) | 0.242 ± 0.0643 (n = 9) |
| 18 | <0.005 (n = 1) | 0.247 ± 0.0993 (n = 2) | 0.0710 ± 0.0128 (n = 4) |
| 19 | <0.005 (n = 1) | 0.523 ± 0.112 (n = 2) | 0.148 ± 0.0331 (n = 4) |
| 20 | 0.0169 ± 0.00393 (n = 2) | 2.22 ± 0.649 (n = 2) | 0.208 ± 0.132 (n = 4) |
| 21 | 0.00884 ± 0.00121 (n = 3) | >100 (n = 1) | 0.160 ± 0.0382 (n = 8) |
| 22 | 0.0310 ± 0.0124 (n = 3) | 3.39 ± 2.07 (n = 3) | 0.227 ± 0.0811 (n = 8) |
| 23 | 0.0241 ± 0.00428 (n = 2) | 26.5 ± 2.88 (n = 2) | 0.475 ± 0.166 (n = 4) |

TABLE 2

Relative IC$_{50}$ values of Examples 24-47
[IC$_{50}$ value ± standard deviation (n = number of times tested)]

| Example No. | hBTK Rel IC$_{50}$ (μM) | hEGFR Rel IC$_{50}$ (μM) | HWB CD69 Rel IC$_{50}$ (μM) |
|---|---|---|---|
| 24 | 0.00853 ± 0.00324 (n = 4) | 1.05 ± 0.392 (n = 4) | 0.177 ± 0.0416 (n = 10) |
| 25 | 0.0193 ± 0.00328 (n = 2) | 1.58 ± 0.110 (n = 2) | 0.306 ± 0.0636 (n = 4) |
| 26 | 0.0302 ± 0.00432 (n = 2) | 4.03 ± 1.92 (n = 2) | 0.490 ± 0.255 (n = 4) |
| 27 | 0.0337 ± 0.0108 (n = 3) | 10.4 ± 11.5 (n = 3) | 0.664 ± 0.314 (n = 4) |
| 28 | 0.0429 ± 0.00509 (n = 2) | 1.47 ± 0.209 (n = 2) | 0.742 ± 0.323 (n = 2) |
| 29 | 0.0177 ± 0.00135 (n = 3) | 3.47 ± 0.911 (n = 3) | 0.584 ± 0.372 (n = 10) |
| 30 | 0.0432 ± 0.0119 (n = 2) | 1.08 ± 0.229 (n = 2) | 0.815 ± 0.110 (n = 4) |
| 31 | 0.00949 ± 0.00321 (n = 4) | 0.366 ± 0.0870 (n = 4) | 0.419 ± 0.118 (n = 7) |
| 32 | 0.00688 ± 0.00137 (n = 2) | 0.194 ± 0.0479 (n = 2) | 0.135 ± 0.0665 (n = 4) |
| 33 | 0.00944 ± 0.00226 (n = 3) | 22.2 ± 19.5 (n = 3) | 0.261 ± 0.145 (n = 12) |
| 34 | 0.0183 (n = 1) | 0.639 ± 0.256 (n = 2) | 0.130 ± 0.0447 (n = 6) |
| 35 | <0.005 (n = 1) | 0.0373 ± 0.0261 (n = 2) | 0.107 ± 0.0454 (n = 4) |
| 36 | 0.00672 ± 0.00170 (n = 2) | 15.2 ± 0.654 (n = 2) | 0.161 ± 0.0710 (n = 4) |
| 37 | <0.005 (n = 1) | 0.306 ± 0.0338 (n = 2) | 0.136 ± 0.0668 (n = 4) |
| 38 | 0.00689 ± 0.000835 (n=2) | 0.908 ± 0.546 (n = 2) | 0.0666 ± 0.0199 (n = 4) |
| 39 | 0.00560 (n = 1) | 1.46 ± 0.200 (n = 2) | 0.103 ± 0.0606 (n = 4) |
| 40 | 0.00558 ± 0.000182 (n = 2) | 0.0549 ± 0.0154 (n = 2) | 0.144 ± 0.0534 (n = 4) |
| 41 | 0.0968 ± 0.0156 (n = 2) | 2.11 ± 0.487 (n = 2) | 2.16 ± 0.420 (n = 2) |
| 42 | 0.0194 ± 0.00167 (n = 2) | 2.82 ± 0.492 (n = 2) | 0.226 ± 0.0530 (n = 4) |
| 43 | <0.005 (n = 1) | 0.676 ± 0.0230 (n = 2) | 0.105 ± 0.0430 (n = 4) |
| 44 | 0.00611 (n = 1) | 0.207 ± 0.0319 (n = 2) | 0.126 ± 0.0297 (n = 8) |
| 45 | 0.0438 ± 0.00417 (n = 2) | 52.6 ± 28.8 (n = 2) | 0.466 ± 0.159 (n = 6) |
| 46 | <0.005 (n = 1) | 6.04 ± 2.09 (n = 2) | 0.157 ± 0.0523 (n = 8) |
| 47 | 0.0067 (n = 1) | 6.1 (n = 1) | 0.355 ± 0.039 (n = 2) |

The relative IC50 data provided for Examples 1-47 in Tables 1 and 2 illustrate the potent binding to human BTK, and comparatively much less potent binding to human EGFR. Further, the IC50 data provided for Examples 1-47 in Tables 1 and 2 for binding to human BTK correlates with the pharmacological inhibition of B cell activation in human whole blood, as measured by CD69 upregulation, in response to stimulation through the B cell receptor. The data illustrate the potent and selective inhibition of BTK signaling by Examples 1-47.

Rat Oral Bioavailability:

The test compound is administered to Sprague-Dawley rats intravenously (IV) at 1 mg/kg (using vehicles of either: 20% CAPTISOL® in 25 mM sodium phosphate buffer, pH2 quantum satis; or 25% DMA, 15% EtOH, 10% propylene glycol, 25% 2-pyrrolidone, and 25% purified water) and orally (PO) at 3 mg/kg (using a vehicle of 1% hydroxyethyl cellulose, 0.25% polysorbate 80, 0.05% Antifoam 1510-US, and purified water quantum satis). Serial blood samples are collected at 0.08, 0.25, 0.5, 1, 2, 4, 8, and 12 h post dose for IV bolus and at 0.25, 0.5, 1, 2, 4, 8, and 12 h post dose after oral administration. After treatment with an EDTA coagulant, plasma is obtained by centrifugation and stored at −70° C. until analysis by LC-MS/MS. Test article concentration is determined in plasma and uploaded into the Watson LIMS™ system where noncompartmental analysis is used to calculate Area Under the Curve (AUC) for both IV and PO arms. Bioavailability (% F) is calculated via the following equation, $$\%F=(AUC_{PO} \times Dose_{IV})/(AUC_{IV} \times Dose_{PO}) \times 100.$$

Table 3 indicates the rat oral bioavailability of select BTK inhibitors.

TABLE 3

Rat Oral Bioavailability (% F) at 3 mg/kg of select BTK inhibitors.

| Example No. | % F (rat) |
|---|---|
| 1 | 74.0% |
| 5 | 36.6% |
| 19 | 79.2% |
| 24 | 41.0% |
| 27 | 38.4% |
| 31 | 54.1% |
| 33 | 44.6% |
| 44 | 36.8% |

The data provided in Table 3 for Examples 1, 5, 19, 24, 27, 31, 33 and 44, illustrate the pharmacologically advantageous oral bioavailabiltiy of the compounds of the invention.

Rat In Vivo Collagen-Induced Arthritis Assay:

A type II collagen-induced arthritis (CIA) rat model may be used to evaluate the therapeutic effects of compounds. Female Lewis rats (Charles River Charles River Laboratories, Inc.) with a mean body weight of 155-175 g are used for the study. Animals are fed with standard rodent chow and provided water ad libitum. Immunization emulsion is prepared with 2 mg/ml bovine collagen-II mixed with an equal volume of incomplete Freund's adjuvant (IFA). Rats are immunized intradermally with 0.4 ml collagen emulsion in two sites each on the lower lumbar region, above the base of the tail on day 1, and again on day 8. Animals are randomized based on the paw thickness and body weight on day 11 into study groups, with 8 rats in each group. Compounds are prepared in 1% HEC/0.25% P80/0.05% anti-foam in purified water and dosed daily via oral gavage for 9 days. Paw thickness is quantitated daily using a caliper measurement in the right ankle site.

The inhibition by the compounds of the invention is evaluated using Dunnett's post test for multiple comparisons for the CIA rat groups treated with the indicated Example compound, at the indicated dose, as compared to CIA rat groups treated with vehicle, and differences of P<0.05 are considered to be significant. Treatment with BTK inhibitor Examples 1, 5, 24, 27, 31 and 33 demonstrate a dose-related reduction in arthritis severity in CIA rats. Mean sum paw thickness is decreased compared to vehicle treated CIA rats. Mean percent paw thickness inhibition during the treatment period illustrates dose-related improvement. Histopathology quantitative analyses shows ankle joint inflammation, bone resorption, and cartilage damage severity scores also show dose-related reductions compared to vehicle treated CIA rats.

Table 4 indicates the in vivo activity for exemplified BTK inhibitors in the collagen-induced arthritis model (SE=standard error).

TABLE 4

CIA model in vivo activity for BTK inhibitors.

| Example No. | test dose (mg/kg/d) | % inhibition paw thickness AUC vs Vehicle control | % paw thickness AUC (mm) ± SE |
|---|---|---|---|
| Vehicle |  | 0 | 78.2 ± 0.8 |
| 1 | 0.5 | 23 | 73.9 ± 2.5 |
| 1 | 1 | 47 | 69.6 ± 2.0 |
| 1 | 3 | 81 | 63.4 ± 1.3 |
| Vehicle |  | 0 | 78.21 ± 0.75 |
| 5 | 1 | 34 | 71.68 ± 2.24 |
| 5 | 3 | 58 | 67.18 ± 1.07 |
| Vehicle |  | 0 | 69.61 ± 1.78 |
| 24 | 1 | 28 | 65.04 ± 2.31 |
| 24 | 3 | 49 | 61.43 ± 4.47 |
| 24 | 10 | 63 | 59.24 ± 1.49 |
| Vehicle |  | 0 | 77.61 ± 0.88 |
| 27 | 1 | 24 | 73.30 ± 0.95 |
| 27 | 3 | 45 | 69.58 ± 1.26 |
| Vehicle |  | 0 | 76.42 ± 1.17 |
| 31 | 1 | 62 | 66.10 ± 1.83 |
| 31 | 3 | 81 | 63.70 ± 0.96 |
| 31 | 10 | 82 | 64.33 ± 1.00 |
| Vehicle |  | 0 | 78.21 ± 0.75 |
| 33 | 0.3 | 24 | 73.61 ± 2.09 |
| 33 | 1 | 52 | 68.32 ± 2.30 |
| 33 | 3 | 59 | 67.00 ± 1.52 |

The data provided in Table 4, for Examples 1, 5, 24, 27, 31 and 33, illustrate the pharmacologically advantageous in vivo efficacy of the compounds of the invention for the inhibition of collagen-induced arthritis in this in vivo model.

Compounds of the invention, for instance Example 1, show an advantageous combination of pharmacological properties, such as potency, high oral in vivo availabilty, in vivo efficacy, and a favorable toxicity profile in preclinical testing. For instance Example 1 demonstrates potent inhibition of hBTK (0.0253±0.00542 uM (n=3)), and inhibition of B Cell activiation in human whole blood (0.393±0.128 uM (n=12)), but much less potent inhibition on hEGFR (0.470±0.0936 uM (n=3)), and demonstrates favorable rat oral bioavailability (% F) of 74% at 3 mg/kg. Further, Example 1 is generally well tolerated when administered in vivo to normal rats for a period of four days, and shows an advantageous lack of toxicity in this in vivo experiment. Thus, Example 1 demonstrates an advantageous combination of favorable pharmacological properties supporting possible use as an orally administered therapeutic agent for inhibition of B cell activation, and treatment for autoimmune and inflammatory diseases such as RA, MS, and SLE.

We claim:

1. A compound of the formula:

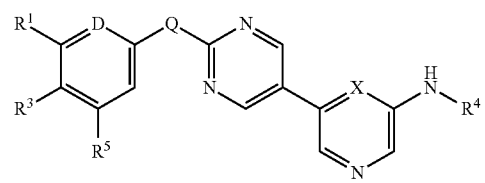

wherein:
D is —CR$^2$— or N;
Q is O or NH;
X is —CH— or N;
R$^1$ is —H, —Cl, —F, —CN, —CH$_3$, —CF$_3$, —OCHF$_2$, —OCH$_3$, —OCF$_3$, or —C≡CH;
R$^2$ is —H, —F or —OCF$_3$;
R$^3$ is —H, —Cl or —F;

R⁴ is

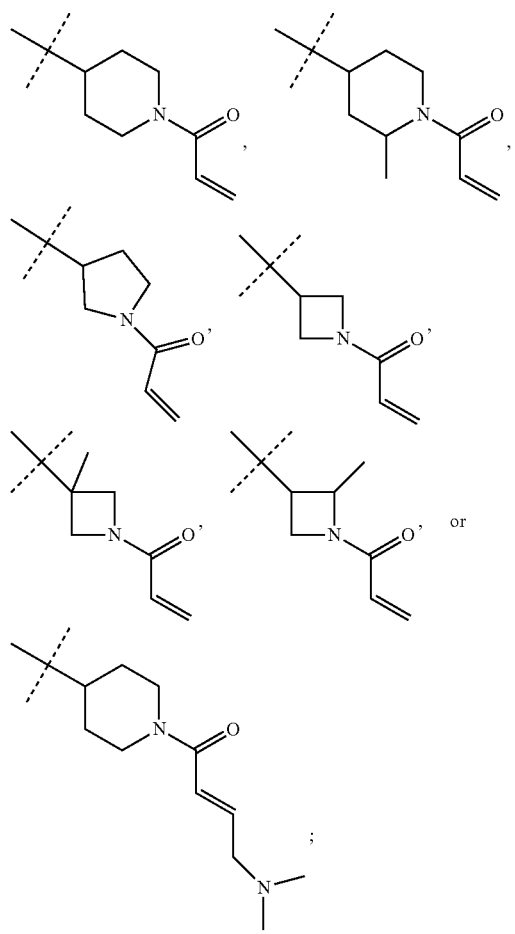

and

R⁵ is —H or —F;

or a pharmaceutically acceptable salt thereof.

2. The compound of claim 1 wherein D is —CR²—, R¹ is —Cl, R³ is —H, and R⁵ is —H, or a pharmaceutically acceptable salt thereof.

3. The compound of claim 1 of the formula:

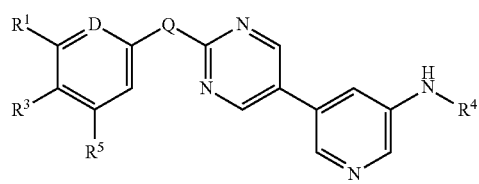

wherein:

D is —CR²— or N;

Q is O or NH;

R¹ is —H, —Cl, —F, —CN, —CH₃, —CF₃, —OCHF₂, —OCH₃, —OCF₃, or —C≡CH;

R² is —H, —F or —OCF₃;

R³ is —H, —Cl or —F;

R⁴ is

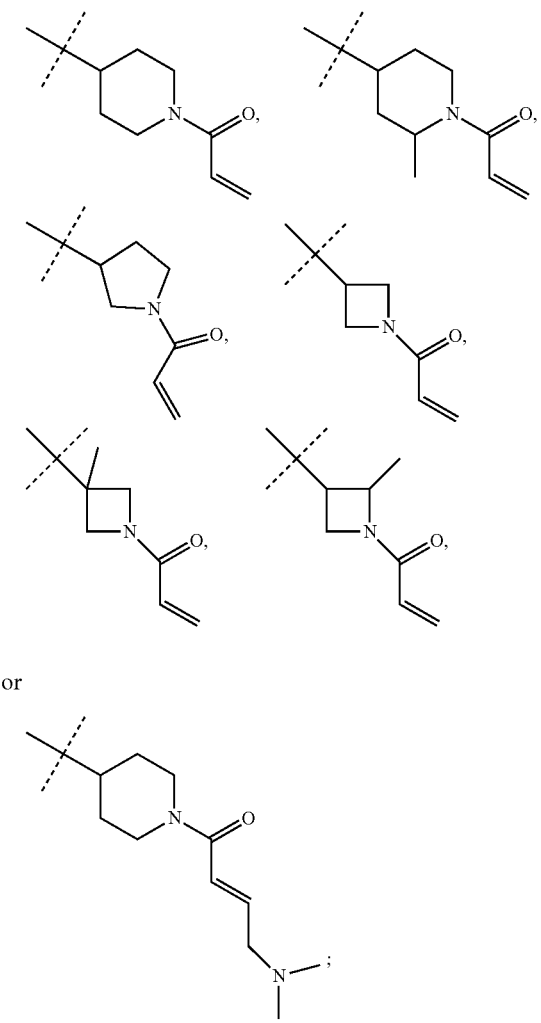

and

R⁵ is —H or —F;

or a pharmaceutically acceptable salt thereof.

4. The compound of claim 3 wherein D is D is —CR²—, R¹ is —Cl, R³ is —H, and R⁵ is —H, or a pharmaceutically acceptable salt thereof.

5. The compound of claim 1 of the formula:

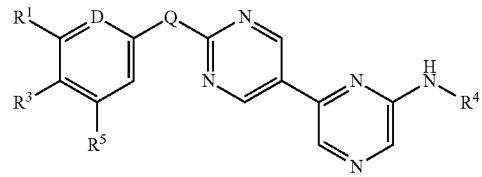

wherein:

D is —CR²— or N;

Q is O or NH;

X is —CH— or N;

R¹ is —H, —Cl, —F, —CN, —CH₃, —CF₃, —OCHF₂, —OCH₃, —OCF₃, or —C≡CH;

R² is —H, —F or —OCF₃;

R³ is H, —Cl or —F;

R⁴ is

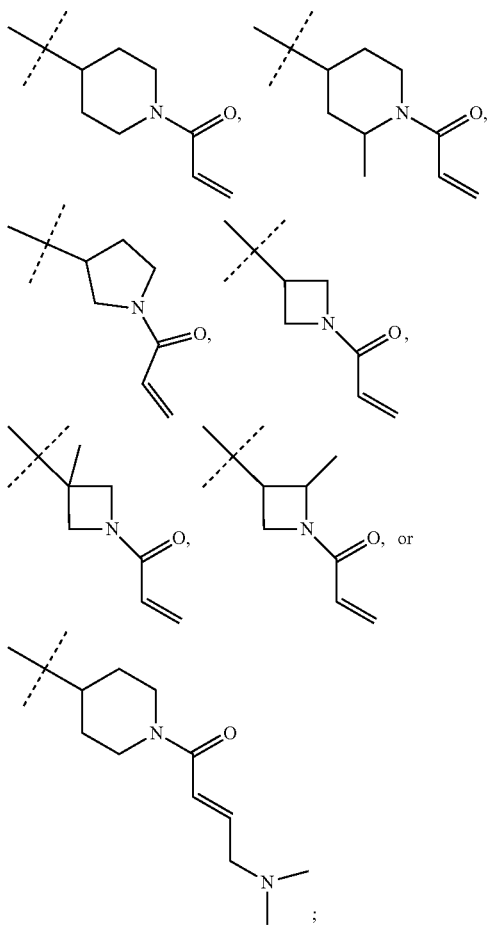

and
R⁵ is —H or —F;
or a pharmaceutically acceptable salt thereof.

6. The compound of claim 5 wherein D is D is —CR²—, R¹ is —Cl, R³ is —H, and R⁵ is —H, or a pharmaceutically acceptable salt thereof.

7. The compound of claim 1 selected from the group consisting of:
1-[3-[[5-[2-(3-chloro-2-fluoro-phenoxy)pyrimidin-5-yl]-3-pyridyl]amino]azetidin-1-yl]prop-2-en-1-one;
3-[5-[5-[(1-prop-2-enoylazetidin-3-yl)amino]-3-pyridyl]pyrimidin-2-yl]oxybenzonitrile;
1-[3-[[5-[2-3-(difluoromethoxy)phenoxy]pyrimidin-5-yl]-3-pyridyl]amino]azetidin-1-yl]prop-2-en-1-one;
1-[(3S)-3-[[5-[2-[3-(difluoromethoxy)phenoxy]pyrimidin-5-yl]-3-pyridyl]amino]pyrrolidin-1-yl]prop-2-en-1-one;
1-[(3S)-3-[[5-[2-(3-chlorophenoxy)pyrimidin-5-yl]-3-pyridyl]amino]pyrrolidin-1-yl]prop-2-en-1-one;
1-[3-[[5-[2-(3-chlorophenoxy)pyrimidin-5-yl]-3-pyridyl]amino]azetidin-1-yl]prop-2-en-1-one;
1-[3-[[5-[2-[3-(trifluoromethyl)phenoxy]pyrimidin-5-yl]-3-pyridyl]amino]azetidin-1-yl]prop-2-en-1-one;
1-[3-[[5-[2-[3-(difluoromethoxy)-4-fluoro-phenoxy]pyrimidin-5-yl]-3-pyridyl]amino]azetidin-1-yl]prop-2-en-1-one;
1-[3-[[5-[2-[3-(trifluoromethoxy)phenoxy]pyrimidin-5-yl]-3-pyridyl]amino]azetidin-1-yl]prop-2-en-1-one;
1-[3-[[5-[2-(3-fluorophenoxy)pyrimidin-5-yl]-3-pyridyl]amino]azetidin-1-yl]prop-2-en-1-one;
1-[3-[[5-[2-(3-chlorophenoxy)pyrimidin-5-yl]-3-pyridyl]amino]-3-methyl-azetidin-1-yl]prop-2-en-1-one;
1-[3-[[5-[2-(3-chloro-4-fluoro-phenoxy)pyrimidin-5-yl]-3-pyridyl]amino]azetidin-1-yl]prop-2-en-1-one;
1-[3-[[5-[2-(3-ethynylphenoxy)pyrimidin-5-yl]-3-pyridyl]amino]azetidin-1-yl]prop-2-en-1-one;
1-[3-[[5-[2-(3-chloroanilino)pyrimidin-5-yl]-3-pyridyl]amino]azetidin-1-yl]prop-2-en-1-one;
(S)-1-(3-((5-(2-((3-(difluoromethoxy)phenyl)amino)pyrimidin-5-yl)pyridin-3-yl)amino)pyrrolidin-1-yl)prop-2-en-1-one;
1-{(3S)-3-[(5-{2-[(6-methylpyridin-2-yl)amino]pyrimidin-5-yl}pyridin-3-yl)amino]pyrrolidin-1-yl}prop-2-en-1-one;
1-[3-[[5-[2-[3-(trifluoromethyl)anilino]pyrimidin-5-yl]-3-pyridyl]amino]azetidin-1-yl]prop-2-en-1-one;
1-[4-[[5-[2-(3-chloroanilino)pyrimidin-5-yl]-3-pyridyl]amino]-1-piperidyl]prop-2-en-1-one;
1-[4-[[5-[2-[(6-methyl-2-pyridyl)amino]pyrimidin-5-yl]-3-pyridyl]amino]-1-piperidyl]prop-2-en-1-one;
1-[4-[[5-[2-[[6-(trifluoromethyl)-2-pyridyl]amino]pyrimidin-5-yl]-3-pyridyl]amino]-1-piperidyl]prop-2-en-1-one;
1-[4-[[5-[2-(2-pyridylamino)pyrimidin-5-yl]-3-pyridyl]amino]-1-piperidyl]prop-2-en-1-one;
(E)-1-[4-[[5-[2-(3-chloroanilino)pyrimidin-5-yl]-3-pyridyl]amino]-1-piperidyl]-4-(dimethylamino)but-2-en-1-one;
1-[3-[[6-[2-[3-(difluoromethoxy)phenoxy]pyrimidin-5-yl]pyrazin-2-yl]amino]azetidin-1-yl]prop-2-en-1-one;
1-[3-[[6-[2-(3-fluorophenoxy)pyrimidin-5-yl]pyrazin-2-yl]amino]azetidin-1-yl]prop-2-en-1-one;
1-[3-[[6-[2-[3-(trifluoromethyl)phenoxy]pyrimidin-5-yl]pyrazin-2-yl]amino]azetidin-1-yl]prop-2-en-1-one;
1-[3-[[6-[2-[3-(trifluoromethoxy)phenoxy]pyrimidin-5-yl]pyrazin-2-yl]amino]azetidin-1-yl]prop-2-en-1-one;
1-[3-[[6-(2-phenoxypyrimidin-5-yl)pyrazin-2-yl]amino]azetidin-1-yl]prop-2-en-1-one;
1-[3-[[6-[2-(3-chlorophenoxy)pyrimidin-5-yl]pyrazin-2-yl]amino]-3-methyl-azetidin-1-yl]prop-2-en-1-one;
1-[3-[[6-[2-(3,5-difluorophenoxy)pyrimidin-5-yl]pyrazin-2-yl]amino]azetidin-1-yl]prop-2-en-1-one;
1-[3-[[6-[2-(3-chlorophenoxy)pyrimidin-5-yl]pyrazin-2-yl]amino]azetidin-1-yl]prop-2-en-1-one;
1-[(2S,3R)-3-[[6-[2-(3-chlorophenoxy)pyrimidin-5-yl]pyrazin-2-yl]amino]-2-methyl-azetidin-1-yl]prop-2-en-1-one, Isomer 1;
1-[(3S)-3-[[6-[2-[3-(trifluoromethoxy)anilino]pyrimidin-5-yl]pyrazin-2-yl]amino]pyrrolidin-1-yl]prop-2-en-1-one;
1-[(3S)-3-[[6-[2-(3-chloroanilino)pyrimidin-5-yl]pyrazin-2-yl]amino]pyrrolidin-1-yl]prop-2-en-1-one;
1-[3-[[6-[2-(3-chloro-4-fluoro-anilino)pyrimidin-5-yl]pyrazin-2-yl]amino]azetidin-1-yl]prop-2-en-1-one;
1-[(3S)-3-[[6-[2-[2-(trifluoromethoxy)anilino]pyrimidin-5-yl]pyrazin-2-yl]amino]pyrrolidin-1-yl]prop-2-en-1-one;
1-[3-[[6-[2-[3-(trifluoromethoxy)anilino]pyrimidin-5-yl]pyrazin-2-yl]amino]azetidin-1-yl]prop-2-en-1-one;
1-[4-[[6-[2-[3-(difluoromethoxy)phenoxy]pyrimidin-5-yl]pyrazin-2-yl]amino]-1-piperidyl]prop-2-en-1-one;
1-[(3S)-3-[[6-[2-[3-(difluoromethoxy)anilino]pyrimidin-5-yl]pyrazin-2-yl]amino]pyrrolidin-1-yl]prop-2-en-1-one;

1-[3-[[6-[2-[(6-methyl-2-pyridyl)amino]pyrimidin-5-yl]
pyrazin-2-yl]amino]azetidin-1-yl]prop-2-en-1-one;
1-[3-[[6-[2-(4-chlorophenoxy)pyrimidin-5-yl]pyrazin-2-
yl]amino]azetidin-1-yl]prop-2-en-1-one;
1-[3-[[6-[2-(3-methoxyphenoxy)pyrimidin-5-yl]pyrazin-
2-yl]amino]azetidin-1-yl]prop-2-en-1-one;
1-[3-[[6-[2-[2-(trifluoromethoxy)anilino]pyrimidin-5-yl]
pyrazin-2-yl]amino]azetidin-1-yl]prop-2-en-1-one;
1-[4-[[6-[2-(3-chlorophenoxy)pyrimidin-5-yl]pyrazin-2-
yl]amino]-1-piperidyl]prop-2-en-1-one;
(E)-1-[4-[[6-[2-(3-chlorophenoxy)pyrimidin-5-yl]
pyrazin-2-yl]amino]-1-piperidyl]-4-(dimethylamino)
but-2-en-1-one;
(E)-1-[4-[[6-[2-(3-chloroanilino)pyrimidin-5-yl]pyrazin-
2-yl]amino]-1-piperidyl]-4-(dimethylamino)but-2-en-
1-one;
1-[4-[[5-[2-(3-chloroanilino)pyrimidin-5-yl]-3-pyridyl]
amino]-2-methyl-1-piperidyl]prop-2-en-1-one, and
or a pharmaceutically acceptable salt thereof.

8. The compound of claim 1 which is:

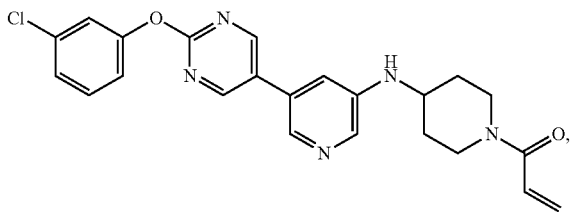 [SMILES: C=CC(=O)N1CCC(Nc2cncc(-c3cnc(Oc4cccc(Cl)c4)nc3)c2)CC1]

or a pharmaceutically acceptable salt thereof.

9. The compound of claim 1 which is:

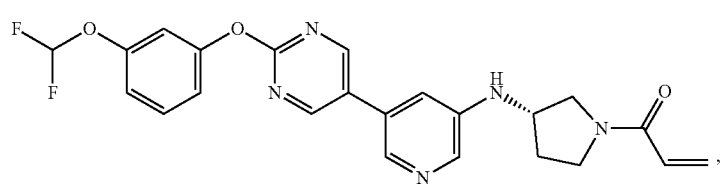 [SMILES: C=CC(=O)N1CC[C@H](Nc2cncc(-c3cnc(Oc4cccc(OC(F)F)c4)nc3)c2)C1]

or a pharmaceutically acceptable salt thereof.

10. The compound of claim 1 which is:

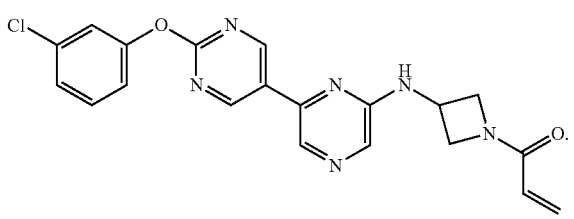 [SMILES: C=CC(=O)N1CC(Nc2cncc(-c3cnc(Oc4cccc(Cl)c4)nc3)n2)C1]

11. The compound of claim 1 which is:

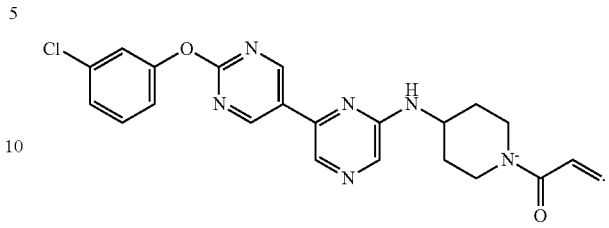

12. The compound of claim 1 which is:

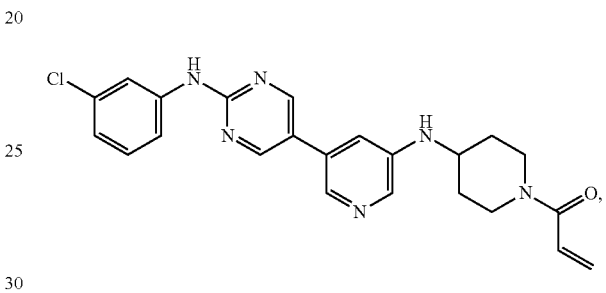

or a pharmaceutically acceptable salt thereof.

13. The compound of claim 1 which is:

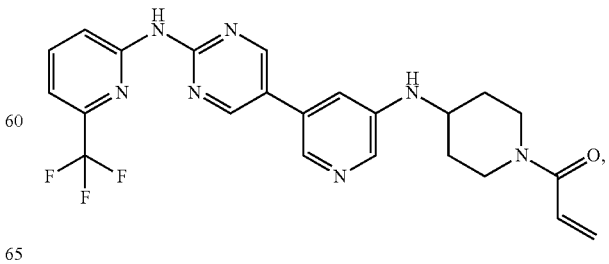

or a pharmaceutically acceptable salt thereof.

14. A pharmaceutical composition comprising a compound of claim 1, or a pharmaceutically acceptable salt thereof, and a pharmaceutically acceptable carrier, diluent or excipient.

* * * * *